United States Patent
Kim et al.

(10) Patent No.: US 11,679,024 B2
(45) Date of Patent: Jun. 20, 2023

(54) MEDICAL COOLING SYSTEM AND MEDICAL COOLING DEVICE USING SAME

(71) Applicants: RECENSMEDICAL, INC., Ulsan (KR); Ulsan National Institute of Science and Technology, Ulsan (KR)

(72) Inventors: Gun-Ho Kim, Ulsan (KR); Jae Bum Cho, Seoul (KR); Kyong Kwan Ro, Hwaseong (KR); Boo Seong Park, Yongin (KR); Chui Ho Lee, Yongin (KR)

(73) Assignees: RECENSMEDICAL, INC., Ulsan (KR); ULSAN NATIONAL INSTITUTE OF SCIENCE AND TECHNOLOGY, Ulsan (KR)

(*) Notice: Subject to any disclaimer, the term of this patent is extended or adjusted under 35 U.S.C. 154(b) by 0 days.

(21) Appl. No.: 17/941,999

(22) Filed: Sep. 9, 2022

(65) Prior Publication Data

US 2023/0000666 A1    Jan. 5, 2023

Related U.S. Application Data

(63) Continuation of application No. PCT/KR2021/009073, filed on Jul. 14, 2021.

(30) Foreign Application Priority Data

Jul. 14, 2020  (KR) .......................... 10-2020-0087100
Feb. 8, 2021   (KR) .......................... 10-2021-0017490

(51) Int. Cl.
  *A61F 7/00*    (2006.01)
  *A61B 18/02*   (2006.01)
  *A61B 18/00*   (2006.01)

(52) U.S. Cl.
  CPC ................ *A61F 7/00* (2013.01); *A61B 18/02* (2013.01); *A61B 18/0218* (2013.01);
  (Continued)

(58) Field of Classification Search
  CPC .......... A61M 19/00; A61M 2205/3368; A61M 2205/3606; A61M 2202/03;
  (Continued)

(56) References Cited

U.S. PATENT DOCUMENTS 6,141,985 A  * 11/2000  Cluzeau ................ A61F 7/0085
                                                  606/22
7,147,654 B2   12/2006  Baumgardner et al.
(Continued)

FOREIGN PATENT DOCUMENTS

KR      100963373 B1     6/2010
KR     20160146337 A    12/2016
(Continued)

OTHER PUBLICATIONS

PCT/KR2021/009073 International Search Report and Written Opinion dated Nov. 23, 2021.
(Continued)

*Primary Examiner* — Joseph A Stoklosa
*Assistant Examiner* — Adam J Avigan
(74) *Attorney, Agent, or Firm* — Wilson Sonsini Goodrich & Rosati

(57) ABSTRACT

Proposed is a filter fixing module mounted to a handpiece cooling device having a connecting unit such that a refrigerant supply unit is coupled thereto, the filter fixing module including a body having a support surface formed in a plate shape, and a receiving surface formed on an edge of the support surface and protruding in a first direction relative to the support surface so as to prevent removal of a filter received in the support surface, and a grip unit connected to
(Continued)

the body, wherein the grip unit comprises a first grip member and a second grip member extending in directions opposite to the protruding direction of the receiving surface relative to the body.

23 Claims, 28 Drawing Sheets

(52) U.S. Cl.
CPC .. *A61F 7/0085* (2013.01); *A61B 2018/00005* (2013.01); *A61B 2018/00791* (2013.01); *A61F 2007/0063* (2013.01); *A61F 2007/0087* (2013.01)

(58) Field of Classification Search
CPC ...... A61M 2205/8225; A61M 2210/04; A61M 5/44; A61F 7/00; A61F 2007/0087; A61F 2007/0063; A61F 7/0085; A61F 2007/0064; A61B 18/0218; A61B 2018/00452; A61B 18/02; A61B 2018/0237; A61B 2018/00791
See application file for complete search history.

(56) References Cited

U.S. PATENT DOCUMENTS

| | | | |
|---|---|---|---|
| 8,083,734 B2* | 12/2011 | Steinfatt | A61B 18/0218 606/26 |
| 2008/0200910 A1* | 8/2008 | Burger | A61B 18/0218 604/113 |
| 2009/0124972 A1* | 5/2009 | Fischer | A61B 18/02 604/113 |
| 2014/0276708 A1* | 9/2014 | Karnik | A61B 18/02 606/21 |

FOREIGN PATENT DOCUMENTS

| | | |
|---|---|---|
| KR | 101935597 B1 | 1/2019 |
| KR | 101997891 B1 | 7/2019 |
| KR | 20200070095 A | 6/2020 |
| KR | 20200070139 A | 6/2020 |
| WO | WO-2022015067 A1 | 1/2022 |

OTHER PUBLICATIONS

KR Application No. 10-2021-0017490 Written Decision on Registration dated Feb. 3, 2023.

* cited by examiner (a)

(b)

S1500

MEDICAL COOLING SYSTEM AND MEDICAL COOLING DEVICE USING SAME

CROSS-REFERENCE

This application is a continuation of PCT application No. PCT/KR2021/009073, filed Jul. 14, 2021, which claims the benefit of KR patent application No. 10-2021-0017490, filed on Feb. 8, 2021, which claims the benefit of KR patent application No. 10-2020-0087100, filed on Jul. 14, 2020, all of which are incorporated herein by reference in their entirety.

TECHNICAL FIELD

The present disclosure relates generally to a cooling system for performing cooling and a cooling device using the same and, more particularly, to a cooling device and a cooling method of the same in which the cooling device uses a filter fixing module easily removed therefrom to cool a target safely.

BACKGROUND ART

In a social environment in which skin diseases are increasing and interest in beauty culture is rapidly increasing in modern society, interest in skin procedures and skin care is rapidly increasing. Accordingly, interest and research on a cooling device for skin care and skin disease treatment are increasing.

Meanwhile, a conventional cooling device for skin treatment, particularly, a cooling device which uses the method of cooling skin by spraying a refrigerant to the skin is a supply source of a refrigerant, and has been used by connecting a refrigerant tank to the cooling device through a hose or by mounting a refrigerant cartridge to the cooling device.

However, the existing cooling device is not compatible with both a hose connected to the refrigerant tank and the refrigerant cartridge, and is divided into a cooling device for the refrigerant tank and a cooling device for the refrigerant cartridge to be used individually.

Meanwhile, the cooling device for skin treatment may inevitably have a safety problem in that the cooling device performs treatment on the skin. For example, impurities contained in a refrigerant may be delivered to a targeted area of the skin, which may cause skin to be infected.

Therefore, research on the structure and control method of the cooling device that can perform cooling while increasing the ease of use and ensuring safety is required.

DISCLOSURE

Technical Problem

A problem which the present disclosure is intended to solve is to provide a filter fixing module which is mounted to a cooling device and receives a filter which filters out impurities in a refrigerant.

Another problem the present disclosure is to provide the cooling device from which the filter fixing module is mounted and removed.

Problems which the present disclosure intends to solve are not limited to the tasks described above, and problems not mentioned will be clearly understood by those skilled in the art to which the present disclosure belongs from the present specification and the accompanying drawings.

Technical Solution

According to the embodiment of the present specification, a filter fixing module mounted to a handpiece cooling device having a connecting unit such that a refrigerant supply unit is coupled thereto may include: a body having a support surface formed in the shape of a flat plate in a first direction, and a receiving surface formed on the edge of the support surface and protruding in a second direction relative to the support surface so as to prevent the removal of a filter received in the support surface—the first direction and the second direction are different; and a grip unit connected to the body, wherein the grip unit includes a first grip member and a second grip member extending in a direction opposite to the extending direction of the receiving surface relative to the body.

According to the embodiment of the present specification, the cooling device which performs cooling by spraying a refrigerant introduced from the refrigerant supply unit holding the refrigerant to a targeted area includes: a valve which controls the flow of a refrigerant; a nozzle which sprays a refrigerant to the targeted area; a tube providing the moving passage of a fluid such that a refrigerant supplied from the refrigerant supply unit passes through the valve and is discharged through the nozzle; a main body in which the valve, the nozzle, and the tube are received; first threads coupled to a first housing, second threads coupled to the refrigerant supply unit, and a coupling member which includes a refrigerant moving hole formed to introduce a refrigerant supplied from the refrigerant supply unit into the tube and is located between the refrigerant supply unit and the tube; the body having the support surface formed in a plate shape, and the receiving surface formed on the edge of the support surface and protruding in the first direction relative to the support surface; and the filter fixing module including the grip unit connected to the body, wherein the grip unit includes the first grip member and the second grip member extending in directions opposite to the protruding direction of the receiving surface relative to the body, and the filter may be disposed between the support surface and the refrigerant moving hole such that impurities of a refrigerant introduced into the refrigerant moving hole are filtered out by the filter when the filter fixing module is located in an portion of the coupling member with the filter disposed in the receiving surface.

The solution of the present disclosure is not limited to the above-mentioned solutions, and solutions not mentioned will be clearly understood by those skilled in the art to which the present disclosure belongs from the present specification and the accompanying drawings.

Advantageous Effects

According to an embodiment of the present disclosure, the filter fixing module may be easily mounted to and removed from the cooling device through the structure of the filter fixing module protruding to the outside of the cooling device.

According to the embodiment of the present disclosure, when the filter fixing module is removed from the cooling device, the fluid passage in which a refrigerant can move is formed, thereby minimizing a user's inconvenience due to expansion of the refrigerant.

Effects according to the present specification are not limited to the above-mentioned effects, and effects not mentioned can be clearly understood by those skilled in the art to which the present disclosure belongs from the present specification and the accompanying drawings.

DESCRIPTION OF DRAWINGS

FIG. 2 is a view illustrating a cooling system (10) using a cartridge as a refrigerant supply unit (4000), and FIG. 3 is a view illustrating a cooling system (10) using a refrigerant tank as the refrigerant supply unit (4000).

BEST MODE

Figure 1:
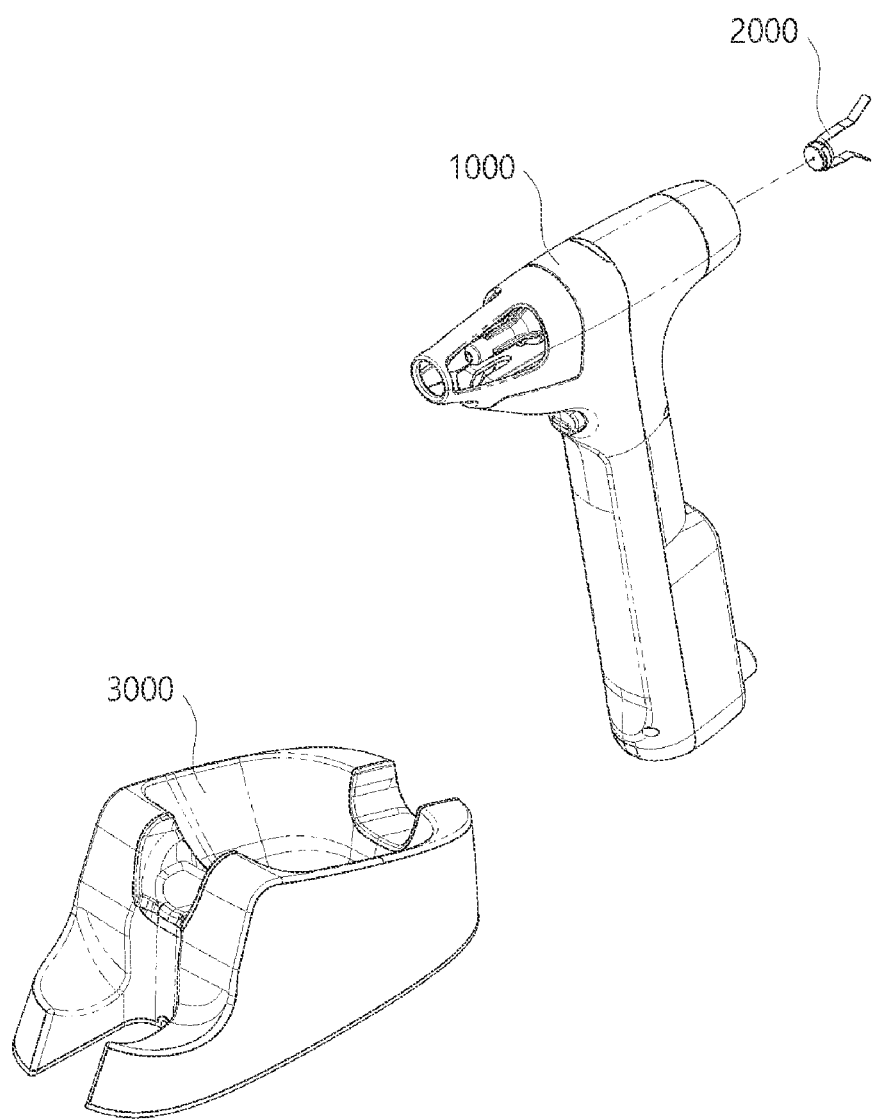
FIG. 1 is a view illustrating a cooling system (10) according to the embodiment of the present specification.

The above-described objectives, features and advantages of the present application will become more apparent through the following detailed description in conjunction with the accompanying drawings. However, the present application may have various changes and may have various embodiments, but specific embodiments will be exemplified hereinafter in the drawings and will be described in detail.

In the drawings, the thicknesses of layers and regions are exaggerated for clarity, and in addition, indicating that an element or layer is located "on" or "on" another component or layer may include all cases in which the element or layer is located directly on another element or layer and still another element or layer is located therebetween. Throughout the specification, like reference numerals refer to like elements in principle. In addition, components having the same function within the scope of the same idea shown in the drawings of each embodiment will be described using the same reference numerals, and overlapping descriptions thereof will be omitted.

When it is determined that a detailed description of a known function or configuration related to the present application may unnecessarily obscure the gist of the present application, the detailed description thereof will be omitted. In addition, ordinal numbers (for example, first and second, etc.) used in the description process of the present specification are only identifiers for distinguishing one component from other components.

In addition, terms "module" and "part" for components used in the following embodiments are given or mixed in consideration of only the ease of writing the specification, and do not have meanings or roles distinct from each other by themselves.

In the following embodiments, a singular expression includes a plural expression unless the context clearly dictates otherwise.

In the following embodiments, terms such as "include" or "have" mean that there are features or components described in the specification, and do not preclude the possibility that one or more other features or components may be added.

In the drawings, the size of each component may be exaggerated or reduced for convenience of description. For example, the size and thickness of each component shown in the drawings are arbitrarily indicated for convenience of description, and the present disclosure is not necessarily limited thereto.

In cases in which a certain embodiment may be realized differently, a specific process sequence may be different from the described sequence. For example, two processes described in succession may be performed substantially simultaneously, or may be performed in an order opposite to the described order.

In the following embodiments, when it is said that a film, a region, and a component are connected to each other, it includes not only a case in which the film, the region, and the component are directly connected to each other, but also a case in which other film, region, and component are placed between the film, the region, and the component such that the film, the region, and the component are indirectly connected to each other.

For example, in the present specification, when it is said that a film, a region, and a component are electrically connected to each other, it includes not only a case in which the film, region, and component is directly electrically connected to each other, but also other membrane, region, and component are placed between the film, region, and component such that the film, region, and component are indirectly electrically connected to each other.

According to the embodiment of the present specification, a filter fixing module mounted to a handpiece cooling device having a connecting unit such that a refrigerant supply unit is coupled thereto and includes: a body having a support surface formed in a plate shape, and a receiving surface formed on an edge of the support surface and protruding in a first direction relative to the support surface so as to prevent removal of a filter received in the support surface, and a grip unit connected to the body, wherein the grip unit may include a first grip member and a second grip member extending in directions opposite to the protruding direction of the receiving surface relative to the body.

According to the embodiment of the present specification, there may be provided the filter fixing module including: a perforating member which has a body having a shape protruding from the support surface at the same side as a side of each of the first grip member and the second grip member relative to the support surface, wherein the perforating member has a hollow hole through which a refrigerant introduced from the refrigerant supply unit moves when the refrigerant supply unit is coupled to the connecting unit, wherein the hollow hole includes a first end part which receives a refrigerant introduced from the refrigerant supply unit, and a second end part which is adjacent to the support surface and discharges a refrigerant to the handpiece cooling device.

According to the embodiment of the present specification, there may be provided the filter fixing module in which the first grip member is provided to have a shape of a bent flat plate including a 1-1 region extending in a second direction and a 2-1 region extending in a third direction having a predetermined angle to the second direction, the second grip member is provided to have a shape of a bent flat plate including a 1-2 region extending substantially parallel with the second direction and a 2-2 region extending in a fourth direction having a predetermined angle to the second direction, the 1-1 region of the first grip member and the 1-2 region of the second grip member are spaced by a first distance apart from each other and are substantially parallel with each other, and a maximum separation distance between the 2-1 region of the first grip member and the 2-2 region of the second grip member is longer than the first distance.

According to the embodiment of the present specification, there may be provided the filter fixing module in which a distance by which each of the 2-1 region of the first grip member and the 2-2 region of the second grip member is spaced apart from the support surface is longer than a distance by which the first end part of the perforating member is spaced apart from the support surface.

According to the embodiment of the present specification, there may be provided the filter fixing module in which the body and the perforating member have a unified shape, and a connection hole is formed in a center part of the support surface connected to the second end part of the perforating member, the connection hole being configured to discharge a refrigerant introduced from the second end part of the perforating member to the filter received by the receiving surface.

According to the embodiment of the present specification, there may be the filter fixing module which further includes a first sealing member having an outer diameter smaller than an outer diameter of the receiving surface such that at least a portion of the first sealing member is received in the receiving surface, wherein the first sealing member includes a hollow hole constituting a passage through which a refrigerant passing through the connection hole of the support surface is received in the first sealing member and is discharged to the handpiece cooling device such that leakage of a refrigerant through a contact surface between the support surface and the first sealing member is decreased.

According to the embodiment of the present specification, there may be provided the filter fixing module in which a length of the receiving surface protruding in the first direction from the support surface is shorter than a thickness of the first sealing member, so when the first sealing member is received in the receiving surface, at least a portion of the first sealing member protrudes from the receiving surface to the outside.

According to the embodiment of the present specification, there may be provided the filter fixing module which further includes a second sealing member having a through hole, and decreasing leakage of a refrigerant to be supplied to the hollow hole of the perforating member from the refrigerant supply unit to an outer surface of the perforating member, wherein an inner diameter of the second sealing member defined by the through hole is larger than an outer diameter of the perforating member.

According to the embodiment of the present specification, there may be provided the filter fixing module in which a length of the body of the perforating member is longer than a thickness of the second sealing member, so when the perforating member is received in the through hole of the second sealing member, the first end part of the perforating member protrudes to an outside of the second sealing member.

According to the embodiment of the present specification, the filter fixing module may be provided in which the first sealing member may be made of plastic or rubber, and more specifically, made of Teflon or Nylon 6 (Nylon 6-6).

According to the embodiment of the present specification, the filter fixing module may be provided in which the second sealing member may be made of plastic or rubber, and more specifically, made of Teflon or Nylon 6 (Nylon 6-6).

According to the embodiment of the present specification, there may be provided the filter fixing module in which the filter is configured to be disposed between the first sealing member and the second sealing member.

According to the embodiment of the present specification, there may be provided the filter fixing module in which the filter is configured to be disposed between the first sealing member and the support surface.

According to another embodiment of the present specification, the filter fixing module may have the first sealing member fixed thereto by using adhesive.

According to the another embodiment of the present specification, the second sealing member may not be included in the filter fixing module, but may be included in the refrigerant supply unit, and in this case, the second sealing member may be coupled mechanically to the refrigerant supply unit, or may be bonded to the refrigerant supply unit through adhesive.

According to the embodiment of the present specification, there may be provided a medical cooling device which cools a targeted area by spraying a refrigerant introduced from the refrigerant supply unit holding the refrigerant to the targeted area, the cooling device including: a valve which controls a flow of a refrigerant; a nozzle which sprays a refrigerant to the targeted area; a tube providing a moving passage of a fluid such that a refrigerant supplied from the refrigerant supply unit passes through the valve and is discharged through the nozzle; a main body in which the valve, the nozzle, and the tube are received; a coupling member including first threads coupled to a first housing, second threads coupled to the refrigerant supply unit, and a refrigerant moving hole formed to introduce a refrigerant supplied from the refrigerant supply unit into the tube, the coupling member being located between the refrigerant supply unit and the tube; and the filter fixing module including the body having the support surface formed in a plate shape and the receiving surface formed on the edge of the support surface by protruding therefrom in the first direction relative to the support surface, and the grip unit connected to the body, wherein the grip unit includes the first grip member and the second grip member extending in directions opposite to the protruding direction of the receiving surface relative to the body, and the filter is disposed between the support surface and the refrigerant moving hole such that impurities of a refrigerant introduced into the refrigerant moving hole are filtered out by the filter when the filter fixing module is located in a portion of the coupling member, with the filter disposed in the receiving surface.

According to the embodiment of the present specification, the second threads may include at least two grooved members, and the first grip member and the second grip member may be fitted into the at least two grooved members, respectively, such that the filter fixing module can be connected to the coupling member.

According to the embodiment of the present specification, when a force is applied in a direction in which the first grip member and the second grip member approach each other while the first grip member and the second grip member are fitted into the at least two grooved members, respectively, the first grip member and the second grip member may be removed from the at least two grooved members, respectively.

According to the embodiment of the present specification, the medical cooling device may further include: the connecting unit having the coupling member and the first housing, wherein the first housing may include a first coupling part coupled to a coupling element formed on an outer surface of the main body, and a second coupling part coupled to the first threads formed on an outer surface of the coupling member.

According to the embodiment of the present specification, the medical cooling device may further include a control module which controls opening and closing of the valve.

According to the embodiment of the present specification, the filter fixing module may include the perforating member which has a body having a shape protruding from the support surface at the same side as a side of each of the first grip member and the second grip member relative to the support surface, and perforates the refrigerant supply unit when the refrigerant supply unit is coupled to the second threads, wherein the body may have the hollow hole through which a refrigerant introduced from the refrigerant supply unit moves, wherein the hollow hole may include the first end part which receives a refrigerant introduced from the refrigerant supply unit, and the second end part which is adjacent to the support surface and discharges a refrigerant toward the tube.

According to the embodiment of the present specification, there may be provided the medical cooling device in which the first grip member is provided to have a shape of a bent flat plate including the 1-1 region extending in a second direction and the 2-1 region extending in the third direction having a predetermined angle to the second direction, the second grip member is provided to have a shape of a bent flat plate including the 1-2 region extending substantially parallel with the second direction and the 2-2 region extending in a fourth direction having a predetermined angle to the second direction, the 1-1 region of the first grip member and the 1-2 region of the second grip member is spaced by a first distance apart from each other and are substantially parallel with each other, and a maximum separation distance between the 2-1 region of the first grip member and the 2-2 region of the second grip member is longer than the first distance.

According to the embodiment of the present specification, there may be provided the medical cooling device in which a distance by which each of the 2-1 region of the first grip member and the 2-2 region of the second grip member is spaced apart from the support surface is longer than a distance by which the first end part of the perforating member is spaced apart from the support surface.

According to the embodiment of the present specification, there may be provided the medical cooling device in which the body and the perforating member have a unified shape, and the connection hole is formed in the center part of the support surface connected to the second end part of the perforating member, the connection hole being configured to discharge a refrigerant introduced from the second end part of the perforating member to the filter received by the receiving surface.

According to the embodiment of the present specification, there may be provided the medical cooling device in which the filter fixing module further includes the first sealing member having an outer diameter smaller than an outer diameter of the receiving surface such that at least a portion of the first sealing member is received in the receiving surface, wherein the first sealing member includes a hollow hole constituting a passage through which a refrigerant passing through the connection hole of the support surface is received in the first sealing member and is discharged to the tube such that leakage of a refrigerant through a contact surface between the support surface and the first sealing member is decreased.

According to the embodiment of the present specification, there may be provided the medical cooling device in which a length of the receiving surface protruding in the first direction from the support surface is shorter than a thickness of the first sealing member, so when the first sealing member is received in the receiving surface, at least a portion of the first sealing member protrudes from the receiving surface to the outside so as to be in contact with the coupling member.

According to the embodiment of the present specification, there may be provided the medical cooling device in which the filter fixing module further includes the second sealing member which has a through hole and reduces leakage of a refrigerant to be supplied to the hollow hole of the perforating member from the refrigerant supply unit to an outer surface of the perforating member, wherein an inner diameter of the second sealing member defined by the through hole of the second sealing member is larger than an outer diameter of the perforating member.

According to the embodiment of the present specification, there may be provided the medical cooling device in which a length of the body of the perforating member is longer than a thickness of the second sealing member, so when the perforating member is received in the through hole of the second sealing member, the first end part of the perforating member protrudes to an outside of the second sealing member to be in contact with a refrigerant discharge hole of the refrigerant supply unit.

According to the embodiment of the present specification, the filter fixing module may be provided in which the first sealing member may be made of plastic or rubber, and more specifically, made of Teflon or Nylon 6 (Nylon 6-6).

According to the embodiment of the present specification, the filter fixing module may be provided in which the second sealing member may be made of plastic or rubber and, more specifically, made of Teflon or Nylon 6 (Nylon 6-6).

According to the embodiment of the present specification, there may be provided the medical cooling device in which the filter is configured to be disposed between the first sealing member and the second sealing member.

According to the embodiment of the present specification, there may be provided the medical cooling device in which the filter is configured to be disposed between the first sealing member and the support surface.

According to the embodiment of the present specification, there may be provided the medical cooling device in which the second threads include at least two grooved members, at least a portion of the 1-1 region of the first grip member is received in a first grooved member which is one of the at least two grooved members formed substantially parallel with each other in the second direction, and at least a portion of the 1-2 region of the second grip member is received in a second grooved member which is one of the at least two grooved members formed substantially parallel with each other in the second direction, so the filter fixing module is mounted to the coupling member.

The present disclosure relates to a cooling system for performing cooling and a cooling device using the same, and more particularly, relates to a cooling device and a cooling method of the same in which the filter fixing module easily removed therefrom is used such that a target is safely cooled.

According to the embodiment of the present specification, for beauty or treatment of a target, the cooling system may be used to cool the target such that the target can be in a cooled state, and in this case, a cooling control method may be used such that the target is not damaged due to over-cooling or the like.

The target may refer to a target to be cooled using the cooling system. For example, a target may refer to a target to receive skin cosmetic treatment in which cooling is used. Specifically, a target may include parts of a body, including moles, warts, corns, and acne scars, etc. which can be removed by cooling a local area, or may include a portion of a body that requires local anesthesia during laser treatment such as hair removal, dermabrasion, or Botox treatment. For another example, a target may refer to a target to be made into anesthesia or pain-free state for receiving medical procedures. Specifically, a target may refer to a part of the body including nerves, such as diseased eyes, skin, and gums.

Cooling means lowering the temperature of a target to be cooled by absorbing the thermal energy of the target to be cooled by applying cooling energy to the target to be cooled. Here, cooling energy expresses the escape of heat by cooling, and may be understood as a concept for expressing decrease in thermal energy. For example, cooling is applying cooling energy to a target to be cooled by "spraying" a refrigerant or air gas to the target to be cooled. For another example, cooling is applying cooling energy to a target to be cooled by applying cooling energy to a cooling medium and "contacting" the cooling medium to the target to be cooled. In other words, cooling should be understood as a comprehensive concept including various methods of applying cooling energy to a target to be cooled. Hereinafter, for convenience of explanation, cooling a target through a non-contact method of using a refrigerant is described as a main embodiment, but the technical idea of the present specification is not limited thereto.

The cooling system may also be used for treatment such as inflammation relief (e.g., acne relief), itch relief, for pigmented lesion treatment, vascular lesion treatment, blemish removal, and fat removal. Alternatively, the cooling system may cool a target to directly destroy at least a portion of the target. For example, when a target is a part of the body including the above-mentioned skin moles, warts, and corns, etc., the cooling system provides cooling energy to the target through the surface of the target such that tissue in the target may be necrotic or killed by the provided cooling energy. For another example, the cooling system provides cooling energy to a target surface by spraying a refrigerant on the target surface, and the provided cooling energy makes the temperature of a nerve distributed under the target surface to be below a temperature at which the nerves are temporarily paralyzed or nerve transmission is blocked, whereby the target may be placed under anesthesia or analgesia. The cooling system may cool the target surface and the inside of the target to an appropriate temperature range in order to maintain such anesthesia or analgesia for a predetermined period of time.

Hereinafter, for convenience of explanation, a case in which a target is skin and the cooling system sprays a refrigerant on the surface of the skin to deliver cooling energy thereto is described as a main embodiment, but the technical idea of the present specification is not limited thereto and may be applied to any part of a body.

Hereinafter, the cooling system 10 according to the embodiment of the present specification will be described with reference to FIGS. 1 to 4.

FIG. 1 is a view illustrating the cooling system 10 according to the embodiment of the present specification. Referring to FIG. 1, the cooling system 10 may include the cooling device 1000, the filter fixing module 2000, and a stand 3000.

The cooling device 1000 may provide cooling energy to a target to cool a target. Specifically, as described later, the cooling device 1000 may control the temperature of a refrigerant flowing through a flow path in the cooling device and may cool a target by delivering a refrigerant having targeted temperature to the target.

The cooling device 1000 may be coupled with the filter fixing module 2000 and may filter out impurities contained in a refrigerant introduced from the refrigerant supply unit 4000. Furthermore, the cooling device 1000 may cool a target with the refrigerant from which the impurities are filtered out. Through this, the cooling system 10 according to the embodiment of the present application may safely cool the target such that the target is not contaminated or infected.

The cooling device 1000 may be mounted on the stand 3000 after or during use. For example, the cooling device 1000 may be mounted on the stand 3000 in an off state. For another example, the cooling device 1000 may be mounted on the stand 3000 while power is supplied thereto according to a user's convenience.

The cooling device 1000 may be embodied as a portable device to which a cartridge is connected such that a user can easily carry the device or as a handpiece connected to a large device such as a refrigerant tank.

The cooling device 1000 may be mounted to the stand 3000. Specifically, the stand 3000 is designed to have a structure corresponding to the cooling device 1000, so a user may mount the cooling device 1000 on the stand 3000 during or after use of the cooling device 1000.

As described later, the stand 3000 may include a temperature measurement area in which temperature can be measured to determine whether a sensor module 1400 of the cooling device 1000 operates normally, and may have a shape to protect the cooling device 1000 from external impact. The temperature measurement area of the stand 3000 will be described in detail in FIG. 20.

Meanwhile, in the cooling system 10 disclosed in the present specification, the stand 3000 may be omitted.

Figure 2:
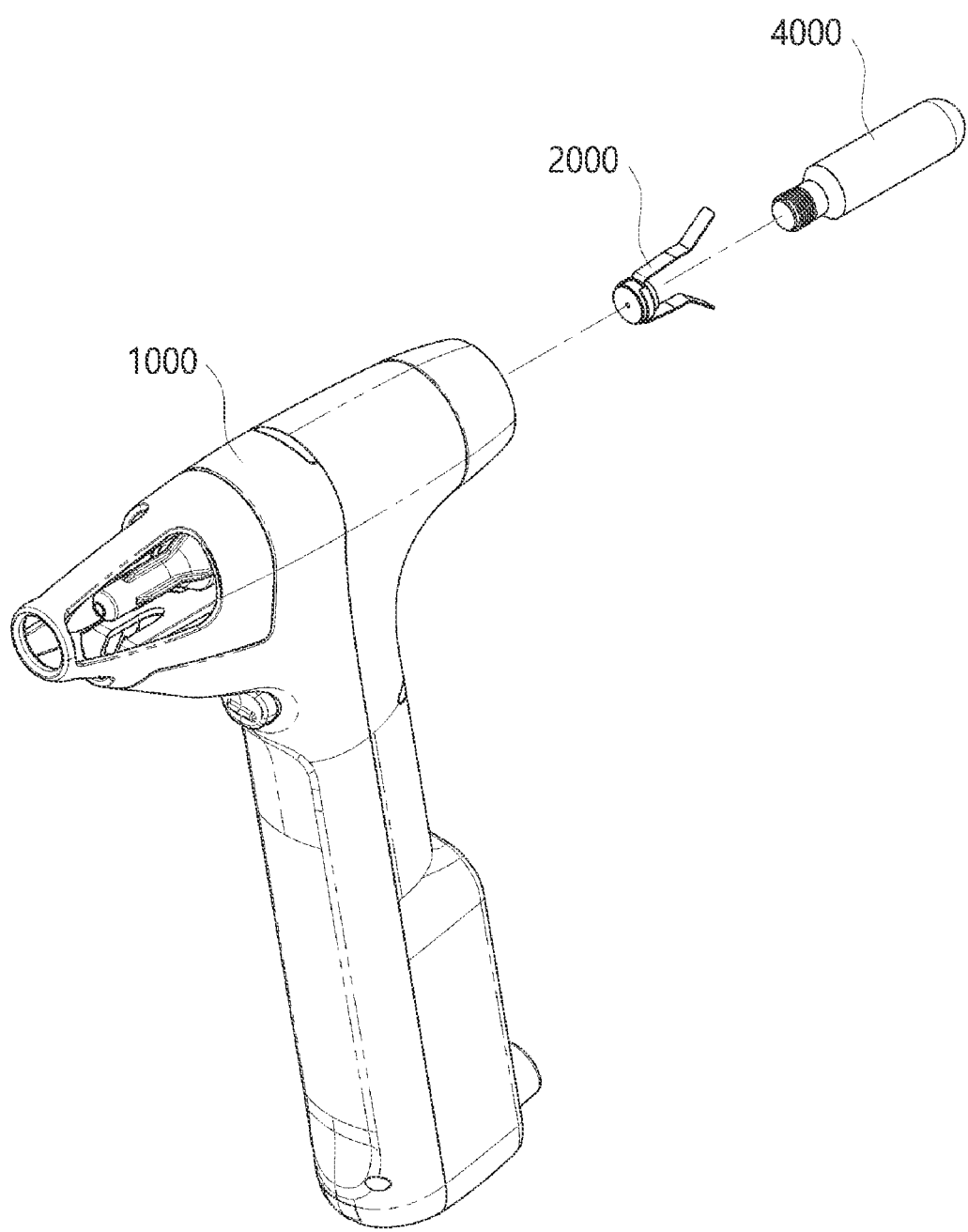
FIGS. 2 and 3 are views illustrating the cooling system (10) according to the embodiment of the present specification. Specifically.
Figure 3:
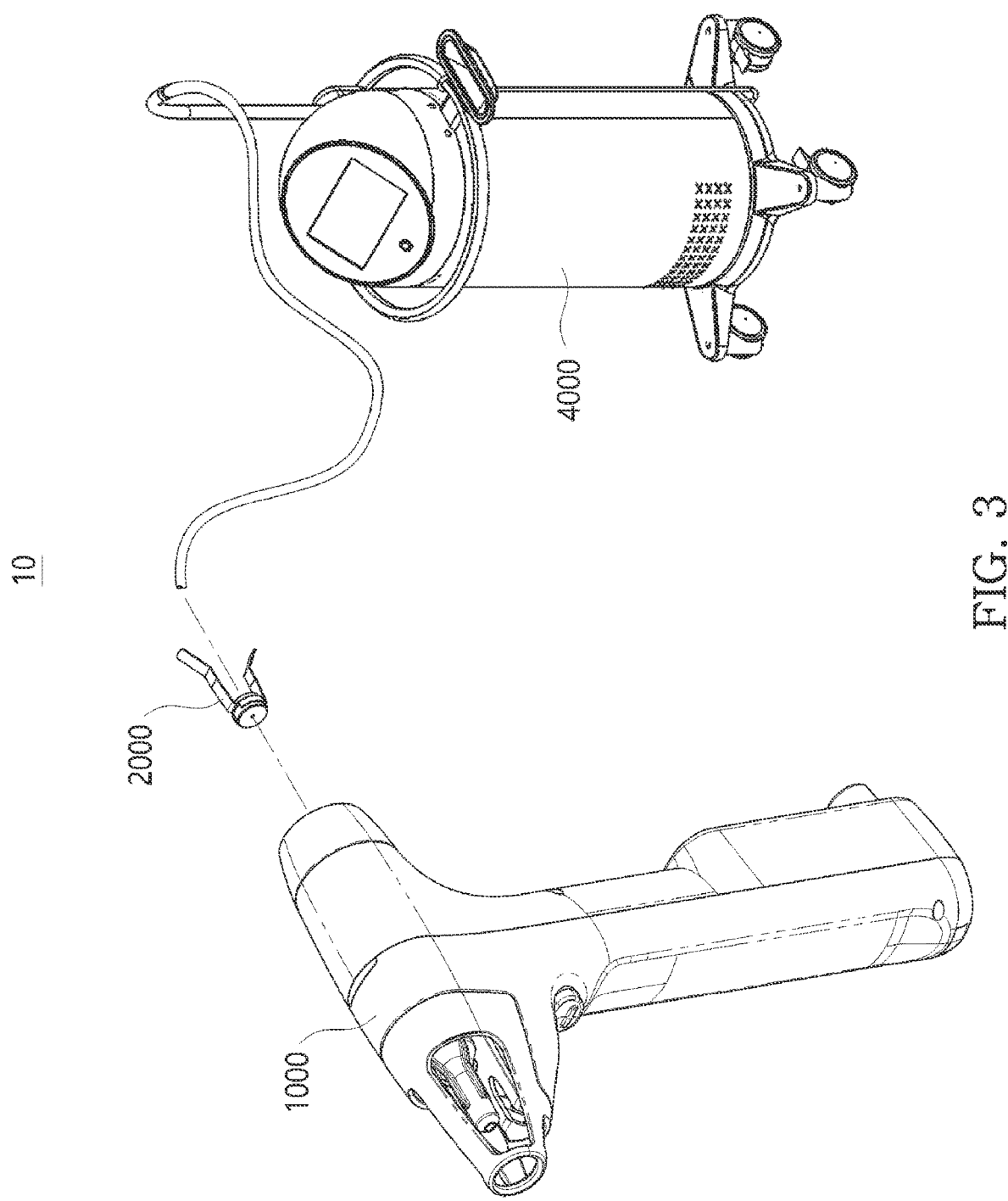

FIGS. 2 to 3 are views illustrating the cooling system 10 according to the embodiment of the present specification. Referring to FIGS. 2 and 3, the cooling system 10 may include the cooling device 1000, the filter fixing module 2000, the stand 3000, and the refrigerant supply unit 4000.

The refrigerant supply unit 4000 may have the form of a cartridge. In this case, the cartridge may be perforated by the perforating member of the filter fixing module such that a refrigerant received in the cartridge can be supplied to the cooling device.

The refrigerant supply unit 4000 may be configured as a cartridge including a plurality of materials or as a plurality of cartridges to deliver substances other than a refrigerant to a targeted area.

Alternatively, the refrigerant supply unit 4000 may have the form of a refrigerant tank. In this case, the refrigerant tank may be connected to a hose so as to supply a refrigerant to the cooling device 1000. In this case, the hose may be screwed to the coupling member of the cooling device 1000 such that a refrigerant received in the refrigerant tank can be supplied to the cooling device 1000.

In addition, when the refrigerant supply unit 4000 has the shape of a refrigerant tank, a refrigerant tank and a hose may be interpreted to mean the refrigerant supply unit 4000.

Meanwhile, when the cooling device 1000 is connected to the refrigerant tank by a hose, the perforating member 2200 of the filter fixing module 2000 may be omitted.

Meanwhile, in order to deliver materials other than a refrigerant to a targeted area, the refrigerant supply unit 4000 may have a plurality of materials included in the refrigerant tank or may have a plurality of refrigerant tanks.

Figure 4:
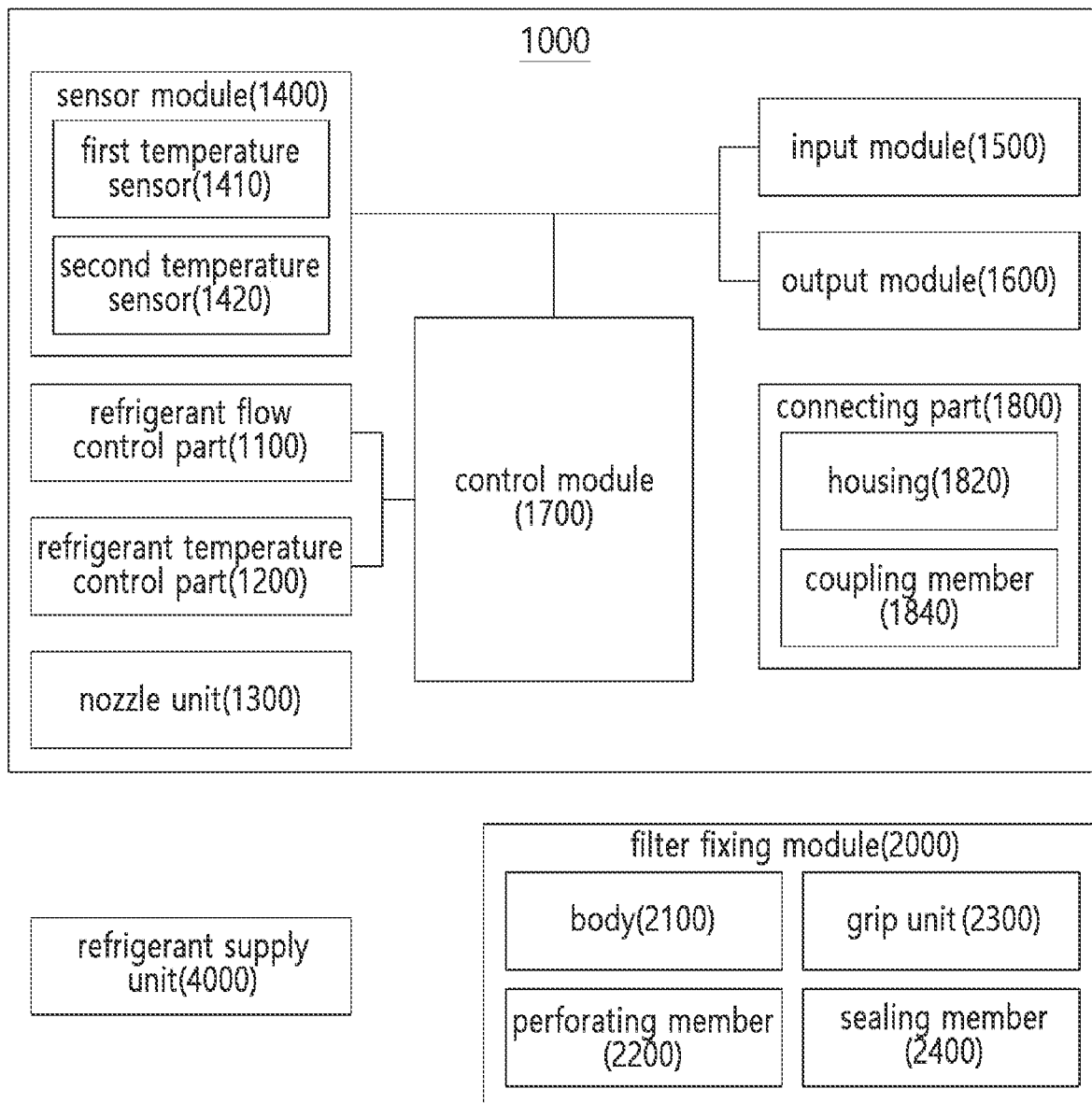
FIG. 4 is a block diagram illustrating the configuration of a cooling device (1000) and a filter fixing module (2000) according to the embodiment of the present specification.

FIG. 4 is a block diagram illustrating the configuration of the cooling device 1000, the filter fixing module 2000, and the refrigerant supply unit 4000 according to the embodiment of the present specification.

Referring to FIG. 4, the cooling device 1000 may include a refrigerant flow control unit 1100, a refrigerant temperature control unit 1200, a nozzle unit 1300, the sensor module 1400, an input module 1500, an output module 1600, the control module 1700, and the connecting unit 1800.

Hereinafter, each component will be described in detail.

According to the embodiment of the present application, the refrigerant flow control unit 1100 may include the valve. The valve may function to control the flow and flow rate of a refrigerant. The valve may function to discharge or block a refrigerant passing through the valve. Alternatively, the valve may function to control the discharged degree of a refrigerant passing through the valve.

The valve according to the embodiment of the present application may be controlled according to a specific signal. The valve may be opened and closed in response to an electronic signal generated by the control module 1700. For a specific example, the valve may be an electronic valve (for example, a solenoid valve) but is not limited thereto.

The valve according to the embodiment of the present application may be controlled according to a mechanical structure and the movement of fluid. The valve may be opened and closed according to pressure generated by fluid moving along a flow path in the cooling device 1000. For a specific example, the valve may be a hydraulic valve (for example, a pressure control valve) but is not limited thereto.

The valve according to the embodiment of the present application may be controlled according to a user's input. The valve may be opened or closed by a user. For a specific example, the valve may be a manual valve (for example, a globe valve) but is not limited thereto.

For example, the valve included in the refrigerant flow control unit 1100 may be located between the inlet of the cooling device 1000 (or referred to as an introduction opening) and the nozzle unit 1300. In this case, the refrigerant flow control unit 1100 may control the amount of a refrigerant supplied from the inlet of the cooling device 1000 to the nozzle unit 1300.

For example, the valve may be located between the inlet of the cooling device 1000 and the nozzle unit 1300, and may control the amount of a refrigerant supplied to the nozzle unit 1300 from the inlet of the cooling device 1000.

Specifically, in the opened state of the valve, a refrigerant may move from the inlet of the cooling device 1000 to the nozzle unit 1300, and in the closed state of the valve, a refrigerant may be restrained from moving to the nozzle unit 1300 from the inlet of the cooling device 1000. In addition, the opening time or opening period of the valve may be controlled to control the amount of a refrigerant which can be moved to the nozzle unit 1300 from the inlet of the cooling device 1000.

For example, the valve may be located between the inlet of the cooling device 1000 located in the connecting unit 1800 of the cooling device 1000 and the refrigerant temperature control unit 1200 to control the amount of a refrigerant supplied to the refrigerant temperature control unit 1200 from the inlet of the cooling device 1000. Specifically, in the opened state of the valve, a refrigerant may be in a state capable of moving to the refrigerant temperature control unit 1200 from the inlet of the cooling device 1000, but in the closed state of the valve, a refrigerant may be in a state of being restricted from moving to the refrigerant temperature control unit 1200 from the inlet of the cooling device 1000. Furthermore, the opening time or opening period of the valve may be controlled such that the amount of a refrigerant movable from the inlet of the cooling device 1000 to the refrigerant temperature control unit 1200 can be controlled.

For another example, the refrigerant flow control unit 1100 may be located between the refrigerant temperature control unit 1200 and the nozzle unit 1300 in the cooling device 1000. In this case, the refrigerant flow control unit 1100 may control the amount of a refrigerant supplied to the nozzle unit 1300 from the refrigerant temperature control unit 1200. For example, the valve may be located between the refrigerant temperature control unit 1200 and the nozzle unit 1300, and may control the amount of a refrigerant supplied from the refrigerant temperature control unit 1200 to the nozzle unit 1300. Specifically, in the opened state of the valve, a refrigerant may be in a state capable of moving to the nozzle unit 1300 from the refrigerant temperature control unit 1200, but in the closed state of the valve, a refrigerant may be in a state of being restricted from moving to the nozzle unit 1300 from the refrigerant temperature control unit 1200. Additionally, the period of opening time or opening period of the valve may be controlled such that the amount of a refrigerant capable of moving to the nozzle unit 1300 from the refrigerant temperature control unit 1200 can be controlled. In other words, the period of opening time of the refrigerant temperature control unit 1200 is controlled such that the amount of a refrigerant supplied to the nozzle unit 1300 can be controlled and the amount of a refrigerant to be sprayed eventually can be controlled, thereby controlling the temperature of the skin surface.

For example, the refrigerant flow control unit 1100 may be embodied as a solenoid valve, and the solenoid valve is electrically connected to the control module 1700 and the input module 1500, and a signal generated when a user manipulates the input module 1500 is input to the control module 1700, and based on this, the control module 1700 controls the solenoid valve to be opened such that the inflow or outflow of a refrigerant can be controlled.

For example, the refrigerant flow control unit 1100 may be embodied as the solenoid valve. In this case, the solenoid valve may control the opening period of the valve by a pulse width modulation (PWM) method according to an electrical signal of the control module 1700 so as to control the inflow or outflow of a refrigerant. Specifically, the solenoid valve automatically performs a plurality of opening and closing operations according to a protocol preset from the control module 1700, so that the valve can be opened only for a predetermined time during a procedure. In this case, the opening period of the valve may be a regular period or an irregular period.

Referring back to FIG. 4, the cooling device 1000 may include the refrigerant temperature control unit 1200. The refrigerant temperature control unit 1200 according to the embodiment of the present application may perform the function of controlling the physical state of a refrigerant. In other words, the refrigerant temperature control unit 1200 may perform the function of controlling the physical state of a refrigerant inside the cooling device 1000. That is, the refrigerant temperature control unit 1200 may perform the function of controlling the physical state of a refrigerant moving in the cooling device 1000.

For example, the refrigerant temperature control unit 1200 may control the temperature of a refrigerant. The refrigerant temperature control unit 1200 may heat a refrigerant. Alternatively, the refrigerant temperature control unit 1200 may cool a refrigerant. Alternatively, the refrigerant temperature control unit 1200 may maintain the temperature of a refrigerant by heating and/or cooling the refrigerant according to the state of the refrigerant.

For example, the refrigerant temperature control unit 1200 may be disposed between the refrigerant flow control unit 1100 and the nozzle unit 1300. For example, the refrigerant temperature control unit 1200 may be disposed between the refrigerant flow control unit 1100 and the connecting unit 1800. However, in order to maintain the temperature of a target at a predetermined temperature by spraying a refrigerant to the target, the refrigerant temperature control unit 1200 may be more advantageously disposed between the refrigerant flow control unit 1100 and the nozzle unit 1300.

The refrigerant temperature control unit 1200 according to the embodiment of the present application may include a temperature control member capable of generating thermal energy.

The temperature control member may be embodied in various forms.

For example, the temperature control member may include a thermoelement using a Peltier effect which receives current to absorb heat on a first surface and discharge heat on a second surface according to the direction of the received current. In a case in which the refrigerant temperature control unit 1200 includes the thermoelement, when current is applied to the thermoelement, due to the Peltier effect, the first surface of the thermoelement may generate thermal energy, and the second surface of the thermoelement may generate cooling energy.

According to the embodiment of the present application, the cooling device 1000 disposed to be in thermal contact with a flow path in which a refrigerant moves may be provided on a surface corresponding to the first surface the thermoelement. In this case, the thermoelement may function as the refrigerant temperature control unit 1200.

The refrigerant temperature control unit 1200 may generate thermal energy by using chemical energy or by using electrical energy. Additionally, the refrigerant temperature control unit 1200 may generate thermal energy by using a Joule-Thomson method using condensed gas.

For example, the temperature control member may include a device or element using a thermodynamic cycle such as a Stirling cooler or vapor compression refrigeration cycle, or the Joule-Thomson method using expansion gas.

For another example, the temperature control member may produce or provide cooling energy by using a refrigerant such as carbon dioxide or liquid nitrogen.

The temperature control member may be thermally coupled to a flow path through which a refrigerant in the cooling device 1000 flows. For example, the temperature control member may be in surface contact with at least a portion of the flow path through which a refrigerant flows to provide cooling energy or thermal energy thereto.

Hereinafter, for convenience of explanation, a case in which the temperature control member is a thermoelement using the Peltier effect is mainly described, but the technical idea of the present specification is not limited thereto.

Referring back to FIG. 4, the cooling device 1000 according to the embodiment of the present application may include the nozzle unit 1300. In this case, the nozzle unit 1300 may perform the function of spraying a refrigerant flowing in the cooling device 1000 to the outside. The nozzle unit 1300 may perform the function of discharging a refrigerant passing through the refrigerant flow control unit 1100 and/or the refrigerant temperature control unit 1200 to the outside.

The nozzle unit 1300 according to the embodiment of the present application may be embodied as any suitable type of a nozzle. The nozzle may function to spray a refrigerant such that the refrigerant flowing in at least one area inside the cooling device 1000 is discharged to a free space to reach a targeted area of the skin surface. Additionally, the nozzle unit 1300 may be embodied to include a structure of a nozzle that can optimize a Joule-Thomson effect. Specifically, the nozzle unit is formed to have a nozzle narrower in width than a flow path in which a refrigerant of high pressure flows. As the flow path is opened, the refrigerant of high pressure is guided to the nozzle along the flow path, and the refrigerant discharged through the nozzle is sprayed in a cooled state by the Joule-Thomson effect.

The refrigerant sprayed through the nozzle unit 1300 may be sprayed in a cooled state by the Joule-Thomson effect. Here, the Joule-Thomson effect is a phenomenon in which the temperature of a compressed gas decreases when the gas expands. The Joule-Thomson effect indicates a temperature change in relation to a thermodynamic phase consisting of pressure and temperature, and is a phenomenon applied to liquefying air or cooling the air through a refrigerant. When an aperture such as an orifice is inserted into the flow path of fluid, the temperature of the fluid decreases behind the aperture. The Joule-Thomson effect is a phenomenon in which internal energy hardly changes during free expansion of gas, that is, during adiabatic expansion of gas without exchanging work with the outside, and refers to the effect of causing adiabatic free expansion of gas to obtain a low temperature by a gas liquefaction device. When with the Joule-Thomson effect, a refrigerant sprayed through the nozzle unit 1300 is cooled by a sudden pressure drop and is sprayed on an area to be treated, the refrigerant may be in contact with the area to be treated and may take away heat of the area to be treated such that the area to be treated can be cooled.

In addition, the nozzle may have wear-resistant properties. In other words, the nozzle may be formed of a material that is less damaged due to friction. For example, the nozzle may be made of an aluminum alloy, a steel alloy, stainless steel or a copper alloy, but is not limited thereto.

Furthermore, according to the embodiment of the present application, the nozzle unit 1300 may include a guide unit 1310 such that a refrigerant discharged from the nozzle unit 1300 is limited to a targeted area present on the skin surface.

Meanwhile, the guide unit 1310 may have a form in which a refrigerant flowing sideways after discharged from the nozzle unit 1300 and reaching a targeted area in the form of an impinged jet can be confined in a predetermined area. For example, a surface in contact with the targeted area of the guide unit 1310 may have a circular or polygonal shape, or circular or polygonal shape having discrete points.

In this case, the guide unit 1310 may control the temperature of the targeted area to be even by confining a refrigerant in a predetermined area, and after cooling the targeted area, the refrigerant may be discharged through a hole provided in the back side to the outside.

Referring back to FIG. 4, the cooling device 1000 according to the embodiment of the present application may include the sensor module 1400. The sensor module 1400 may detect the temperature of a targeted area of the skin surface and/or the physical characteristics of the cooling device 1000.

For example, the sensor module 1400 may detect the temperature of a targeted area. For example, the sensor module 1400 may include at least one temperature sensor 1410 or 1420, and the at least one temperature sensor 1410 or 1420 may measure the temperature of the targeted area of the skin surface. The at least one temperature sensor 1410 or 1420 of the sensor module 1400 may be composed of a non-contact temperature sensor using infrared light, and a contact temperature sensor such as a thermocouple, a resistance temperature detector (RTD), a thermistor, an IC temperature sensor, or an ultrasonic temperature sensor.

For another example, the sensor module 1400 may detect physical characteristics of components included in the cooling device 1000. For example, the sensor module 1400 may measure electrical characteristics such as a current or voltage applied to the refrigerant temperature control unit 1200. In this case, the sensor module 1400 may include an analog or electronic circuit for measuring electrical characteristics such as a current or voltage.

The sensor module 1400 may provide the detected temperature of a targeted area and/or physical characteristics of the cooling device 1000 to the control module 1700. For example, the sensor module 1400 may provide the control module 1700 with a signal indicating a real-time temperature value of a targeted area and a current or voltage value applied to the refrigerant temperature control unit 1200.

The input module 1500 may receive a user's input from the user. The user's input may be performed in various forms including button input, key input, touch input, rotation input, or voice input. For example, the input module 1500 includes a button which a user can press, a wheel switch which a user can turn, a touch sensor which detects a user's touch, a microphone which receives a user's voice input, and various types of input means which detects or receives a user's input.

The output module 1600 may output various kinds of information and provide the information to a user. The output module 1600 includes the cooling state of the cooling device, a display which outputs information related to the real-time temperature of a targeted area, a speaker which outputs sound, a haptic device which generates vibration, and various other types of output means.

The control module 1700 may control the overall operation of the cooling device 1000. For example, the control module 1700 may load and execute a program for the operation of the refrigerant flow control unit 1100. For another example, the control module 1700 may control the amount of a current (or a voltage) applied to the refrigerant temperature control unit 1200 to control thermal energy transmitted to a refrigerant, may control the input module 1500 and the output module 1600 to generate and transmit control signals according to a user's input, or may provide specific information to a user.

Here, the control module 1700 may be embodied as a device such as a central processing unit (CPU), a microprocessor, a processor core, a multiprocessor, an application-specific integrated circuit (ASIC), and a field programmable gate array (FPGA) according to hardware or software or a combination thereof. The control module 1700 may be provided in the form of an electronic circuit that performs a control function by processing electrical signals in hardware, and may be provided in the form of a program or code that drives the hardware circuit in software.

Meanwhile, although not shown in FIG. 4, the cooling device 1000 may further include a memory in which a control program loaded or executed in the control module 1700 is stored, and a power supply unit that supplies power required for the operation of the cooling device 1000.

The connecting unit 1800 may be provided to connect the refrigerant supply unit 4000 to the cooling device 1000.

Specifically, the connecting unit 1800 may include at least a portion of the refrigerant supply unit 4000 and/or a housing 1820 for receiving the filter fixing module 2000.

In addition, the connecting unit 1800 may include the coupling member 1840 for mounting the refrigerant supply unit 4000 and/or the filter fixing module 2000.

For example, the coupling member 1840 may be provided as a structure including threads. For example, the coupling member 1840 may be a member including threads composed of crests and roots. Here, the threads of the coupling member 1840 are engaged with the threads of the refrigerant supply unit 4000 such that the refrigerant supply unit 4000 can be connected to the cooling device 1000.

For example, the coupling member 1840 may include a thread structure including at least one groove. For example, the filter fixing module 2000 to be described later may be disposed between the connecting unit 1800 of the cooling device 1000 and the refrigerant supply unit 4000. The filter fixing module 2000 may include the grip unit 2300, and the threads of the coupling member 1840 may include a groove formed in a shape corresponding to the shape of the grip unit.

In this case, the refrigerant supply unit 4000 may be perforated by the perforating member 2200 of the filter fixing module 2000, and the grip unit 2300 of the filter fixing module 2000 may be fitted into the groove of the coupling member 1840. Through such a connection structure, a refrigerant discharged from the refrigerant supply unit 4000 may be introduced through the connecting unit 1800 into the cooling device 1000.

Through the structure of the connecting unit 1800 described above, the filter fixing module 2000 according to the embodiment of the present specification may be received in the coupling member 1840 of the connecting unit 1800, and the refrigerant supply unit 4000 may be screwed to the coupling member 1840 of the connecting unit 1800 and may be perforated by the filter fixing module 2000. Accordingly, according to the embodiment of the present specification, the filter fixing module 2000 may function to perforate the refrigerant supply unit 4000 and may function to allow the filter to be received in a path in which a refrigerant flows. Furthermore, for ease of the use of the filter fixing module 2000, the filter fixing module 2000 may include the grip unit 2300 protruding to the outside of the connecting unit 1800, and accordingly, a user may easily mount the filter fixing module 2000 to the cooling device 1000 or may easily remove the filter fixing module 2000 from the cooling device 1000. This will be described later in more detail with reference to FIGS. 9 to 18.

The filter fixing module 2000 may include the body 2100, the perforating member 2200, the grip unit 2300, and the sealing member 2400.

The body 2100 may have the support surface supporting the filter. Additionally, the body 2100 may have the receiving surface which receives the filter and at least a portion of the sealing member and is connected to the support surface. The body 2100 may be formed into a variety of structures to locate the filter in the filter fixing module 2000.

In addition, the filter fixing module 2000 may be located between the refrigerant supply unit 4000 and the cooling device 1000, and the filter may be located in a path through which a refrigerant discharged from the refrigerant supply unit 4000 is introduced into the inlet of the cooling device 1000. Accordingly, after impurities included in a refrigerant are removed through the filter fixing module 2000, the refrigerant may be introduced into the cooling device 1000. Accordingly, the cooling system 10 according to the embodiment of the present application may be provided to minimize the possibility that a targeted area is contaminated by impurities included in a refrigerant.

The perforating member 2200 may have a body in which the hollow hole is formed so that the perforating member 2200 performs the function of the flow path of a refrigerant discharged from the refrigerant supply unit 4000. The perforating member 2200 may have the first end part adjacent to the support surface of the body 2100, the second end part perforating the refrigerant discharge hole of the refrigerant supply unit 4000, and the body extending from the first end part to the second end part. In this case, the perforating member 2200 may receive a refrigerant through the second end part from the refrigerant supply unit 4000, and the refrigerant may be discharged through the first end part toward the cooling device 1000.

The grip unit 2300 may include the at least one grip member 2310 or 2320. The at least one grip member 2310 or 2320 may be fitted into at least one groove included in the threads of the coupling member 1840.

For example, the grip unit 2300 may include the two grip members 2310 and 2320. In this case, the threads of the coupling member 1840 may include two grooved members, and the two grip members 2310 and 2320 may be received respectively in the two grooved members included in the threads.

For example, the grip unit 2300 may include four grip members. In this case, the threads of the coupling member 1840 may include four grooved members, and the four grip members may be received respectively in the four grooved members included in the threads.

In this case, each of the grip members and the grooved members of the threads of the coupling member 1840 described above may be formed as a symmetric structure relative to a central axis. Alternatively, each of the grip members and the grooved members of the threads of the coupling member 1840 described above may be formed as an asymmetric structure relative to the central axis.

Through the above-described structure, the filter fixing module 2000 may be mounted to the connecting unit 1800 of the cooling device 1000.

However, the above-described structure is merely an example, and the grip unit 2300 may be provided as various structures capable of being connected to the coupling member 1840.

In a state in which at least one grip member 2310 or 2320 is mounted to the connecting unit 1800 of the cooling device 1000, the at least one grip member 2310 or 2320 may be provided to protrude to the outside of the cooling device 1000. Accordingly, a user may easily apply force to the at least one grip member 2310 or 2320 protruding to the outside of the cooling device 1000, and may easily remove the at least one grip member 2310 or 2320 from the grooved member formed in the threads of the coupling member 1840. For example, when a user applies force in a direction in which each of the grip members 2310 and 2320 approaches each other, the grip members 2310 and 2320 may be removed from the grooved members, respectively, formed in the threads of the coupling member 1840.

Due to the above-described structure, after completing the use of the refrigerant supply unit 4000 (e.g., a cartridge or refrigerant tank), a user may apply force to the at least one grip member 2310 or 2320 and may easily remove the filter fixing module 2000 from the cooling device 1000.

Meanwhile, when the use of the refrigerant supply unit 4000, (e.g., a cartridge or a refrigerant tank) is completed, gaseous refrigerant may remain in the refrigerant supply unit. When the gaseous refrigerant is exposed to atmospheric pressure, the gaseous refrigerant may expand instantaneously and generate noise, and thus may cause inconvenience to a user.

According to the cooling system 10 according to the embodiment of the present application, as described above, when the use of the refrigerant supply unit 4000 is completed, a user may remove the refrigerant supply unit 4000 from the coupling member 1840. For example, a user may rotate the refrigerant supply unit 4000 having the shape of a cartridge in one direction such that the engagement of the threads of the cartridge with the threads of the coupling member 1840 is released. In this case, as the refrigerant supply unit 4000 is removed from the coupling member 1840, a fluid passage may be formed inside the coupling member 1840. In this case, a gaseous refrigerant remaining in the refrigerant supply unit 4000 (for example, a cartridge or a refrigerant tank) leaks through the fluid passage, thereby minimizing a user's inconvenience which may occur due to exposure of the gaseous refrigerant to atmospheric pressure.

Meanwhile, the user may apply force to the at least one grip member 2310 or 2320 to remove the at least one grip member 2310 or 2320 from grooves formed in the threads of the coupling member 1840.

The filter fixing module 2000 may include the sealing member 2400 which prevents the leakage of a refrigerant introduced into the filter fixing module 2000 through the perforating member 2200.

In this case, the filter fixing module 2000 may include the first sealing member 2410 received in the receiving surface extending in the first direction relative to the body 2100, and the second sealing member 2420 through which the perforating member 2200 passes, the perforating member 2200 extending in the second direction which is a direction opposite to the first direction relative to the body.

The first sealing member 2410 may perform the function of decreasing the leakage of a refrigerant flowing to the cooling device 1000 from the filter fixing module 2000.

The second sealing member 2420 may function to decrease the leakage of a refrigerant, to be supplied to the hollow hole of the perforating member 2200 of the filter fixing module 2000 from the refrigerant supply unit 4000, to the outer surface of the perforating member 2200.

Meanwhile, the first sealing member 2410 may include the hollow hole through which a refrigerant can flow. For example, the hollow hole constituting a passage through which a refrigerant can flow may be formed in the center part of the first sealing member 2410.

The second sealing member 2420 may include the through hole through which the perforating member 2200 can pass. For example, the through hole through which the body of the perforating member 2200 can pass may be formed in the center part of the second sealing member 2420, and the shape and size of the through hole may correspond to the shape and size of the body of the perforating member. For example, the inner diameter of the second sealing member 2420 defined by the through hole may be larger than the outer diameter of the perforating member 2200.

The filter fixing module 2000 according to the embodiment of the present application may be compatible with both the refrigerant supply unit 4000 in the form of a cartridge and the refrigerant supply unit 4000 in the form of a refrigerant tank. For example, the perforating member 2200 of the filter fixing module 2000 may be provided to perforate a cartridge or a hose connected to a refrigerant tank.

The structure and shape of the filter fixing module 2000 will be described later in detail with reference to FIGS. 9 to 18.

Hereinafter, referring to FIG. 5, a process in which the cooling system 10 according to the embodiment of the present specification cools a target will be described in detail.

Figure 5:
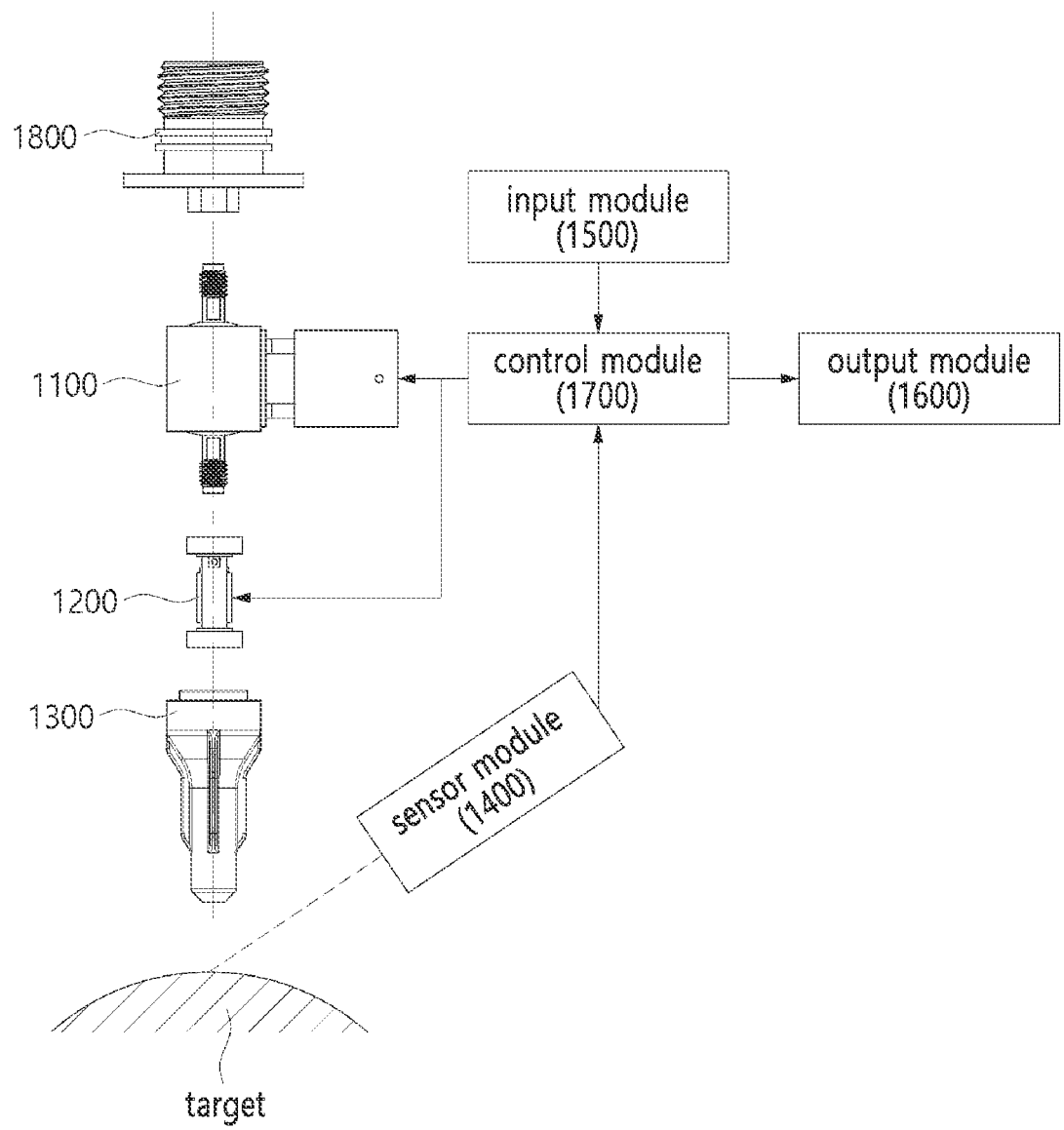
FIG. 5 is a view illustrating the process of cooling a target through the cooling system (10) according to the embodiment of the present specification.

FIG. 5 is a view illustrating the process of cooling a target through the cooling system 10 according to the embodiment of the present specification.

The control module 1700 may control whether to spray a refrigerant or the spray amount of a refrigerant which is introduced into the cooling device 1000 through the refrigerant moving hole formed inside the connecting unit 1800.

For example, the control module 1700 may control the refrigerant flow control unit 1100 to control whether to spray a refrigerant and/or the amount of a refrigerant to be sprayed.

In addition, the control module 1700 may control the refrigerant temperature control unit 1200 to control the temperature of a refrigerant flowing in the cooling device 1000. Through this, the cooling device 1000 may spray a refrigerant having the characteristic of a controlled temperature to a target on the skin surface through the nozzle unit 1300 to supply cooling energy to the target such that the target can be cooled.

Hereinafter, a process in which a cooling function is performed will be described in detail.

The control module 1700 may control the temperature control member of the refrigerant temperature control unit 1200 to provide thermal energy to a refrigerant flowing through the tube of the refrigerant temperature control unit 1200 such that the temperature of the refrigerant reaches a preset temperature. For example, the control module 1700 may control a current (or a voltage) value applied to the temperature control member of the refrigerant temperature control unit 1200 to increase/decrease or maintain thermal energy applied to a refrigerant such that the temperature of the refrigerant can be controlled. Additionally, the cooling system 10 according to the embodiment of the present application may control the temperature of a refrigerant to be sprayed, and finally, may control the temperature of a target to reach a preset temperature.

The sensor module 1400 may measure the temperature of a target changing according to cooling energy transmitted to the target due to a refrigerant so as to obtain temperature information, and may transmit the obtained temperature information to the control module 1700.

Meanwhile, temperature information obtained by the sensor module 1400 may include information about the temperature of components (e.g., the temperature control member of the refrigerant temperature control unit 1200, etc.) provided in the cooling device 1000, or information about the ambient temperature of the cooling device 1000. Here, the sensor module 1400 may include a plurality of sensors to obtain various kinds of temperature information.

The control module 1700 generate a control signal to control a current applied to the temperature control member of the refrigerant temperature control unit 1200 based on temperature information obtained by the sensor module 1400.

For example, the control module 1700 may use the temperature information of a target obtained by the sensor module 1400 to use the feedback control of controlling power applied to the temperature control member of the refrigerant temperature control unit 1200. Specifically, the control module 1700 may control the temperature of a target by using the following proportional integral differential (PID) control equation.

$$P(t) = C_p \text{error}(t) + C_i \int_0^t \text{error}(t) dt + C_d \frac{d(\text{error}(t))}{dt}$$

Here, P(t) means the output value or control value of a signal by which the control module 1700 controls the temperature control member, error(t) means a difference value between the temperature of a target to be controlled by the control module 1700 and the temperature of a target measured by the sensor module 1400, and Cp, Ci, and Cd may mean a gain value or a gain selected in a tuning process. Meanwhile, in the above control equation, with each term omitted, P, PI, and PD control may be used.

For another example, in consideration of the type of a refrigerant and a contact area between the temperature control member of the refrigerant temperature control unit 1200 and the refrigerant flow path, etc., the control module 1700 may provide the temperature control member with power corresponding to the specific temperature (or the temperature of the refrigerant) of a target to be controlled.

The input module 1500 may obtain a user's input for presetting a cooling time and the control temperature of a target (or the control temperature of a refrigerant), and the like. For example, a user may preset the spray time of a refrigerant through the input module 1500 to preset time for which a refrigerant is sprayed to a target. For another example, a user may preset the temperature of a target to be controlled through the input module 1500.

The input module 1500, which has obtained a user's input, may transmit a user's input information related to the cooling time and/or the control temperature for a target to the control module 1700, and based on the input information, the control module 1700 may control a current (or a voltage) value applied to the temperature control member of the refrigerant temperature control unit 1200 or whether to open/close the valve of the refrigerant flow control unit 1100 and opening/closing time of the valve, etc.

Meanwhile, the input module 1500 may obtain an input instructing the initiation of cooling in addition to the input information related to a cooling condition including the cooling time and the control temperature of a target, etc. For example, when input of the input information related to the cooling condition described above is completed, a user may perform an input instructing the initiation of cooling through the input module 1500. In this case, the input module 1500 may be embodied to transmit an input signal instructing the initiation of cooling to the control module 1700, and the control module 1700 may be embodied to control the opening/closing of the valve of the refrigerant flow control unit 1100 or to control a current (or a voltage) value applied to the temperature control member of the refrigerant temperature control unit 1200 in response to a user's input instructing the initiation of cooling.

In this case, the input information related to the cooling condition and the input information in which the initiation of cooling is instructed may be configured to be obtained through input modules 1500 different from each other. For example, input information related to the cooling condition is obtained through a first input module 1510, and the input information related to the cooling condition may be embodied to be obtained through a second input module 1520 separate from the first input module 1510.

However, the above description is only an example, and the input module is not limited thereto and may be provided such that the input information related to the cooling condition and the input information instructing the initiation of cooling are obtained through a single input module.

An operation related to the input module will be described later in detail with reference to FIGS. 20 and 21.

The output module 1600 may output various kinds of information related to the cooling device 1000 and provide the information to a user.

For example, the output module 1600 may output the real-time temperature information of a targeted area through a display. Specifically, the sensor module 1400 may measure temperature information of a target and may transmit the measured temperature information of a target to the control module 1700. In this case, the control module 1700 may transmit the temperature information of a target to the output module 1600, and the output module 1600 may be configured to output the temperature information of the targeted area based on the obtained temperature information of a target.

The output module 1600 may output information related to the state of the cooling device 1000 and provide the information to a user.

For example, the control module 1700 may determine whether the first temperature sensor 1410 and the second temperature sensor 1420 are normal based on temperature information obtained from a first temperature sensor 1410 and a second temperature sensor 1420. In this case, the control module 1700 may, through the output module 1600, provide a user with the result of determining whether the first temperature sensor 1410 and the second temperature sensor 1420 are normal. For example, when it is determined that the first temperature sensor 1410 and the second temperature sensor 1420 operate normally, a first alarm may be output through the output module 1600 in the form of a speaker, and when it is determined that at least one of the first temperature sensor 1410 and the second temperature sensor 1420 does not operate normally, a second alarm may be output through the output module 1600 in the form of a speaker.

However, the above is merely an example, and any appropriate information related to the operation of the cooling device 1000 may be provided to a user through the output module 1600 in any form.

An operation related to the output module 1600 will be described later in detail with reference to FIGS. 27 to 28.

Hereinafter, the structure of the cooling device 1000 will be described with reference to FIGS. 6 to 8.

Figure 6:
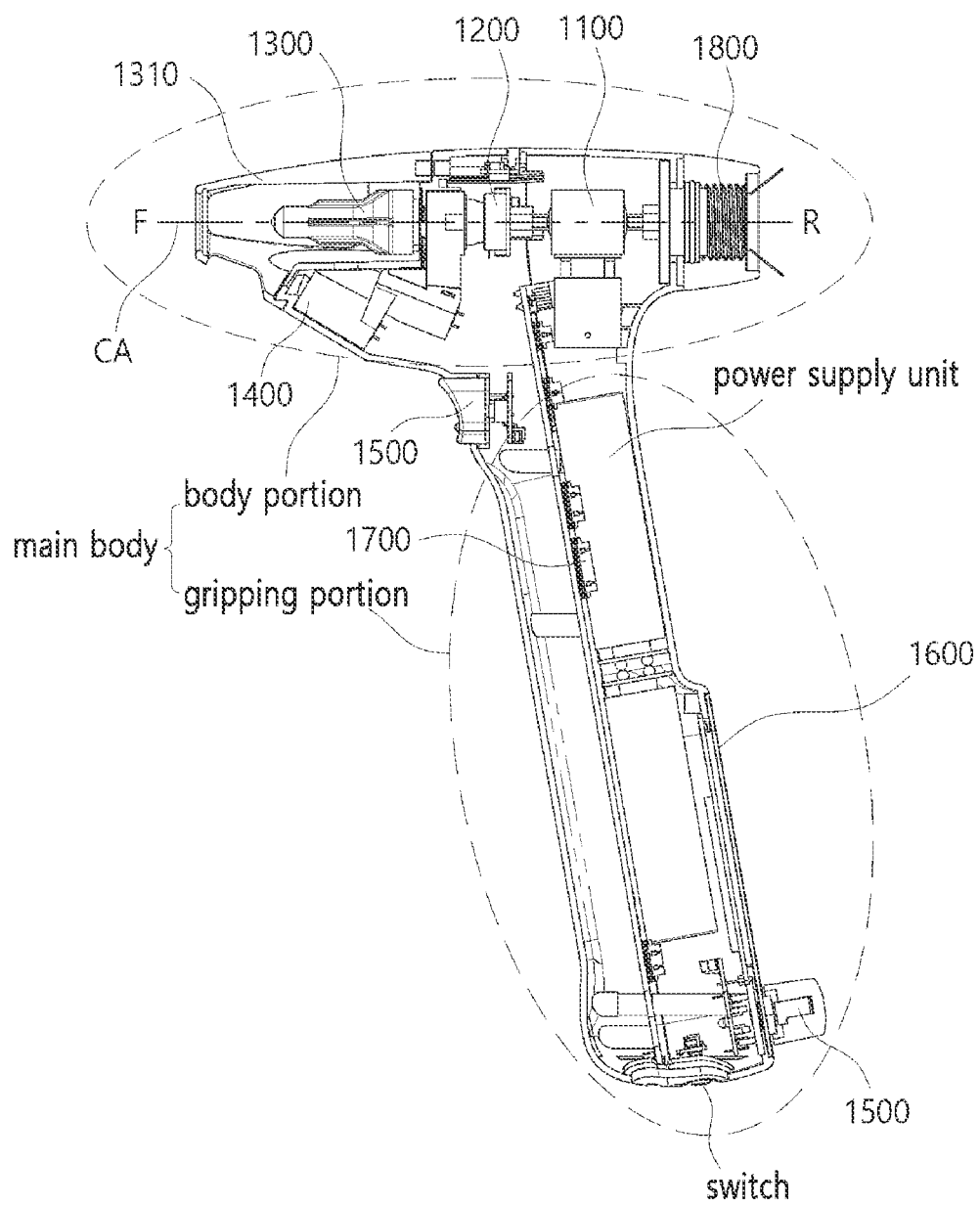
FIG. 6 is a view illustrating the internal structure of the cooling device (1000) according to the embodiment of the present specification.

FIG. 6 is a view illustrating the internal structure of the cooling device 1000 according to the embodiment of the present specification. Referring to FIG. 6, the cooling device 1000 may include the main body composed of a body portion and a gripping portion, and components of the cooling device 1000 described above may be disposed in the body portion or the gripping portion.

The main body of the cooling device 1000 may be divided into the body portion and the gripping portion. For example, the main body of the cooling device 1000 may include the body portion to which the filter fixing module 2000 and the refrigerant supply unit 4000 are mounted, and the gripping portion which can be grasped by a user. Here, the body portion and the gripping portion may constitute the cooling device 1000 in such a manner that the body portion and the gripping portion are integrated with each other or are coupled to each other by assembly although separated physically from each other.

The refrigerant flow control unit 1100, the refrigerant temperature control unit 1200, the nozzle unit 1300, the sensor module 1400, and the connecting unit 1800 may be disposed inside the body portion. Specifically, the refrigerant flow control unit 1100, the refrigerant temperature control unit 1200, the nozzle unit 1300, the sensor module 1400, and the connecting unit 1800 may be disposed inside the body portion relative to the central axis CA of the body portion. For example, the refrigerant temperature control unit 1200, the nozzle unit 1300, and the sensor module 1400 may be disposed close to the front end F of the body portion, and the refrigerant flow control unit 1100 and the connecting unit 1800 may be disposed close to the rear end R of the body portion.

Meanwhile, the input module 1500 and the output module 1600 may be further disposed in the body portion. In this case, the input module 1500 may include a plurality of input devices, and each of the input devices may be disposed close to the front end F or rear end R of the body portion. Additionally, the output module 1600 may include a plurality of output devices and each of the output devices may be disposed close to the front end F or rear end R of the body portion.

Here, the central axis CA may refer to an axis formed in the longitudinal direction of the body portion passing through the center of the body portion or may refer to an axis parallel thereto.

Here, the connecting unit 1800 may constitute at least a portion of the main body. For example, the connecting unit 1800 may be formed on the rear end R of the body portion of the cooling device 1000. Alternatively, the connecting unit 1800 may be embodied by being coupled to the body portion.

Here, the filter fixing module 2000 may be mounted to the main body. For example, in the rear end R of the body portion, the grip member 2310 or 2320 of the filter fixing module 2000 may be mounted to or removed from the cooling device 1000. For example, the grip member 2310 or 2320 may be mounted to or removed from the cooling device 1000 through the connecting unit 1800 formed on the rear end R of the body portion. Specifically, the grip member 2310 or 2320 may be mounted to or removed from the cooling device 1000 through at least one groove formed in the threads of the connecting unit 1800 formed on the rear end R of the body portion.

The control module 1700 may be disposed inside the gripping portion. For example, referring back to FIG. 6, the control module 1700 may be disposed along the longitudinal direction of the gripping portion inside the gripping portion.

In addition, the input module 1500 may be disposed on the inside or outside of the gripping portion.

For example, the input module 1500 such as a button for instructing cooling initiation may be disposed on a part at which a user's fingers are located when the user grasps the gripping portion. Accordingly, a user may press the button while grasping the cooling device 1000 to instruct the initiation of cooling, thereby easily controlling the operation of the cooling device 1000.

For another example, the input module 1500 such as a wheel switch or a button, etc. for presetting a cooling condition such as the cooling time and the control temperature of a target may be disposed on the outside of the gripping portion (e.g., the outside of the end of the gripping portion). Accordingly, a user may easily preset the cooling condition before the initiation of cooling.

In addition, the output module 1600 may be disposed on the inside or outside the gripping portion.

For example, the output module 1600 such as a display indicating the state of a cooling operation (e.g., temperature information of a target and a remaining time of a cooling operation, etc.) may be disposed on the part of the gripping portion (e.g., the rear surface of the gripping portion) located in a user's field of view during the use of the cooling device 1000. Accordingly, a user may easily obtain information on a cooling state (e.g., a real-time target temperature and a remaining cooling time, etc.) while performing the cooling operation by using the cooling device 1000.

Furthermore, a switch for controlling whether to operate the cooling device, a power supply unit for supplying power to the cooling device 1000, any suitable heat dissipation member such as a blower for dissipating heat generated from the power supply unit, and a charging port may be disposed in the gripping portion.

Meanwhile, the arrangement of components inside the body portion and gripping portion of the cooling device 1000 is not limited to the above description.

Figure 7:
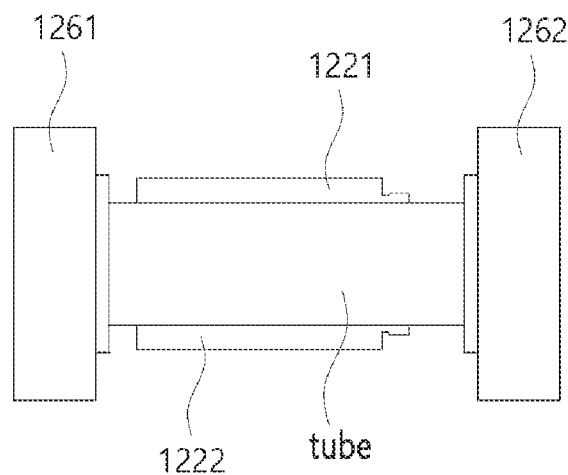
FIG. 7 is a view illustrating a refrigerant temperature control unit (1200) according to the embodiment of the present specification.

FIG. 7 is a view illustrating the refrigerant temperature control unit 1200 according to the embodiment of the present specification.

Referring to FIG. 7, the refrigerant temperature control unit 1200 may include the temperature control member 1220, a porous member 1240, an insulation member 1260, and a tube.

The tube may be thermally coupled to the temperature control member 1220. For example, the tube may include the first surface in contact with a surface of the first temperature control member 1221, and the second surface in contact with a surface of the second temperature control member 1222. The tube may receive thermal energy from the first and second temperature control members 1221 and 1222 through the first surface and the second surface. In this case, a tube illustrated in FIG. 7 may be a tube integrated with a tube having the inlet 1110 illustrated in FIG. 10. Alternatively, the tube illustrated in FIG. 7 may be a tube separate from the tube having the inlet 1110 illustrated in FIG. 10 to be connected to each other.

In this case, the tube and the temperature control member 1220 may be configured in shapes in which thermal energy or cooling energy is efficiently transferred. For example, at least a portion of the tube and the temperature control member 1220 may be embodied in rectangular parallelepiped shapes in order to be in surface contact with each other. Meanwhile, the shapes of the tube and the temperature control member 1220 are not limited to the above-described rectangular parallelepiped shapes, and may be embodied in various shapes to be in surface contact with each other.

Furthermore, the first temperature control member 1221 and the second temperature control member 1222 may be fixed to the tube while in surface contact with the tube.

Here, the temperature control member 1220 may include a first surface and a second surface that absorb or generate heat according to the direction of an applied current. In this case, preferably, the first surface of the temperature control member 1220 in surface contact with the tube may be configured as a surface which generates heat according to the direction of an applied current, and the second surface of the temperature control member 1220 may be configured as a surface which absorbs heat such that the second surface is thermally coupled fixedly to the tube. In this case, the temperature control member 1220 may transmit thermal energy to a refrigerant flowing in the tube through the first surface.

Meanwhile, the porous member 1240 may be disposed inside the tube. The porous member 1240 disposed inside the tube may transmit thermal energy transmitted through the tube from the temperature control member 1220 to a refrigerant. Here, the porous member 1240 may have a porous structure including a plurality of pores and may have an increased contact surface with a refrigerant due to the porous structure, and thus may function to more efficiently transmit thermal energy to a refrigerant passing through the plurality of pores.

The insulation member 1260 may be disposed on a periphery of each of the first and second sides of the tube of the refrigerant temperature control unit 1200.

Referring back to FIG. 7, a first insulation member 1261 may be disposed and fixed between the nozzle unit 1300 and a first side of the tube located on the side of the nozzle unit 1300. Through this, the first insulation member 1261 may thermally insulate external components including the nozzle unit 1300 from the refrigerant temperature control unit 1200.

A second insulation member 1262 may be disposed and fixed between the refrigerant flow control unit 1100 and a second side of the tube located on the side of the refrigerant flow control unit 1100. Through this, the second insulation member 1262 may thermally insulate external components including the refrigerant flow control unit 1100 from the refrigerant temperature control unit 1200.

Here, the insulation member 1260 may be made of a material having a thermal conductivity of 10 W/(m*K) or less. For example, the insulation member 1260 may be made of Teflon.

However, the location, thermal conductivity, and material of the insulation member described above are only examples, and an insulation member for thermally insulating external components from the refrigerant temperature control unit 1200 may be provided at any suitable location and may be made of any suitable material having any suitable thermal conductivity.

Figure 8:
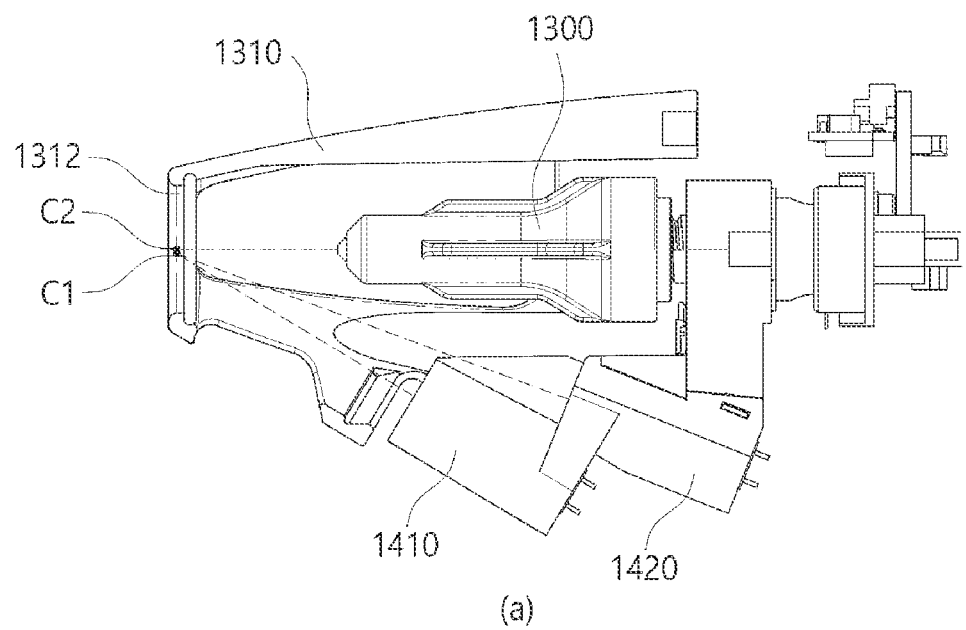
FIG. 8 is a view illustrating a sensor module (1400) according to the embodiment of the present specification.
Figure 8:
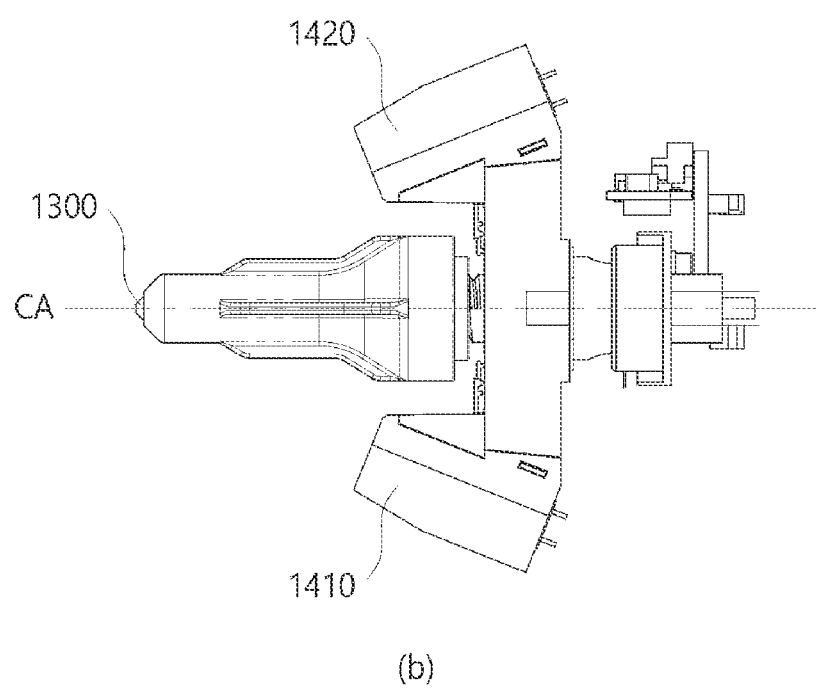

FIG. 8 is a view illustrating the sensor module 1400 according to the embodiment of the present specification.

Referring to FIG. 8, the sensor module 1400 may include the first temperature sensor 1410 and the second temperature sensor 1420.

The sensor module 1400 may be disposed in the body portion. For example, the sensor module 1400 may be disposed on the outside of the nozzle unit 1300 to be fixed thereto. In this case, the sensor module 1400 and the nozzle unit 1300 may be disposed inside the body portion such that the center part of the measuring area of the sensor module 1400 corresponds to the center part of the sprayed area of a refrigerant of the nozzle unit 1300. More specifically, the nozzle unit 1300 may include the guide unit 1310, and the guide unit 1310 may be in contact with the skin and may include a target defining member 1312 defining a targeted area. In this case, the sensor module 1400 may have a predetermined angle to the central axis CA of the body portion and may be fixed to the outer periphery of the nozzle unit 1300 such that the center part C1 of the measuring area of the sensor module 1400 is substantially the same as the center part C2 of a targeted area defined by the target defining member 1312.

The sensor module 1400 may include at least one temperature sensor. In other words, the sensor module 1400 may include the first temperature sensor 1410 and the second temperature sensor 1420.

In this case, the first temperature sensor 1410 and the second temperature sensor 1420 may be disposed in the body portion located in the same direction relative to the nozzle unit 1300.

For example, referring back to FIG. 8, the first temperature sensor 1410 and the second temperature sensor 1420 may be disposed in the lower end area of the inner surface of the body portion relative to the nozzle unit 1300. For example, the front end part of the first temperature sensor 1410 may be disposed closer to the front end F of the body portion than the front end part of the second temperature sensor 1420. That is, the first temperature sensor 1410 may be disposed closer to the front end of the body portion than the second temperature sensor 1420. Through such a structure, it is possible to minimize the size of the body portion while accurately measuring the temperature of a targeted area.

At least one of the first temperature sensor 1410 and the second temperature sensor 1420 may measure temperature information of a target.

For example, temperature information of a target may be obtained based on target temperatures measured by the first temperature sensor 1410 and the second temperature sensor 1420. For example, temperature information of a target may be obtained by giving weights to target temperatures, respectively, measured by the first and second temperature sensors, or by selecting one of target temperatures measured by the first and second temperature sensors.

For another example, temperature information of a target may be obtained by using one temperature sensor of the first temperature sensor 1410 and the second temperature sensor 1420. Specifically, as described later in FIG. 19, when it is determined that the first temperature sensor 1410 and the second temperature sensor 1420 operate normally, only one temperature sensor of the first temperature sensor 1410 and the second temperature sensor 1420 may be activated to obtain temperature information of a target.

Particularly, in a case in which only the second temperature sensor 1420 disposed by being spaced apart from the front end F of the body portion is used to obtain temperature information of a target, a lens may be provided on the front end part of the second temperature sensor 1420.

At least one temperature sensor of the first and second temperature sensors 1410 and 1420 may be used to save power required for operating the temperature sensor, thereby increasing lifetime of the sensor module 1400.

Meanwhile, as illustrated in FIG. 8(b), the first temperature sensor 1410 and the second temperature sensor 1420 may be disposed inside the body portion so as to be symmetrical with each other relative to the central axis CA of the body portion. In this case, as for the first temperature sensor 1410 and the second temperature sensor 1420, as illustrated in FIG. 8(a), the sensor module 1400 may have a predetermined angle to the central axis CA of the body portion and may be fixed on the outer periphery of the nozzle unit 1300 such that a center part C1 of the temperature measurement area of the first temperature sensor 1410 and the second temperature sensor 1420 and a center part C2 of a targeted area defined by the target defining member 1312 are substantially the same.

However, the arrangement of the sensor module 1400 described above is only an example, and the technical idea of the present specification is not limited thereto, and the sensor module 1400 may be embodied as any suitable structure in which the temperature of a targeted area can be accurately measured and the size of the cooling device 1000 ca Meanwhile, although not shown in the accompanying drawings, the cooling device 1000 according to the embodiment of the present specification may further include a refrigerant pressure maintaining part (a cryogen pressure keeper) maintaining pressure of a refrigerant at a preset pressure. For example, the refrigerant pressure maintaining part may be provided inside the cooling device 1000. For example, the refrigerant pressure maintaining part may be located in the gripping portion which can be gripped by a user. For another example, the refrigerant pressure maintaining part may be located in the body portion.

The refrigerant pressure maintaining part allows a refrigerant to be maintained in a high-pressure state, preventing pressure loss of a refrigerant and allowing a refrigerant to be sprayed in a fast response speed.

For example, the refrigerant pressure maintaining part may cool a refrigerant. Specifically, the refrigerant pressure maintaining part may cool a refrigerant by using a Peltier element. Additionally, the refrigerant pressure maintaining part may cool a refrigerant before the refrigerant is introduced into the refrigerant temperature control unit 1200 such that the refrigerant introduced into the refrigerant temperature control unit 1200 can be maintained in a high-pressure state. Furthermore, the refrigerant pressure maintaining part may be provided to further include a heat dissipation part for dissipating heat generated from the Peltier element.

In this case, the refrigerant pressure maintaining part may be applied to the cooling device 1000 using the refrigerant supply unit 4000 having a cartridge shape related to FIG. 2. However, the refrigerant pressure maintaining part may be more usefully applied to the cooling device 1000 using the refrigerant supply unit 4000 having the shape of a refrigerant tank related to FIG. 3.

Hereinafter, the structure of the filter fixing module 2000 disclosed in the present specification and the relation of the coupling of the filter fixing module 2000 with the cooling device 1000 will be described in detail with reference to FIGS. 9 to 18. The filter fixing module 2000 disclosed in the present specification may be provided as a structure which can perforate the refrigerant supply unit 4000 and receive the filter therein. Additionally, the cooling device 1000 disclosed in the present specification may include the coupling member 1840 having a structure in which the coupling member 1840 is coupled to the refrigerant supply unit 4000 such that the filter fixing module 2000 is received and disposed between the cooling device 1000 and the refrigerant supply unit 4000.

The filter fixing module 2000 according to the embodiment disclosed in the present specification may be configured to have a structure in which the refrigerant supply unit 4000 screwed to threads formed in the coupling member 1840 is perforated. Furthermore, the filter fixing module 2000 may be configured to have a structure in which the filter can be received in the filter fixing module 2000. Through such a structure, the filter fixing module 2000 according to the embodiment disclosed in the present specification may be provided to have a structure through which the refrigerant supply unit 4000 is coupled to the cooling device 1000 and the filter is received in the filter fixing module 2000 such that a refrigerant discharged from the refrigerant supply unit 4000 is introduced through the filter into the cooling device 1000.

Meanwhile, the connecting unit 1800 of the cooling device 1000 may be provided to have a structure having threads so as to be screwed to the refrigerant supply unit 4000. For example, the coupling member 1840 of the connecting unit 1800 to be described later may include a thread structure, and thus may be provided to be screwed to the threads of the refrigerant supply unit 4000. Through such a structure, a refrigerant discharged from the refrigerant supply unit 4000 may be prevented from being exposed to the outside, thereby minimizing risk due to the expansion of the refrigerant.

Figure 9:
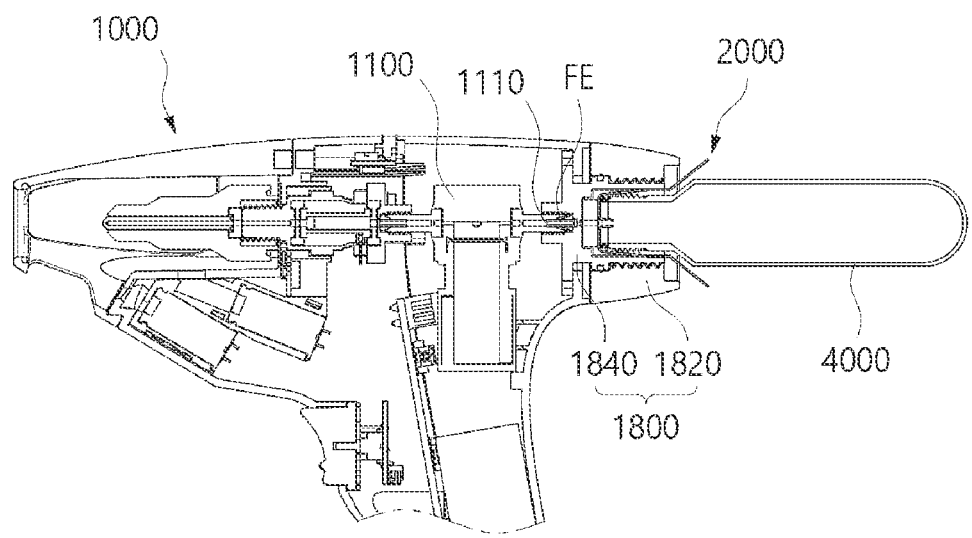
FIG. 9 is a view illustrating the internal structure of the cooling device (1000) to which the filter fixing module (2000) is mounted according to the embodiment of the present specification.

FIG. 9 is a view illustrating the internal structure of the cooling device 1000 to which the filter fixing module 2000 is mounted according to the embodiment of the present specification.

Referring to FIG. 9, the filter fixing module 2000 may be mounted to the connecting unit 1800 of the cooling device 1000 and thus a refrigerant may be supplied to the inlet 1110 of the refrigerant flow control unit 1100.

More specifically, the filter fixing module 2000 may be mounted to the inner surface of the coupling member 1840 screwed to the threads of the inner surface of the housing 1820 of the connecting unit 1800. In this case, in a state in which the filter fixing module 2000 is mounted to the inner surface of the coupling member 1840, the front end part FE of the coupling member 1840 may be connected to an end part of the inlet 1110 of the refrigerant flow control unit 1100. For example, through engagement of threads formed on the outer surface of the inlet 1110 of the refrigerant flow control unit 1100 with a third thread structure 1848 of the coupling member 1840 to be described later, the front end part FE of the coupling member 1840 and the inlet 1110 of the refrigerant flow control unit 1100 may be connected to each other.

The filter fixing module 2000 may be provided to have a structure in which the refrigerant flow path connected to the front end part FE of the coupling member 1840 is provided. Accordingly, a refrigerant may be introduced from the filter fixing module 2000 to the inlet 1110 of the refrigerant flow control unit 1100.

Figure 10:
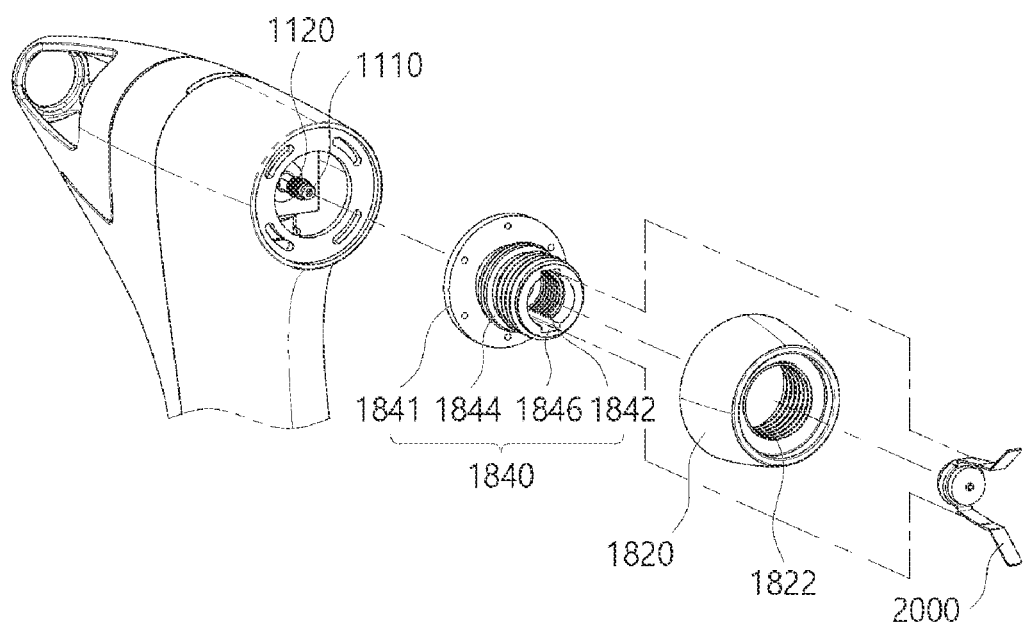
FIG. 10 is an exploded view of the cooling device (1000) to which the filter fixing module (2000) is mounted according to the embodiment of the present specification.

FIG. 10 is an exploded view of the cooling device 1000 to which the filter fixing module 2000 is mounted according to the embodiment of the present specification. Referring to FIG. 10, the threads 1120 may be formed on the outer side of the inlet 1110 of the refrigerant flow control unit 1100.

In addition, the coupling member 1840 of the connecting unit 1800 may be provided as a structure including a base 1841, a first thread structure 1842, and a second thread structure 1844. Additionally, the first thread structure 1842 may include at least one groove 1846.

In this case, the first thread structure 1842 and/or the at least one groove 1846 may have a structure through which the filter fixing module 2000 can be received or coupled thereto.

For example, the grip unit 2300 of the filter fixing module 2000 may be received in the at least one groove 1846 formed in the first thread structure 1842 such that the filter fixing module 2000 can be removably mounted to the coupling member 1840. This will be described later in detail with reference to FIGS. 12 to 18.

The second thread structure 1844 may be formed on the outer side of the first thread structure 1842. For example, the second thread structure 1844 may be formed on the outer surface of the coupling member 1840 in which the first thread structure 1842 is formed. Here, the second thread structure 1844 may be provided to be screwed to the housing 1820 of the connecting unit 1800.

Threads 1822 having crests and roots corresponding to the second thread structure 1844 may be formed in the inner surface of the housing 1820. In this case, the second thread structure 1844 are screwed to the threads 1822 of the inner surface of the housing 1820 and thus the coupling member 1840 and the housing 1820 may be coupled to each other. For example, the housing 1820 may be screwed to the coupling member 1840 so as to surround the outside of the coupling member 1840, and through such a structure, components (e.g., the coupling member 1840 and the inlet 1110 of the refrigerant flow control unit 1100) of the cooling device 1000 or the filter fixing module 2000 may be provided to be surrounded by the housing 1820 so as to be protected from external impacts.

Meanwhile, the housing 1820 may be provided to have a structure coupled to the coupling member formed on the outside of the body portion of the main body of the cooling device 1000. For example, the coupling member having a structure corresponding to the coupling member formed on the outside of the body portion of the main body may be formed on the outer surface of the housing 1820, and the coupling member of the housing 1820 is fitted over the coupling member formed on the outside of the body portion of the main body such that the housing 1820 can be fixedly coupled to the body portion of the main body.

Meanwhile, FIG. 10 illustrates that the housing 1820, which is a separate component from the main body of the cooling device 1000, is being coupled to the main body of the cooling device 1000. However, this is only an example, and the housing 1820 may be configured as a structure unified with the main body of the cooling device 1000, and threads may be formed in the inner surface of the main body such that the main body is screwed to the second thread structure 1844 of the coupling member 1840 described above.

Figure 11:
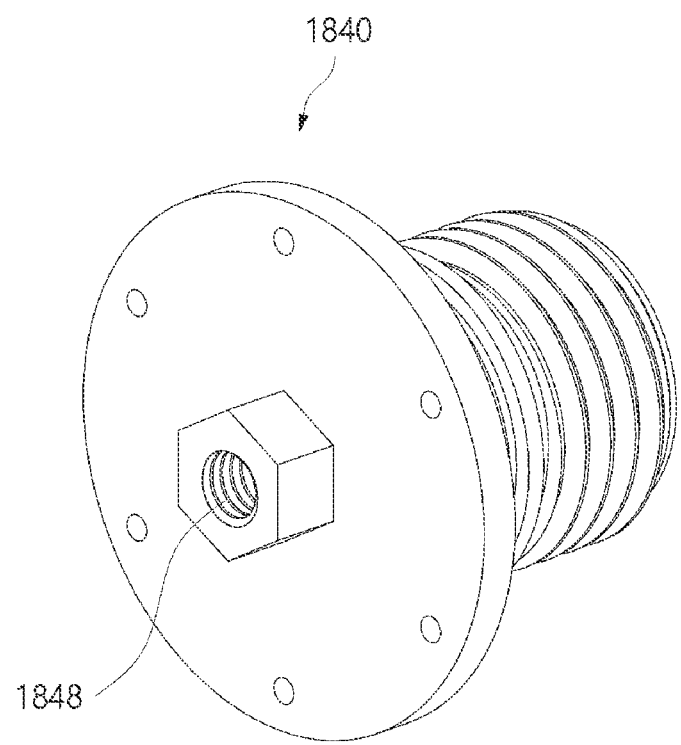
FIG. 11 is a perspective view of a coupling member (1840) to which the filter fixing module (2000) is mounted according to the embodiment of the present specification.

FIG. 11 is a perspective view of the coupling member 1840 to which the filter fixing module 2000 according to the embodiment of the present specification is mounted.

Referring to FIG. 11, the coupling member 1840 may further include the third thread structure 1848.

The third thread structure 1848 may be formed on a side opposite to the first thread structure 1842 relative to the base 1841 of the coupling member 1840. In this case, the third thread structure 1848 may be provided to have crests and roots corresponding to the threads 1120 formed on the outside of the inlet 1110 of the refrigerant flow control unit 1100 described above. Accordingly, the third thread structure 1848 may be screwed to the threads 1120 of the inlet 1110. Through this, the coupling member 1840 and the refrigerant flow control unit 1100 may be connected to each other. Additionally, the refrigerant moving passage of the filter fixing module 2000 may be connected to an end part of the inlet 1110 of the refrigerant flow control unit 1100 through the refrigerant moving hole of the coupling member 1840. Through this, a refrigerant discharged from the refrigerant supply unit 4000 may be introduced into the inlet 1110 of the refrigerant flow control unit 1100 through the filter fixing module 2000 and the refrigerant moving hole of the coupling member 1840.

However, the above-described structure is merely an example, and any suitable coupling structure may be provided to supply a refrigerant from the filter fixing module 2000 to the inlet 1110 of the refrigerant flow control unit 1100 by using a suitable type of coupling member by which the filter fixing module 2000 is mounted to the cooling device 1000.

Figure 12:
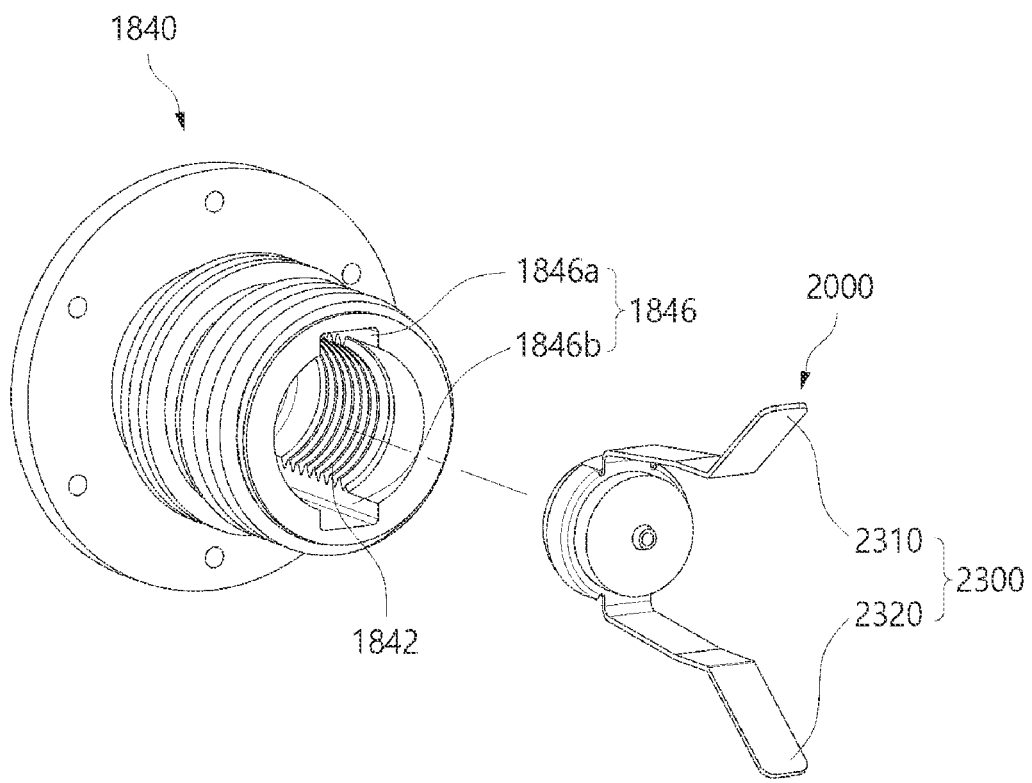
FIG. 12 is a view illustrating an aspect in which the filter fixing module (2000) is being coupled to the coupling member (1840) according to the embodiment of the present specification.

Referring to FIG. 12, FIG. 12 is a view illustrating an aspect in which the filter fixing module 2000 is being coupled to the coupling member 1840 according to the embodiment of the present specification.

Referring to FIG. 12, the filter fixing module 2000 may be received in or coupled to the coupling member 1840 in such a manner that the grip members 2310 and 2320 are received in at least two grooves 1846, respectively, formed in the inner surface of the coupling member 1840. Meanwhile, although not shown in FIG. 12, while the filter fixing module 2000 is received in the coupling member 1840, the refrigerant supply unit 4000 may be screwed to the first thread structure 1842 of the coupling member 1840. Accordingly, the filter fixing module 2000 may be provided to be disposed between the cooling device 1000 and the refrigerant supply unit 4000 screwed to the coupling member 1840 of the cooling device 1000.

Here, in order for a user to easily use the filter fixing module 2000, the filter fixing module 2000 may include the grip unit 2300. For example, the grip unit 2300 may include at least two grip members 2310 and 2320. In other words, the grip unit 2300 may include the first grip member 2310 and the second grip member 2320. The user may apply force to the first grip member 2310 and the second grip member 2320 such that the filter fixing module 2000 can be easily mounted to or removed from the cooling device 1000.

Meanwhile, as described above, the coupling member 1840 may have the first thread structure 1842 including the at least one groove 1846. In this case, the first grip member 2310 and the second grip member 2320 may be fitted into the at least one groove 1846 of the first thread structure 1842. For example, the first and second grip members 2310 and 2320 may be provided as the shape of a bent flat plate. In this case, a portion of the shape of a bent flat plate of each of the first and second grip members 2310 and 2320 may be provided to have size and shape corresponding to the at least one groove 1846 of the first thread structure 1842. Accordingly, the first grip member 2310 is fitted into the first groove 1846a of the first thread structure 1842 and the second grip member 2320 may be fitted into the second groove 1846b of the first thread structure 1842, so the filter fixing module 2000 may be removably mounted to the coupling member 1840.

However, the structures and coupling relation of the filter fixing module 2000 and the coupling member 1840 illustrated in FIG. 12 are merely an example and are not construed to be limited thereto. For example, multiple grip members may be used in various forms such that the filter fixing module 2000 is removably mounted to the coupling member 1840. Alternatively, the filter fixing module 2000 may include the coupling member of any suitable type other than the grip member such that the filter fixing module 2000 can be mounted to the connecting unit 1800 of the cooling device 1000.

Figure 13:
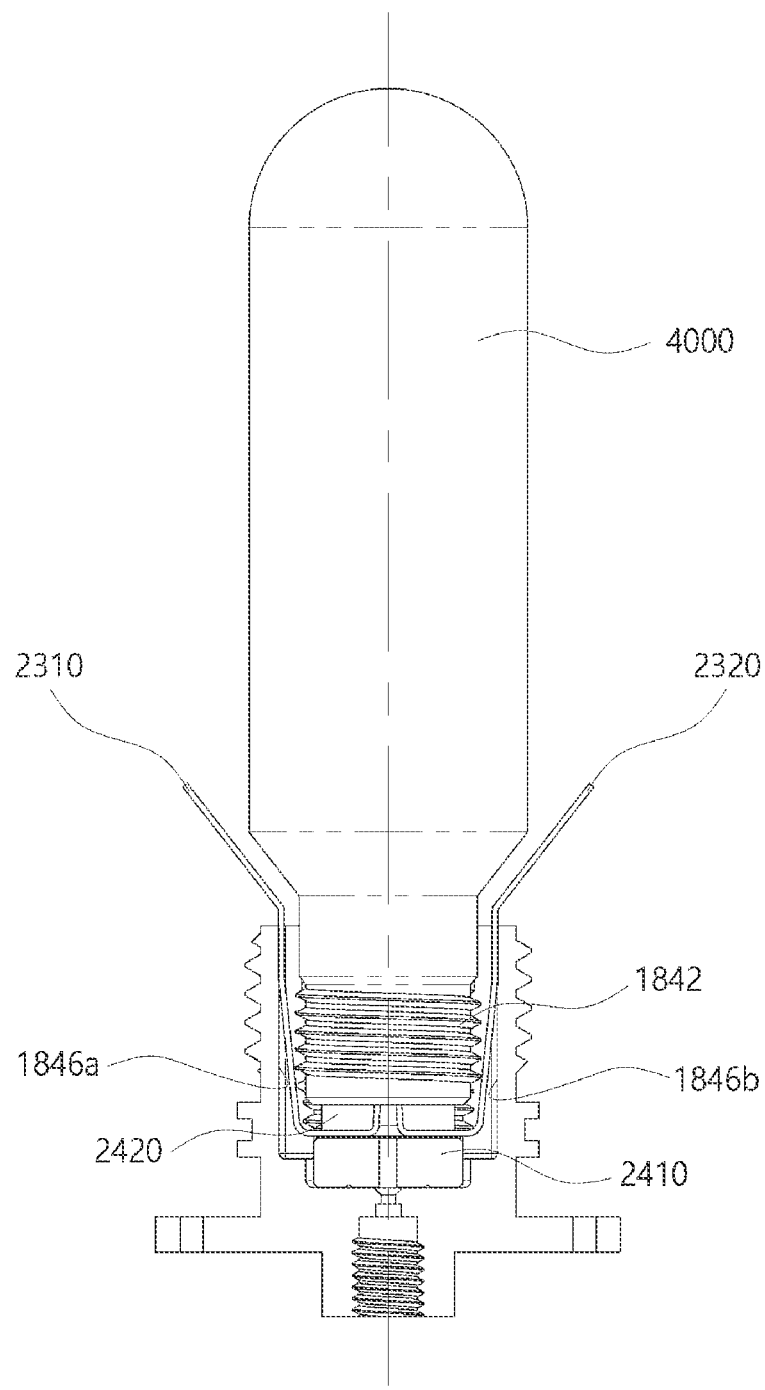
FIG. 13 is a view illustrating an aspect in which a refrigerant supply unit (4000) is screwed to the coupling member (1840) and is perforated by a perforating member (2200) of the filter fixing module (2000) according to the embodiment of the present specification.

FIG. 13 is a view illustrating an aspect in which the refrigerant supply unit 4000 is screwed to the coupling member 1840 and is perforated by the perforating member 2200 of the filter fixing module 2000 according to the embodiment of the present specification.

Referring to FIG. 13, as described above, in FIG. 12, the first grip member 2310 of the filter fixing module 2000 is received in the first groove 1846a of the first thread structure 1842 of the coupling member 1840, and the second grip member 2320 of the filter fixing module 2000 is received in the second groove 1846b of the first thread structure 1842 of the coupling member 1840, so the filter fixing module 2000 may be mounted to the coupling member 1840.

In this case, the refrigerant supply unit 4000 may have a structure which can be perforated by the filter fixing module 2000 and be coupled to the coupling member 1840.

For example, the refrigerant supply unit 4000 may include the refrigerant discharge hole perforated by the perforating member 2200 of the filter fixing module 2000. In this case, the diameter of the refrigerant discharge hole may be larger than the outer diameter of the body of the perforating member 2200. Through such a structure, the body of the perforating member 2200 may perforate the refrigerant discharge hole of the refrigerant supply unit 4000.

Meanwhile, the outer surface of the body of the perforating member 2200 may be made of a material having high rigidity (e.g., steel or stainless steel). On the other hand, the refrigerant discharge hole of the refrigerant supply unit 4000 may be made of a material having low rigidity (e.g., aluminum alloys or copper alloys). For another example, the outer surface of the body of the perforating member 2200 may have larger thickness than the refrigerant discharge hole of the refrigerant supply unit 4000. Through this, the perforating member 2200 may easily drill a hole in the refrigerant supply unit 4000.

In addition, the refrigerant supply unit 4000 may have a structure which can be coupled to the first thread structure 1842 of the coupling member 1840. For example, the refrigerant supply unit 4000 may have a thread structure including crests and roots corresponding to the first thread structure 1842. Accordingly, the refrigerant supply unit 4000 may be coupled to the coupling member 1840 by being screwed to the first thread structure 1842 of the coupling member 1840.

The filter fixing module 2000 disclosed in the present specification may be provided as a structure which can receive the filter therein and perforate the refrigerant supply unit 4000, so the filter fixing module 2000 may be advantageously configured such that the refrigerant supply unit 4000 is more easily coupled to the coupling member 1840 and a refrigerant discharged from the refrigerant supply unit 4000 passes through the filter.

Figure 14:
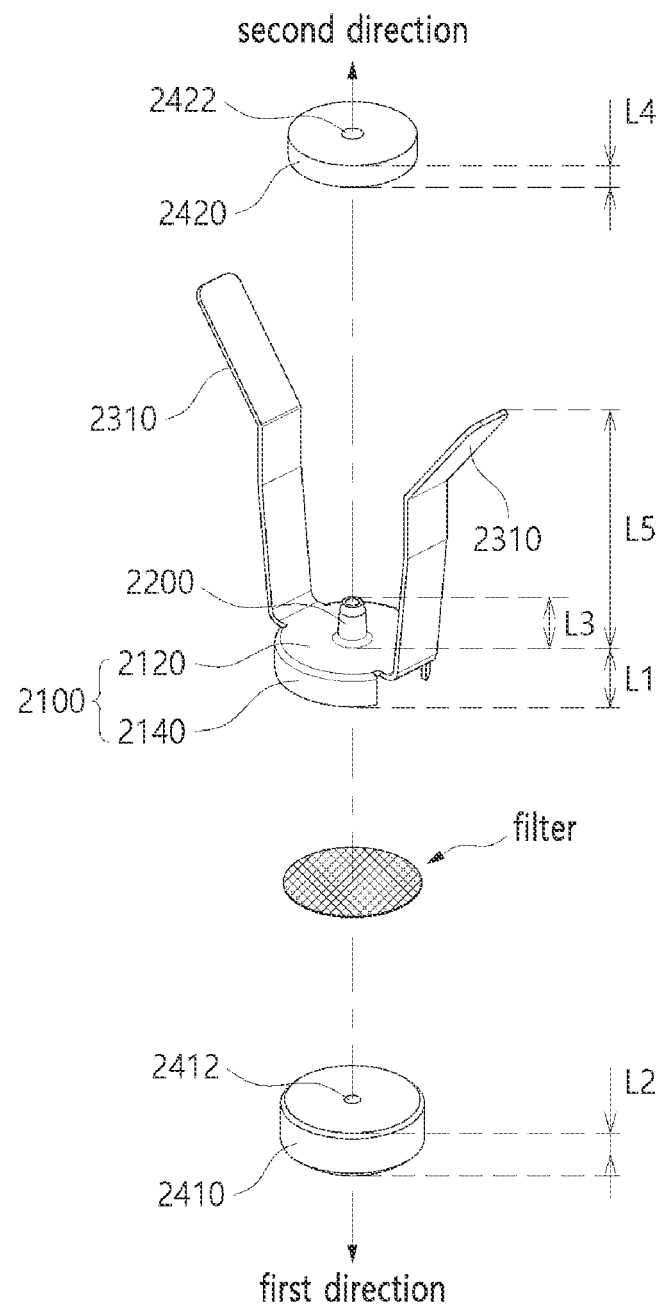
FIG. 14 is an exploded view of the filter fixing module (2000) according to the embodiment of the present specification.
Figure 15:
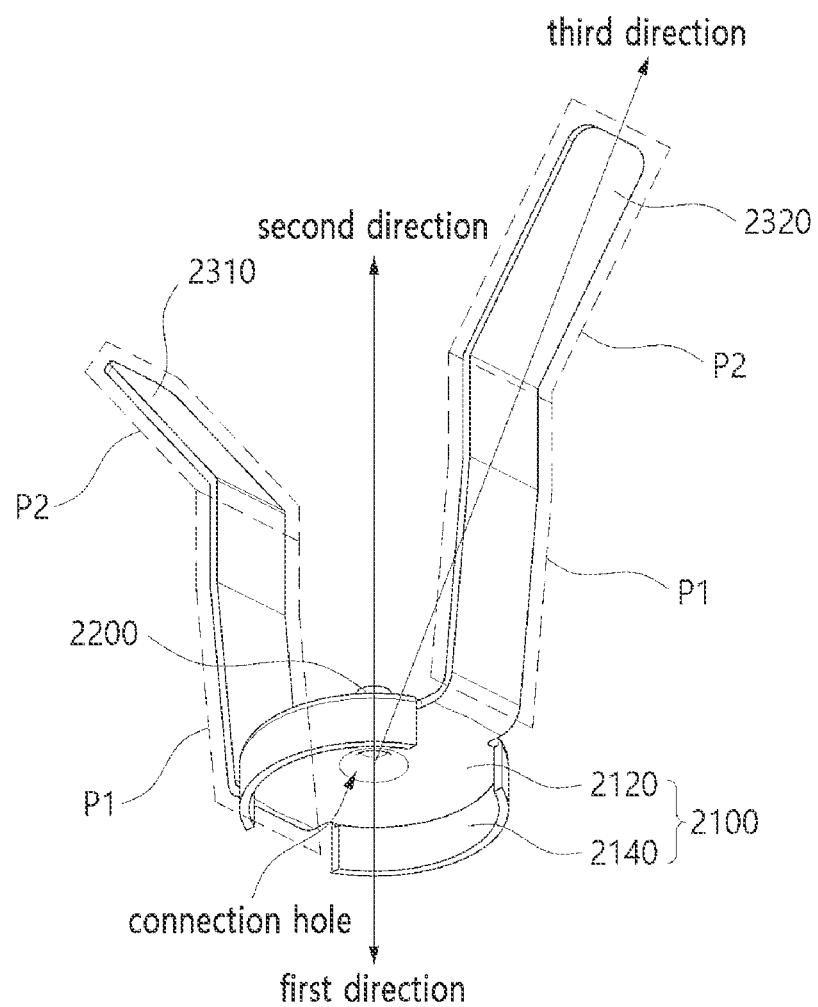
FIG. 15 is a view illustrating a body (2100) and a grip unit (2300) of the filter fixing module (2000) according to the embodiment of the present specification.
Figure 16:
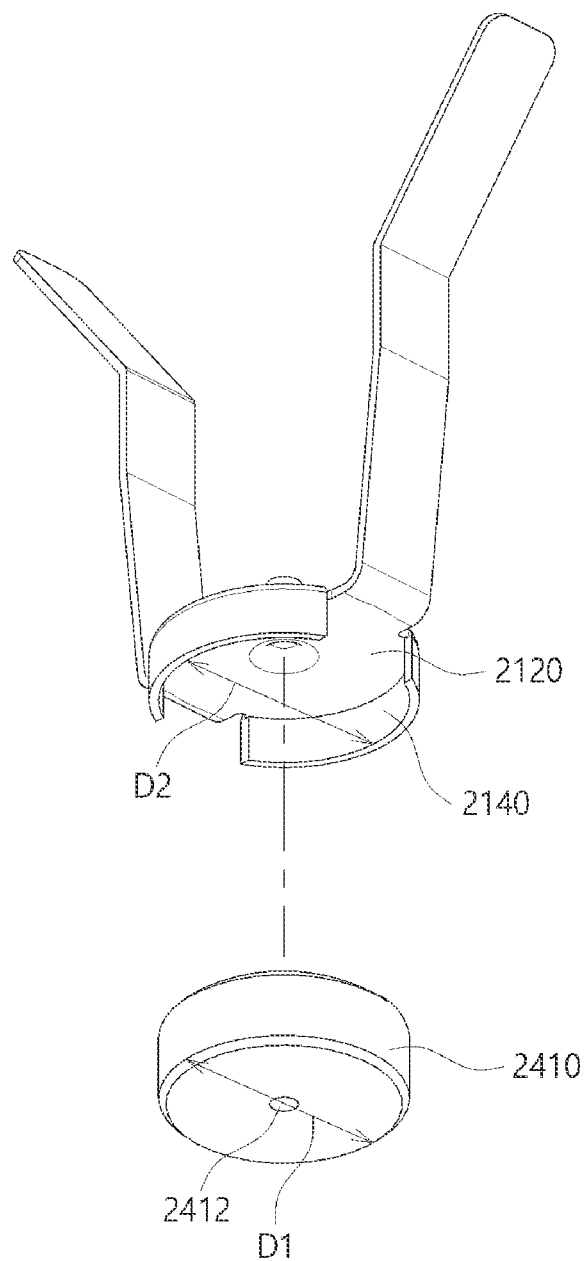
FIG. 16 is a view illustrating relation between the body (2100) and a first sealing member (2410) of the filter fixing module (2000) according to the embodiment of the present specification.

Referring to FIGS. 14 to 16, FIG. 14 is an exploded view of the filter fixing module 2000 according to the embodiment of the present specification. FIG. 15 is a view illustrating the body 2100 and the grip unit 2300 of the filter fixing module 2000 according to the embodiment of the present specification. FIG. 16 is a view illustrating relation between the body 2100 and the first sealing member 2410 of the filter fixing module 2000 according to the embodiment of the present specification.

Referring to FIGS. 14 to 16, the filter fixing module 2000 according to the embodiment may include the body 2100, the perforating member 2200, the grip member 2310 or 2320, and at least one sealing member 2400.

The body 2100 may be configured to receive the filter and at least a portion of the sealing member 2400.

For example, the body 2100 may be provided as a structure which includes the support surface 2120 for supporting the filter and the sealing member 2400, and the receiving surface 2140 which surrounds at least side surfaces of the filter and the sealing member 2400 and receives the filter and at least a portion of the sealing member.

The support surface 2120 may be provided to have a shape corresponding to the shape of each of the filter and the sealing member 2400. For example, when each of the filter and the sealing member 2400 disposed in the filter fixing module 2000 has the shape of a flat disk, the support surface 2120 may be provided to have a circular shape.

The receiving surface 2140 may be connected to the support surface 2120 of the body 2100. For example, the receiving surface 2140 may be provided to extend in the first direction from the outer edge of the support surface 2120.

In this case, the receiving surface 2140 may be provided to have a shape corresponding to the shape of each of the filter and the sealing member received in the receiving surface 2140.

For example, when each of the filter and the sealing member 2400 has the shape of a flat disk, the receiving surface 2140 may be provided to surround at least side surface of each of the filter and the sealing member 2400, so the receiving surface 2140 may be provided to have a curved surface corresponding to the curved surface of each of the filter and the sealing member 2400.

For another example, the filter may have a polygonal shape or a star shape and may have a size such that the vertices of the filter correspond to the receiving surface 2140 so as to increase a contact surface between the receiving surface 2140 and the sealing member 2400, thereby improving the sealing of the refrigerant.

Meanwhile, the body 2100 may further include a hole which can function as the moving passage of a refrigerant. For example, referring to FIGS. 14 and 15, the body 2100 may be provided as a structure which includes the connection hole located at the center part of the support surface 2120 and connected to the second end part of the perforating member 2200. The connection hole of the body 2100 may perform the function of the moving passage of a refrigerant which receives a refrigerant discharged from the second end part of the perforating member 2200 and discharges the refrigerant in a direction toward the cooling device 1000. For example, a refrigerant discharged from the connection hole of the body 2100 may be supplied through the support surface 2120 of the body 2100 and the filter received by the receiving surface 2140 to the inlet 1110 of the refrigerant flow control unit 1100 of the cooling device 1000. Through such a structure of the filter fixing module 2000, a refrigerant from which impurities are removed may be introduced into the cooling device 1000 and may be sprayed to a target, thereby minimizing the contamination of the cooling device 1000 and the target due to impurities.

The perforating member 2200 may be connected to the support surface 2120 of the body 2100 and may be provided to perform the function of perforating the refrigerant supply unit 4000. For example, the perforating member 2200 may include the first end part adjacent to the support surface 2120 of the body 2100, the second end part which receives a refrigerant discharged from the refrigerant supply unit 4000, and a body extending from the first end part toward the second end part. For example, the perforating member 2200 may extend in the second direction opposite to the first direction in which the receiving surface 2140 extends relative to the support surface 2120 of the body 2100.

Meanwhile, the body of the perforating member 2200 may be provided as a structure including the hollow hole formed therein such that a refrigerant discharged from the refrigerant supply unit 4000 is output to the inlet 1110 of the refrigerant flow control unit 1100 through the coupling member 1840.

The grip members 2310 and 2320 may extend from the body 2100, and may be mounted to the connecting unit 1800.

For example, the grip members 2310 and 2320 may be provided to extend from the support surface 2120 toward the outside of the support surface 2120 on which the receiving surface 2140 is not formed. More specifically, the grip members 2310 and 2320 may be provided to extend in the second direction opposite to the first direction from the outside of the support surface 2120 on which the receiving surface 2140 is not formed. The first grip member 2310 and the second grip member 2320 may be provided to have plate shapes substantially parallel with each other. In this case, as described above, the first grip member 2310 and the second grip member 2320 may be provided to have size and shape corresponding to the size and shape of the at least one groove 1846 such that the first grip member 2310 and the second grip member 2320 can be received in the at least one groove 1846 included in the threads of the coupling member 1840 of the connecting unit 1800 and mounted to the cooling device 1000.

For another example, each of the first grip member 2310 and the second grip member 2320 may be provided to have the shape of a bent flat plate. For example, referring back to FIG. 15, each of the first grip member 2310 and the second grip member 2320 may be provided as a structure having the shape of a bent flat plate which includes a first area P1 extending in the second direction, and a second area P2 extending in a direction having a predetermined angle to the second direction.

Specifically, the first grip member 2310 may be provided as a structure having the shape of a bent flat plate which includes the first area P1 extending in the second direction, and the second area P2 extending in the third direction having a predetermined angle to the second direction. Meanwhile, the second grip member 2320 may be provided as a structure having the shape of a bent flat plate which includes the first area P1 extending in the second direction, and the second area P2 extending in the fourth direction having a predetermined angle to the second direction. In this case, the fourth direction may be different from the third direction. Additionally, an angle formed between the first area P1 of the first grip member 2310 and the second area P2 of the first grip member 2310 may be substantially the same as an angle formed between the first area P1 of the second grip member 2320 and the second area P2 of the second grip member 2320. Accordingly, the first grip member 2310 and the second grip member 2320 may be provided to have substantially symmetrical structures to each other relative to the central axis.

The first area P1 of the first grip member 2310 and the first area P1 of the second grip member 2320 are substantially parallel with each other and may be provided to be spaced by the first distance apart from each other. Additionally, the second area P2 of the first grip member 2310 and the second area P2 of the second grip member 2320 may be provided to be spaced by a second distance different from the first distance apart from each other. In this case, the second distance may be shorter than the first distance, but according to the exemplary embodiment, the first grip member 2310 and the second grip member 2320 may be provided such that the second distance is longer than the first distance.

Meanwhile, as described above, at least a portion of the first area P1 of the first grip member 2310 may be received in the at least one groove (1846*a*) included in the threads of the coupling member 1840 of the connecting unit 1800 and may be mounted to the cooling device 1000. Furthermore, as described above, at least a portion of the second area P2 of the second grip member 2320 may be received in at least one groove 1846*b* included in the threads of the coupling member 1840 of the connecting unit 1800 to be mounted to the cooling device 1000.

Through the structure of the first grip member 2310 and the second grip member 2320 described above, the first grip member 2310 and the second grip member 2320 may be configured to protrude to the outside of the cooling device 1000. Accordingly, a user may easily apply force to the first grip member 2310 and the second grip member 2320 such that the filter fixing module 2000 can be easily removed from the cooling device 1000. This will be described in detail with reference to FIGS. 17 and 18.

Meanwhile, the filter fixing module 2000 may include at least one sealing member 2400. The at least one sealing member 2400 may function to prevent the leakage of a refrigerant and to block a refrigerant from the outside.

For example, the filter fixing module 2000 may include the support surface 2120 and the first sealing member 2410 received in the receiving surface 2140. Specifically, the first sealing member 2410 may be provided in the form of a flat disk, and may be disposed in the first direction relative to the body 2100, and may be received in the filter fixing module 2000 through the receiving surface 2140. Additionally, the first sealing member 2410 may be made of a material such as Teflon.

The first sealing member 2410 may function to prevent a refrigerant discharged through the first end part of the perforating member 2200 from leaking to the outside. For example, the first sealing member 2410 may function to decrease the leakage of a refrigerant by the contact surface of the support surface 2120 with the first sealing member 2410. In this case, in order to increase sealability by increasing the contact surface of the support surface 2120 with the first sealing member 2410, the filter may be configured to be smaller than the first sealing member 2410. For a specific example, the shape of the filter may be configured to have a polygonal shape or a star shape having vertices corresponding to the outer circumference of the first sealing member 2410.

Meanwhile, the first sealing member 2410 may be provided as a structure which includes a hole 2412 functioning as the moving passage of a refrigerant discharged through the first end part of the perforating member 2200. For example, the first sealing member 2410 may be provided to have a structure which includes the hole 2412 on the center part thereof, and the hole 2412 of the first sealing member 2410 may be formed to have a structure in which a refrigerant discharged through the first end part of the perforating member 2200 or passing through the filter can be received and the received refrigerant can be discharged toward the cooli For another example, the filter fixing module 2000 may include the second sealing member 2420 disposed at a side opposite to a side at which the first sealing member 2410 is located relative to the support surface 2120 of the body 210. For example, the second sealing member 2420 is fitted into the body of the perforating member 2200, and may be disposed at a side (e.g., in the second direction) opposite to a side (e.g., in the first direction) in which the first sealing member 2410 is located relative to the support surface 2120 of the body 2100. Additionally, the second sealing member

2420 may be provided to have the shape of a flat disk similar to the shape of the first sealing member 2410 and to be made of a material such as Teflon.

The second sealing member 2420 may function to decrease the leakage of a refrigerant to be supplied to the hollow hole of the perforating member 2200 from the refrigerant supply unit 4000 toward the outer surface of the perforating member 2200. Specifically, the second sealing member 2420 may be provided to decrease the leakage of a refrigerant discharged from the refrigerant supply unit 4000 and introduced into the second end part of the perforating member 2200 through the outer surface of the perforating member 2200 to the outside.

Meanwhile, the second sealing member 2420 may be provided as a structure which includes the through hole 2422 through which the body of the perforating member 2200 passes. For example, the second sealing member 2420 may be provided to have a structure which includes the through hole 2422 on the center part thereof, and the through hole 2422 of the second sealing member 2420 may be provided to have size and shape corresponding to the diameter and shape of the body such that the body of the perforating member 2200 can be fitted into the through hole. For example, the inner diameter of the second sealing member defined by the through hole 2422 of the second sealing member 2420 may be larger than the outer diameter of the body of the perforating member.

Meanwhile, the second sealing member 2420 may be configured to be integrated with the refrigerant supply unit 4000. In this case, the second sealing member 2420 may be provided to be integrated with the refrigerant supply unit 4000 by adhesive, or to be mechanically coupled to the refrigerant supply unit 4000 by having a shape corresponding to the shape of an end of the refrigerant supply unit 4000.

Due to such a second sealing member 2420, when a refrigerant is introduced into the second end part of the perforating member 2200 from the refrigerant supply unit 4000, the leakage of the refrigerant may be decreased.

Meanwhile, the filter may have a shape corresponding to the filter fixing module 2000 such that the filter is appropriately fixed in the filter fixing module 2000. For example, the filter may have a circular shape having a diameter corresponding to the inner diameter of the filter fixing module 2000 (e.g., the inner diameter of the receiving surface 2140).

Alternatively, in order to improve a sealing effect by increasing a contact area between the first sealing member 2410 and the support surface 2120, the filter may be a polygon having a size such that the vertices of the filter correspond to the inside of the filter fixing module 2000, specifically, the inner diameter of the receiving surface 2140. Alternatively, the filter may be provided to have a star shape such that the vertices of the filter correspond to the inside of the filter fixing module 2000, specifically, the inner diameter of the receiving surface 2140.

In addition, the filter may be disposed in any path of the flowing paths of a refrigerant in the filter fixing module 2000.

For example, the filter may be located between the support surface 2120 of the body 2100 and the first sealing member 2410. In this case, the filter may perform the function of filtering out impurities included in a refrigerant passing through the first end part of the perforating member 2200 and the hole of the body 2100.

In this case, in order to increase the size of a contact surface between the first sealing member 2410 and the support surface 2120, the filter may have a polygonal shape or a star shape having vertices meeting the outer circumference of the first sealing member 2410.

However, the arrangement of the filter described above is only an example, and the filter is disposed at an appropriate position in the flowing path of a refrigerant in the filter fixing module 2000 and removes impurities of the refrigerant such that the refrigerant from which the impurities are removed is supplied to the cooling device 1000. For example, the filter fixing module 2000 having any structure may be provided such that the filter can be located between the support surface 2120 of the body 2100 and the second sealing member 2420. Of course, the structures of components of the filter fixing module 2000 may be variously changed according to the arrangement position of the filter.

In addition, although the filter is illustrated in FIG. 14, the filter should not be construed as being included in the components of the filter fixing module 2000 disclosed in the present specification. Accordingly, even if any filter produced or distributed separately from the filter fixing module 2000 disclosed in the present specification is used, the filter should be interpreted as belonging to the scope of the claims of the filter fixing module 2000 disclosed in the present specification.

Referring back to FIG. 14, the receiving surface 2140 of the body 2100 may be provided to extend by a first length L1 from the edge of the support surface 2120 along the first direction. Meanwhile, the thickness of the first sealing member 2410 received in the receiving surface 2140 may be provided as a second length L2 along the first direction. In this case, the first length L1 and the second length L2 may be the same, but may be provided to be different from each other.

For example, the receiving surface 2140 and the first sealing member 2410 may be provided such that the second length L2 is longer than the first length L1. Through such a structure, it may be easier to dispose the first sealing member 2410 to be received in the receiving surface 2140 or to remove the received first sealing member 2410 from the receiving surface 2140. However, this is only an example, and of course, the length of the receiving surface 2140 and the thickness of the first sealing member 2410 may be vary.

Meanwhile, as described above, the perforating member 2200 may include the first end part adjacent to the support surface 2120 of the body 2100, the second end part which receives a refrigerant discharged from the refrigerant supply unit 4000, and the body extending from the first end part toward the second end part. In this case, the length of the body in a longitudinal direction thereof (e.g., the second direction) may be provided as a third length L3. Furthermore, the body of the perforating member 2200 may be provided to pass through the through hole 2422 of the second sealing member 2420. In this case, the thickness of the second sealing member 2420 may be provided as a fourth length L4 along the second direction. In this case, the third length L3 and the fourth length L4 may be the same, but may be provided to be different from each other.

For example, the perforating member 2200 and the second sealing member 2420 may be provided such that the third length L3 is longer than the fourth length L4. Through such a structure, the perforating member 2200 passes through the through hole 2422 of the second sealing member 2420 and the remaining protruding portion of the body perforates the refrigerant supply unit 4000, and thus a refrigerant may be introduced to the second end part of the perforating member 2200 from the refrigerant supply unit 4000, and the leakage of a refrigerant to be supplied to the second end part of the perforating member 2200 from the refrigerant supply unit 4000 may be decreased by the second sealing member 2420. However, this is only an example, and the length of the perforating member 2200 and the thickness of the second sealing member 2420 may be various.

Meanwhile, each of the first and second grip members 2310 and 2320 may be provided to have a fifth length L5 along the second direction. In this case, the third length L3 which is the length of the body of the perforating member 2200 and the fifth length L5 may be the same, but may be different from each other.

For example, the perforating member 2200 and the first and second grip members 2310 and 2320 may be provided such that the fifth length L5 is longer than the third length L3. For another example, the first and second grip members 2310 and 2320 may be provided such that the length of the first area P1 of each of the first and second grip members 2310 and 2320 is longer than the third length L3.

Through such a structure, the first and second grip members 2310 and 2320 may protrude to a more outer side than the refrigerant supply unit 4000 perforated by the perforating member 2200. Accordingly, a user may easily apply force to the first and second grip members 2310 and 2320 and may more easily remove the filter fixing module 2000 from the coupling member 1840 when the use of the refrigerant supply unit 4000 is completed.

Referring to FIG. 16, the first sealing member 2410 may be provided to have size and shape to be received in the receiving surface 2140. For a specific example, the first sealing member 2410 may be provided to have the shape of a flat disk corresponding to the shape of the receiving surface 2140 and to have a diameter for the first sealing member to be received in the receiving surface 2140.

For example, the first sealing member 2410 may be provided to have a diameter D1 smaller than the diameter D2 of the receiving surface 2140.

Through this, the first sealing member 2410 may be received in the receiving surface 2140 and may efficiently perform the function of decreasing leakage of a refrigerant flowing from the first end part of the perforating member 2200 to the cooling device 1000.

However, the shape and size of each of the first sealing member 2410 and the receiving surface 2140 illustrated in FIG. 16 are only an example, and each of the first sealing member 2410 and the receiving surface 2140 may be provided to have any suitable shape and size to receive the first sealing member 2410 in the receiving surface 2140.

Figure 17:
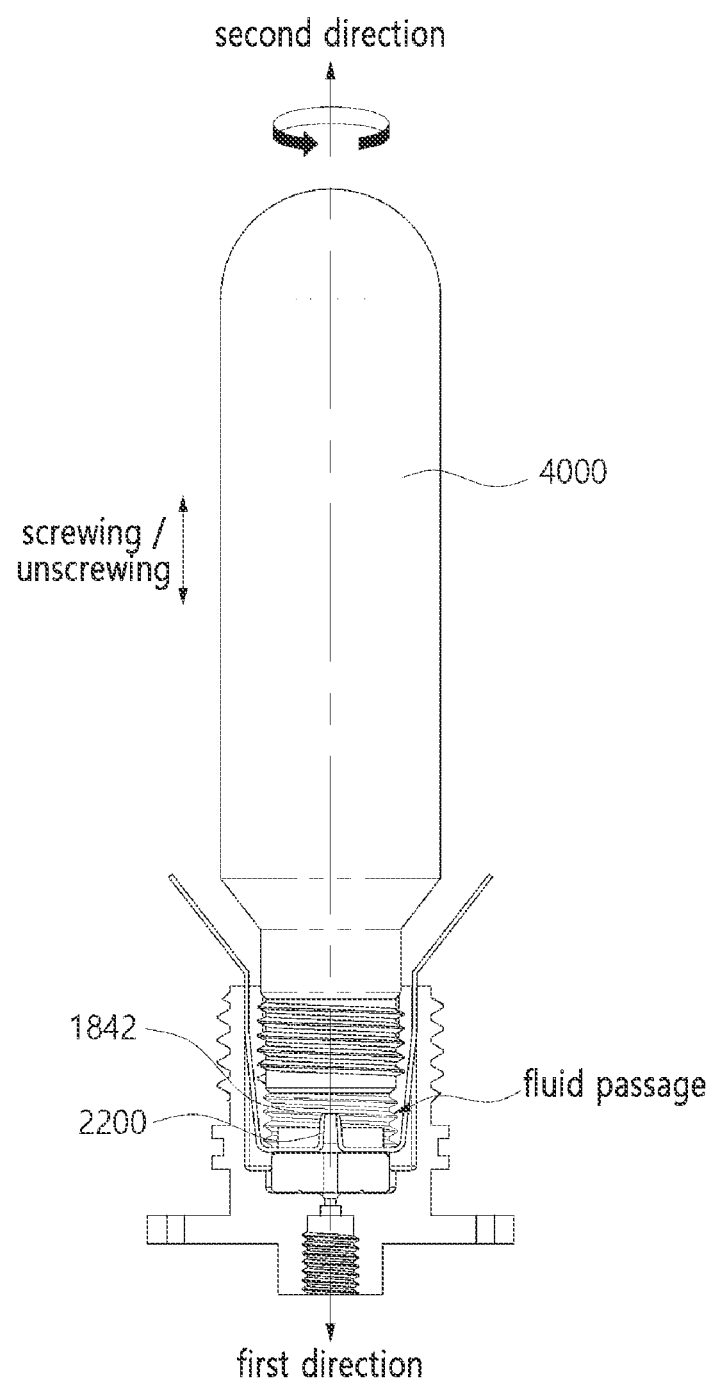
FIG. 17 is a view illustrating an aspect in which the refrigerant supply unit (4000) is being removed from the coupling member (1840) and the filter fixing module (2000) according to the embodiment of the present specification.

Referring to FIG. 17, FIG. 17 is a view illustrating an aspect in which the refrigerant supply unit 4000 is being removed from the coupling member 1840 and the filter fixing module 2000 according to the embodiment of the present specification.

Referring to FIG. 17, as described above, the refrigerant supply unit 4000 may be perforated by the perforating member 2200 of the filter fixing module 2000 and be screwed to the first thread structure 1842 of the coupling member 1840 so as to be mounted to the cooling device 1000. In this case, while the cooling device 1000 is being used, or after the use of the cooling device 1000 is completed, a user may disengage the refrigerant supply unit 4000 from the first thread structure 1842 of the coupling member 1840 by turning the refrigerant supply unit 4000.

For example, when the refrigerant supply unit 4000 is rotated counterclockwise (or clockwise), the threads of the refrigerant supply unit 4000 are engaged with the threads of the first thread structure 1842 of the coupling member 1840 such that the refrigerant supply unit 4000 is moved in the second direction from the first direction. Accordingly, the threads of the refrigerant supply unit 4000 may be disengaged from the threads of the first thread structure 1842 of the coupling member 1840.

In addition, when the refrigerant supply unit 4000 is rotated counterclockwise (or clockwise), the threads of the refrigerant supply unit 4000 and the threads of the first thread structure 1842 of the coupling member 1840 are engaged with each other, and thus the refrigerant supply unit 4000 is moved in the second direction from the first direction. Accordingly, the refrigerant supply unit 4000 may be spaced apart from the perforating member 2200. In other words, the refrigerant supply unit 4000 may be removed from the filter fixing module 2000.

Meanwhile, when the use of the refrigerant supply unit 4000 is completed, refrigerant in gaseous state may remain in the refrigerant supply unit 4000. In this case, when the remaining refrigerant is abruptly exposed to the atmosphere, the refrigerant may expand abruptly due to difference between the internal pressure of the refrigerant supply unit 4000 and atmospheric pressure, and this may generate noise and cause inconvenience to a user.

On the other hand, when the refrigerant supply unit 4000 disclosed in the present specification is removed from the coupling member 1840, particularly, when the refrigerant supply unit 4000 starts to be removed from the perforating member 2200 of the filter fixing module 2000, space which can function as the fluid passage may be formed in the internal portion of the coupling member 1840 between the refrigerant supply unit 4000 and the filter fixing module 2000. In this case, a gaseous refrigerant remaining in the refrigerant supply unit 4000 may use an area between the refrigerant supply unit 4000 and the filter fixing module 2000 as the fluid passage to be gradually discharged to the outside. Accordingly, the structure of the filter fixing module 2000 and the refrigerant supply unit 4000 disclosed in the present specification may minimize noise and a user's inconvenience caused by difference of pressure which may instantaneously occur when the refrigerant supply unit 4000 is removed from the cooling device 1000.

FIG. 17 illustrates only an aspect of the removal of the refrigerant supply unit 4000, but this is only for convenience of explanation. When the refrigerant supply unit 4000 is rotated clockwise (or counterclockwise), the threads of the refrigerant supply unit 4000 and the threads of the first thread structure 1842 of the coupling member 1840 are engaged with each other, and thus the refrigerant supply unit 4000 may move from the second direction to the first direction. Accordingly, the threads of the refrigerant supply unit 4000 may be screwed to the first thread structure 1842 to be coupled to the coupling member 1840, and the refrigerant supply unit 4000 may be perforated by the perforating member 2200.

Figure 18:
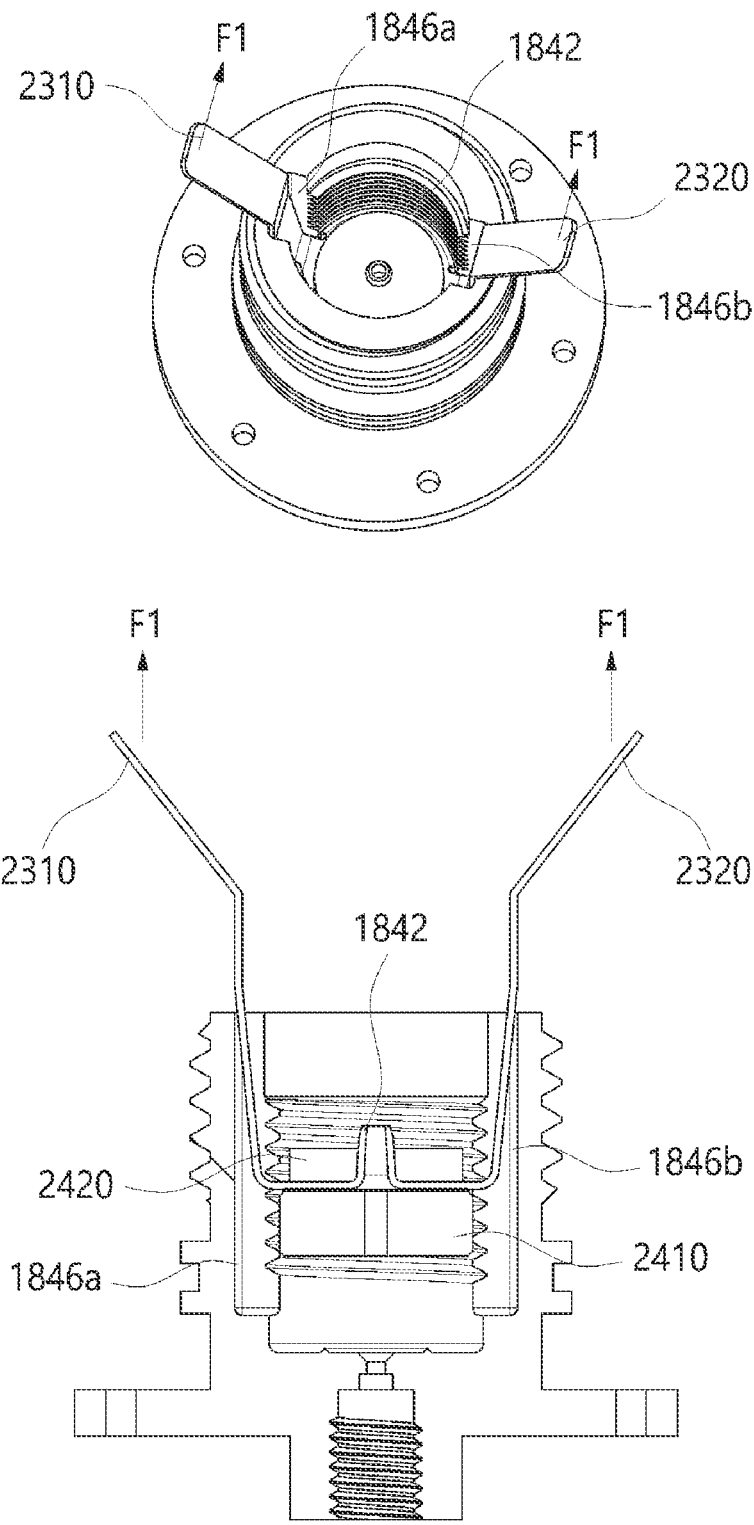
FIG. 18 is a view illustrating an aspect in which the filter fixing module (2000) is being removed from the coupling member (1840) according to the embodiment of the present specification.

Referring to FIG. 18, FIG. 18 is a view illustrating an aspect in which the filter fixing module 2000 is being removed from the coupling member 1840 according to the embodiment of the present specification.

Referring to FIG. 18, as described above, the filter fixing module 2000 may be mounted to the coupling member 1840 in such a manner that the first grip member 2310 is fitted into a groove 1846*a* included in the threads 1842 of the coupling member 1840 and the second grip member 2320 is fitted into a groove 1846*b* included in the threads 1842 of the coupling member 1840. In this case, when the cooling device 1000 is being used or the use of the cooling device 1000 is completed, a user may apply force F1 to the first and second grip members 2310 and 2320 protruding to the outside and may remove the filter fixing module 2000 from the coupling member 1840.

Specifically, a user may apply force F1 to the second area of the first and second grip members 2310 and 2320 protruding to the outside, and may remove the first and second grip members 2310 and 2320 from the grooves 1846a and 1846b, respectively, included in the threads 1842 of the coupling member 1840.

For example, a user may apply a pulling force F1 to the first grip member 2310 and the second grip member 2320 and may remove the first and second grip members 2310 and 2320 from the grooves 1846a and 1846b, respectively, included in the threads 1842 of the coupling member 1840.

For another example, a user may apply force to the first grip member 2310 and the second grip member 2320 in a direction in which the first grip member 2310 and the second grip member 2320 approaches each other, and may remove the first and second grip members 2310 and 2320 from the grooves 1846a and 1846b, respectively, included in the threads 1842 of the coupling member 1840.

However, the direction of force applied to the first and second grip members 2310 and 2320 illustrated in the present specification and the drawing is only an example, and force may be applied to the first and second grip members 2310 and 2320 in any suitable direction so as to remove the first and second grip members 2310 and 2320 from the grooves 1846a and 1846b, respectively, included in the threads 1842 of the coupling member 1840.

The filter fixing module 2000 according to the embodiment of the present specification may include the first grip member 2310 and the second grip member 2320 protruding to the outside such that a user can easily apply force thereto. Accordingly, the filter fixing module 2000 according to the embodiment of the present specification may be easily removed from the coupling member 1840 with little force when use thereof is completed.

Above, the structure of the filter fixing module 2000 including the body 2100, the perforating member 2200, the grip unit 2300, and/or the sealing member 2400 was mainly described with reference to FIGS. 9 to 18 such that the filter fixing module 2000 is mounted to the coupling member 1840.

However, the structure of each of components including the filter fixing module 2000, the body 2100, the perforating member 2200, the grip unit 2300, and/or the sealing member 2400 described with reference to FIGS. 9 to 18 is only an example. Accordingly, the structure of each of the components of the filter fixing module 2000, the body 2100, the perforating member 2200, the grip unit 2300, and/or the sealing member 2400 is not construed by being limited to the descriptions of the present specification and the illustrations of the drawings.

Meanwhile, although not shown in FIGS. 9 to 18, a cover to receive the refrigerant supply unit 4000 may be provided on the outside of the refrigerant supply unit 4000. In this case, there may be threads or coupling elements on the outer surface of the cover of the refrigerant supply unit 4000. Furthermore, threads or coupling elements corresponding to the threads or coupling elements formed on the outer surface of the cover of the refrigerant supply unit 4000 may be formed on the outer surface of the housing 1820 of the connecting unit 1800. Accordingly, the cover of the refrigerant supply unit 4000 may be coupled to the housing 1820 of the connecting unit 1800 by screwing, and accordingly, the refrigerant supply unit 4000 may be configured to be mounted to the cooling device 1000 while being receive The cooling device 1000 according to the embodiment of the present specification may spray a refrigerant introduced according to the refrigerant flow control of the refrigerant flow control unit 1100 to a targeted area. Additionally, the cooling device 1000 may control the temperature of a refrigerant through the refrigerant temperature control unit 1200, and may spray the refrigerant to a targeted area. In this case, the cooling device 1000 may be embodied to measure the temperature of a targeted area in real time and to control the temperature of a refrigerant based on the temperature of the targeted area. Furthermore, the cooling device 1000 may obtain a user's input presetting a cooling condition through the input module 1500 or a user's input instructing the initiation of the cooling operation through the input module 1500. In addition, the cooling device 1000 may provide a user with cooling information during cooling through the output module 1600.

The above-described operations may be controlled by the control module 1700 of the cooling device 1000. For example, the control module 1700 may obtain an input related to a cooling condition or an input initiating the cooling operation from the input module 1500, and may control the refrigerant flow control unit 1100 and/or the refrigerant temperature control unit 1200 of the cooling device 1000 to perform cooling corresponding to the input related to the cooling condition. Additionally, the control module 1700 may control whether to activate the sensor module 1400 by determining whether the sensor module 1400 operates normally.

Meanwhile, since the cooling device 1000 performs a cooling operation on a targeted area that is a part of the body, the safety of the cooling device 1000 is essential. To this end, the cooling device 1000 according to the embodiment of the present specification may include at least two temperature sensors. In this case, the cooling device 1000 may be embodied to determine whether the at least two temperature sensors operate normally. Through this, the cooling device 1000 according to the embodiment of the present specification may measure the temperature of a targeted area and may prevent accidents such as overcooling of a targeted area due to malfunction of the temperature sensors.

Hereinafter, various operations in which the control module 1700 according to the embodiment of the present specification controls components of the cooling device 1000 will be described with reference to FIGS. 19 to 28.

Figure 19:
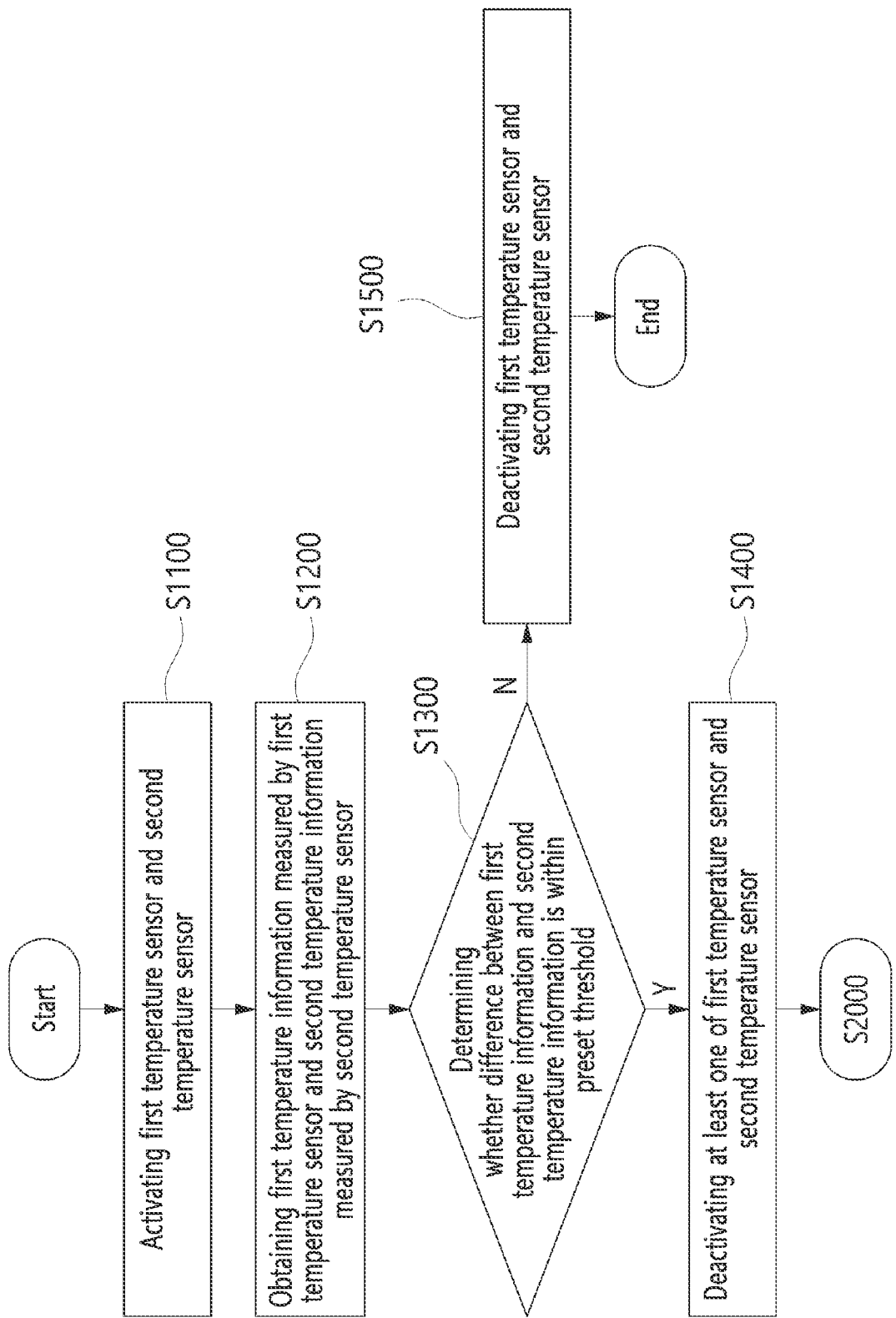
FIG. 19 is a flowchart related to the operation of a control module (1700) for determining whether the sensor module (1400) operates normally according to the embodiment of the present specification.

FIG. 19 is a flowchart related to the operation of a control module 1700 for determining whether the sensor module 1400 operates normally according to the embodiment of the present specification.

The method of determining whether the sensor module 1400 operates normally as illustrated in FIG. 19 may be initiated when the cooling device 1000 is activated by a user' input turning on a switch. Alternatively, the method of determining whether the sensor module operates normally may be initiated by additionally obtaining a user's input initiating the operation of determining whether the sensor module 1400 operates normally after the cooling device 1000 is activated. Alternatively, when the cooling device 1000 is activated, the control module 1700 may, through the output module 1600, output information instructing the initiation of the operation of determining whether the sensor module 1400 operates normally to a user. Here, by the input module 1500, a user may instruct the initiation of the operation of determining whether the sensor module 1400 operates normally, and in response to the user's input, the control module 1700 may be embodied to initiate the operation of determining whether the sensor module 1400 operates normally.

Hereinafter, the embodiment of the method of determining whether the sensor module 1400 operates normally which is disclosed in the present specification and performed by the control module 1700 will be described in detail.

Referring to FIG. 19, the method of determining whether the sensor module 1400 operates normally may include a step of activating a first temperature sensor and the second temperature sensor at S1100, a step of obtaining first temperature information measured by the first temperature sensor and second temperature information measured by the second temperature sensor at S1200, and a step of determining whether the difference between the first temperature information and the second temperature information is within a preset threshold at S1300. Furthermore, the method of determining whether the sensor module 1400 operates normally may include a step of deactivating at least one of the first temperature sensor and the second temperature sensor at S1400 or a step of deactivating the first temperature sensor and the second temperature sensor at S1500 according to whether the difference between the first temperature information and the second temperature information is within a preset threshold.

In the step of activating the first temperature sensor and the second temperature sensor at S1100, when the power of the cooling device 1000 is turned on and starts to be supplied to the control module 1700, the control module 1700 may be embodied to activate the sensor module 1400.

For example, as described above, the sensor module 1400 may include at least two temperature sensors. In this case, the control module 1700 may control the sensor module 1400 such that the first temperature sensor 1410 and the second temperature sensor 1420 of the sensor module 1400 are activated.

When both the first temperature sensor 1410 and the second temperature sensor 1420 are activated, the sensor module 1400 may transmit a signal indicating that the first temperature sensor 1410 and the second temperature sensor 1420 are activated to the control module 1700.

Figure 20:
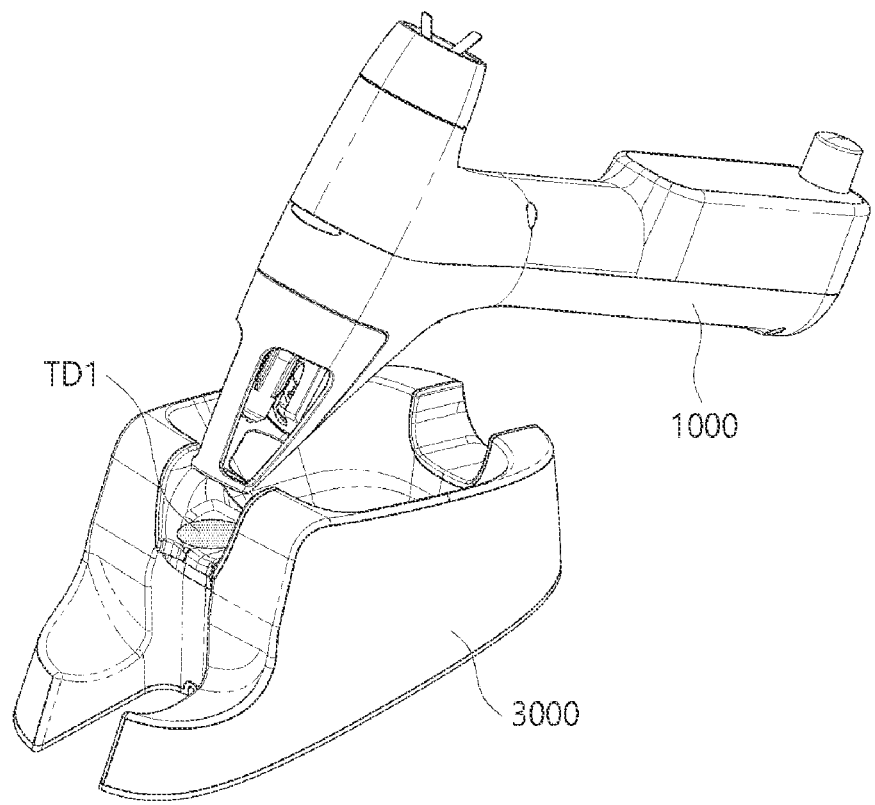
FIG. 20 is a view illustrating an aspect in which first temperature information and second temperature information are measured to determine whether the sensor module (1400) operates normally according to the embodiment of the present specification.

Referring to FIG. 20, FIG. 20 is a view illustrating an aspect in which the first temperature information and the second temperature information are measured to determine whether the sensor module 1400 operates normally according to the embodiment of the present specification.

For example, when the first temperature sensor 1410 and the second temperature sensor 1420 are activated, the control module 1700, through the output module 1600, may provide a user with information instructing the contact of the guide unit 1310 with the temperature measurement area TD1 of the stand 3000.

When the guide unit 1310 is brought into contact with the temperature measurement area TD1 of the stand 3000 by a user, each of the first temperature sensor 1410 and the second temperature sensor 1420 may measure the temperature of the temperature measurement area TD1. In this case, the sensor module 1400 may be embodied such that the first temperature information T1 related to the temperature of the temperature measurement area TD1 of the stand 3000 obtained from the first temperature sensor 1410, and the second temperature information T2 related to the temperature of the temperature measurement area TD1 of the stand 3000 obtained from the second temperature sensor 1420 are transmitted to the control module 1700.

At the step S1200 of obtaining the first temperature information measured by the first temperature sensor and the second temperature information measured by the second temperature sensor, the control module 1700 may obtain the first temperature information T1 obtained from the first temperature sensor 1410 and the second temperature information T2 obtained from the second temperature sensor 1420 through the sensor module 140.

At the step S1300 of determining whether difference between the first temperature information and the second temperature information is within a preset threshold, the control module 1700 may determine whether the first temperature sensor 1410 and the second temperature sensor 1420 operate normally, or reliability of each of the first temperature information T1 and the second temperature information T2 based on the first temperature information T1 and the second temperature information T2 obtained from the sensor module 1400.

For example, when the difference between the first temperature information T1 and the second temperature information T2 is large, it is highly likely that the reliability of at least one of the first temperature information T1 and the second temperature information T2 is relatively low. On the other hand, when the difference between the first temperature information T1 and the second temperature information T2 is small, it is highly likely that the reliability of each of the first temperature information T1 and the second temperature information T2 is relatively high.

Accordingly, the control module 1700 may determine the reliability of each of the first temperature information T1 and the second temperature information T2 or whether the first temperature sensor 1410 and the second temperature sensor 1420 operate normally based on the first temperature information T1 and the second temperature information T2.

For example, the control module 1700 may determine the reliability of each of the first temperature information T1 and the second temperature information T2 based on whether difference between the first temperature information T1 and the second temperature information T2 is within a preset threshold.

In addition, the control module 1700 may be configured to calculate difference between the first temperature information and the second temperature information based on the first temperature information T1 and the second temperature information T2.

Additionally, a threshold may be preset in relation to difference between the first temperature information and the second temperature information.

In this case, the control module 1700 may determine whether difference between the first temperature information and the second temperature information is within the preset threshold, and accordingly, may control the subsequent operation of the cooling device 1000.

For example, when the difference between the first temperature information and the second temperature information is not within a preset threshold, it may mean that the reliability of at least one temperature information of the first temperature information T1 and the second temperature information T2 is relatively low. Here, relatively low reliability may mean that at least one of the first temperature sensor 1410 and the second temperature sensor 1420 is highly likely to not operate normally. Alternatively, it could mean that the first temperature sensor 1410 and the second temperature sensor 1420 operate normally but any one of measured first temperature information T1 and measured second temperature information T2 has an error occurred due to external factors.

Accordingly, when the difference between the first temperature information and the second temperature information is not within a preset threshold, the control module 1700 may control the cooling device 1000 such that the subsequent cooling operation of the cooling device 1000 is not performed. Accordingly, when the difference between the first temperature information and the second temperature information is not within a preset threshold, the control module 1700 may be configured to deactivate the first temperature sensor 1410 and the second temperature sensor 1420 at S1500 and to stop cooling operation.

On the other hand, when the difference between the first temperature information and the second temperature information is within a preset threshold, it may mean that the reliability of each of the first temperature information T1 and the second temperature information T2 may be relatively high. Furthermore, it may mean that there is a high probability that at least one of the first temperature sensor 1410 obtaining the first temperature information T1 and the second temperature sensor 1420 obtaining the second temperature information T2 is normally operating.

Accordingly, when the difference between the first temperature information and the second temperature information is within a preset threshold, the control module 1700 may be configured to perform the subsequent cooling operation of the cooling device 1000.

For example, the control module 1700 may be configured to deactivate at least one of the first temperature sensor 1410 and the second temperature sensor 1420 at S1400. As described above, when the difference between the first temperature information and the second temperature information is within a preset threshold, it may mean that it is highly likely that "at least any one sensor" of the first temperature sensor 1410 obtaining the first temperature information T1 and the second temperature sensor 1420 obtaining the second temperature information T2 is operating normally, so at least any one temperature sensor of the first temperature sensor 1410 and the second temperature information T2 may be deactivated to save power required for the temperature measurement of the temperature sensors.

Meanwhile, although not shown in FIG. 20, the first temperature information and the second temperature information may be measured in response to input by a user instructing temperature measurement through the input module 1500.

For example, in FIG. 20, while the guide unit 1310 is in contact with the temperature measurement area TD1 of the stand 3000, a user may instruct temperature measurement by the first temperature sensor 1410 and the second temperature sensor 1420 through the input module 1500.

For example, a user may instruct temperature measurement by the first temperature sensor 1410 and the second temperature sensor 1420 through the second input module 1520 located on the gripping portion of the cooling device 1000. Here, the input of instructing temperature measurement may be related to an input instructing the obtaining of the temperature information of a specific area (e.g., the temperature measurement area TD1 of the stand 3000) for determining whether the first temperature sensor 1410 and the second temperature sensor 1420 operate normally.

The control module 1700 may control the sensor module 1400 such that the first temperature sensor 1410 and the second temperature sensor 1420 measure temperatures in response to a user's input.

Figure 21:
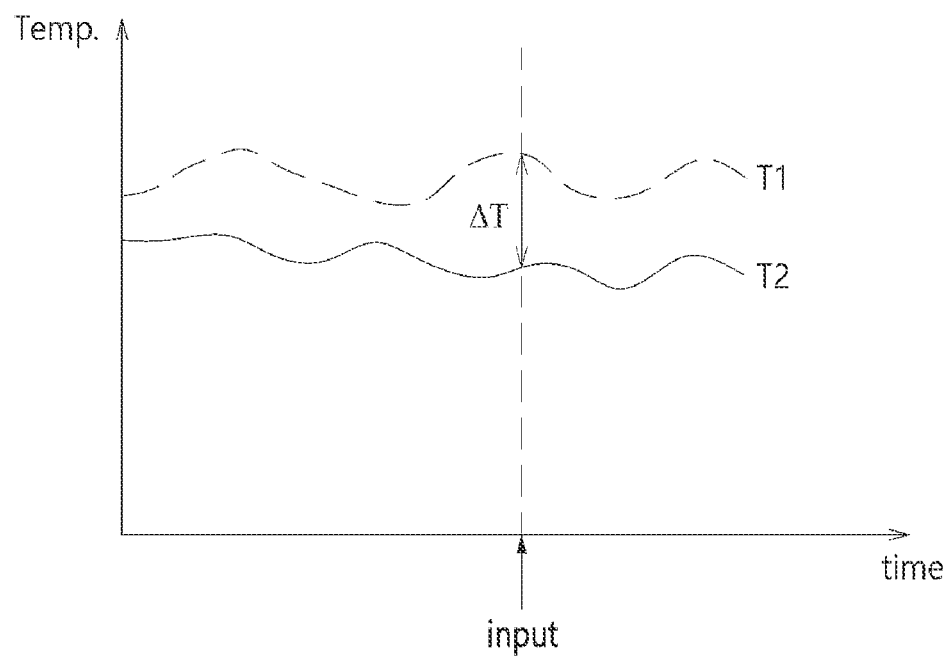
FIG. 21 is a graph illustrating difference between the first temperature information and the second temperature information calculated by the control module (1700) to determine whether the sensor module (1400) operates normally according to the embodiment of the present specification.

Referring to FIG. 21, FIG. 21 is a graph illustrating difference between the first temperature information and the second temperature information calculated by the control module 1700 to determine whether the sensor module 1400 operates normally according to the embodiment of the present specification.

Through the sensor module 1400, the control module 1700 may obtain the first temperature information T1 related to the temperature of the temperature measurement area TD1 of the stand 3000 obtained from the first temperature sensor 1410, and the second temperature information T2 related to the temperature of the temperature measurement area TD1 of the stand 3000 obtained from the second temperature sensor 1420.

For example, as described above, when a switch is turned on by a user, the first temperature sensor 1410 and the second temperature sensor 1420 may be activated. For example, a switch button may be formed on the lower end of the cooling device 1000 illustrated in FIG. 20. In this case, when a user turns on the switch button, the first temperature sensor 1410 and the second temperature sensor 1420 may be activated. In this case, the first temperature sensor 1410 and the second temperature sensor 1420 may measure the temperature of the temperature measurement area from the time point of activation. Accordingly, the control module 1700 may determine whether the first temperature sensor 1410 and the second temperature sensor 1420 are normal based on a measured temperature at arbitrary time point from the activated time point.

For another example, as described above, a user may instruct the measurement of the temperature of the temperature measurement area TD1 through the input module 1500. In this case, the control module 1700 may determine whether the first temperature sensor 1410 and the second temperature sensor 1420 are normal based on the measured temperature of the temperature measurement area TD1 after the user's input is obtained. For example, the control module 1700 may be embodied to calculate difference between the first temperature information T1 and the second temperature information T2 based on the first temperature information T1 and the second temperature information T2 at time point at which the input of instructing temperature measurement by a user through the input module 1500 is obtained.

Alternatively, the control module 1700 may be embodied to calculate difference between the first temperature information T1 and the second temperature information T2 based on the first temperature information T1 and the second temperature information T2 at time point at which a preset time elapses from time point at which the input of instructing temperature measurement by a user through the input module 1500 is obtained.

However, the above description is only an example, and of course, it is possible to embody various control methods in which the control module 1700 can determine whether the sensor module 1400 operates normally based on temperature information obtained at any suitable time.

In addition, referring to FIG. 21, in a case in which a user's input is obtained, the first temperature information T1 and the second temperature information T2 are illustrated to be obtained even before time point at which the user's input is obtained, but this is only an example, and of course, the first temperature information T1 and the second temperature information T2 may be embodied to be measured only when a user's input is obtained.

Meanwhile although not shown in FIG. 19, when both the first temperature sensor and the second temperature sensor are activated at S1100, the control module 1700 may be configured to output information, through the output module 1600, indicating that the first temperature sensor 1410 and the second temperature sensor 1420 are activated to a user.

For example, the control module 1700 may be configured to output information, through the output module 1600, indicating that the first temperature sensor 1410 and the second temperature sensor 1420 are activated to instruct a subsequent operation to a user.

For example, the control module 1700 may be configured to provide a user with information, through the output module 1600, instructing the contact of the guide unit 1310 with the temperature measurement area TD1 of the stand 3000.

For another example, the control module 1700 may provide a user with information, through the output module 1600 which provides an alarm sound, indicating that the first temperature sensor 1410 and the second temperature sensor 1420 are activated. For example, when the first temperature sensor 1410 and the second temperature sensor 1420 are activated, through the output module 1600, the control module 1700 may provide a user with auditory information indicating that the first temperature sensor 1410 and the second temperature sensor 1420 are activated.

In this case, as described above, a user may instruct, through the second input module 1520, temperature measurement to determine whether the first temperature sensor 1410 and the second temperature sensor 1420 operate normally.

Meanwhile, although not shown in FIG. 19, when it is determined that difference between the first temperature information and the second temperature information is within a preset threshold at S1300, the control module 1700 may output, through the output module 1600, information instructing the presetting of cooling time information and/or cooling temperature information to a user.

For example, it is possible to provide a user with information related to initiating the presetting of the cooling time information and/or the cooling temperature information in a visual form through the output module 1600 having the shape of a display.

For another example, it is possible to provide a user with information related to initiating the presetting of the cooling time information and/or the cooling temperature information in an auditory form through the output module 1600 having the shape of a speaker.

In response to this, a user may input the cooling time information and/or the cooling temperature information through the input module 1500. For example, a user may input the cooling time information and/or the cooling temperature information by using the first input module 1510 having the shape of a wheel switch illustrated in FIG. 24. This will be described in detail with reference to FIGS. 23 and 24.

However, the above description is only an example, and of course, any suitable information may be provided to a user in a visual form, an auditory form, and/or a tactile form, and the like.

Figure 22:
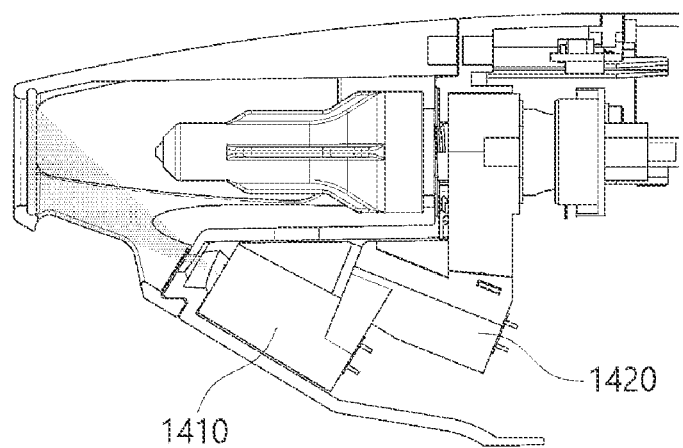
FIG. 22 is a view illustrating an aspect in which at least any one temperature sensor of a first temperature sensor (1410) and a second temperature sensor (1420) is used to measure temperature information of a target according to the embodiment of the present specification.
Figure 22:
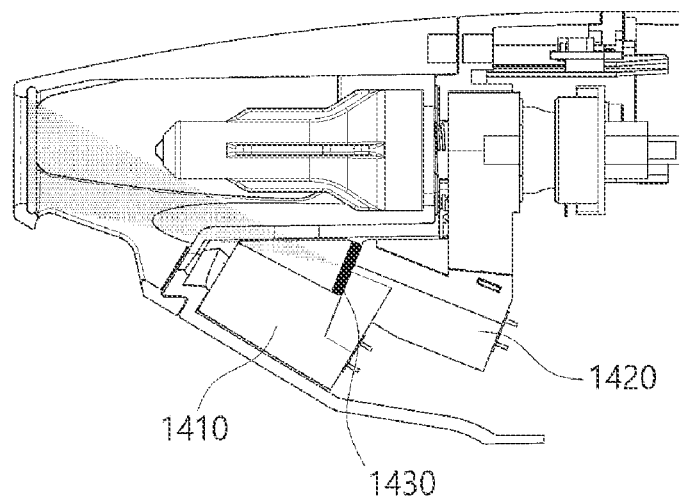

Referring to FIG. 22, FIG. 22 is a view illustrating an aspect in which at least any one temperature sensor of a first temperature sensor 1410 and a second temperature sensor 1420 is used to measure temperature information of a target according to the embodiment of the present specification.

For example, in measuring temperature information of a target after the step S1400, the control module 1700 deactivates the second temperature sensor 1420 and is located at a position closer to a target, and thus may obtain temperature information of a target measured by the first temperature sensor 1410 to measure the temperature of the center of the target more precisely.

For another example, in measuring temperature information of a target after the step S1400, the control module 1700 may deactivate the first temperature sensor 1410 and may obtain temperature information of a target measured by the second temperature sensor 1420. In this case, the second temperature sensor 1420 is disposed to be spaced more apart from a targeted area than the first temperature sensor 1410, so the second temperature sensor 1420 may further include a lens 1430 for more accurately measuring the temperature information of a target.

However, this is only an example, and in relation to the step S1400, the control module 1700 may be embodied to measure the temperature of a targeted area for controlling the subsequent cooling operation by using both the first temperature sensor 1410 and the second temperature sensor 1420.

Figure 23:
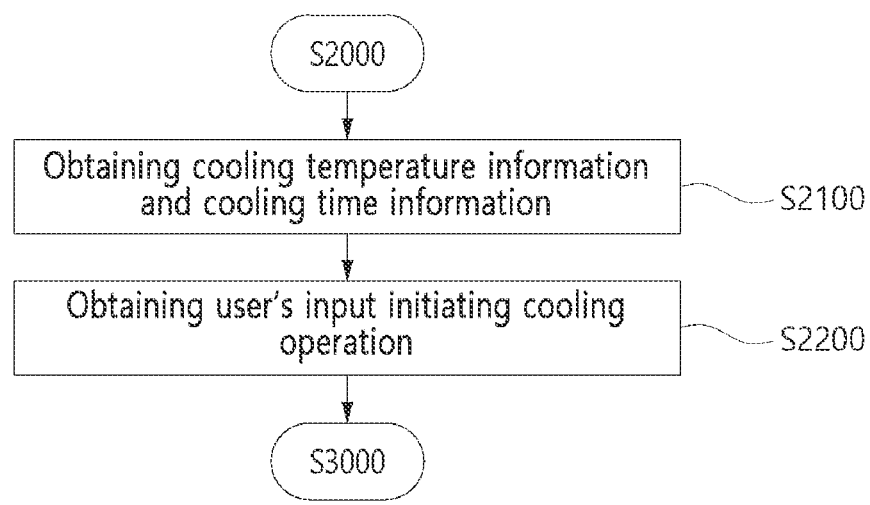
FIG. 23 is a flowchart related to the operation of the control module (1700) obtaining an input for initiating a cooling operation according to the embodiment of the present specification.
Figure 24:
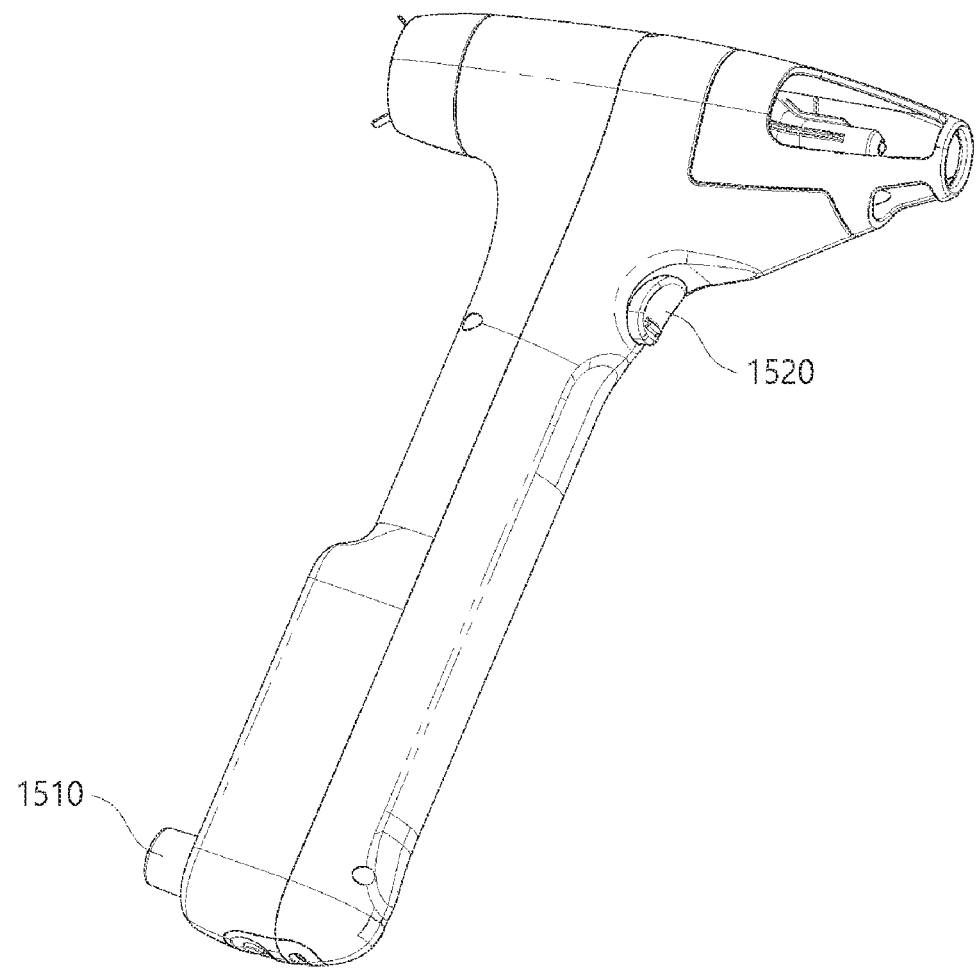
FIG. 24 is a view illustrating a plurality of input modules (1500) according to the embodiment of the present specification.
Figure 25:
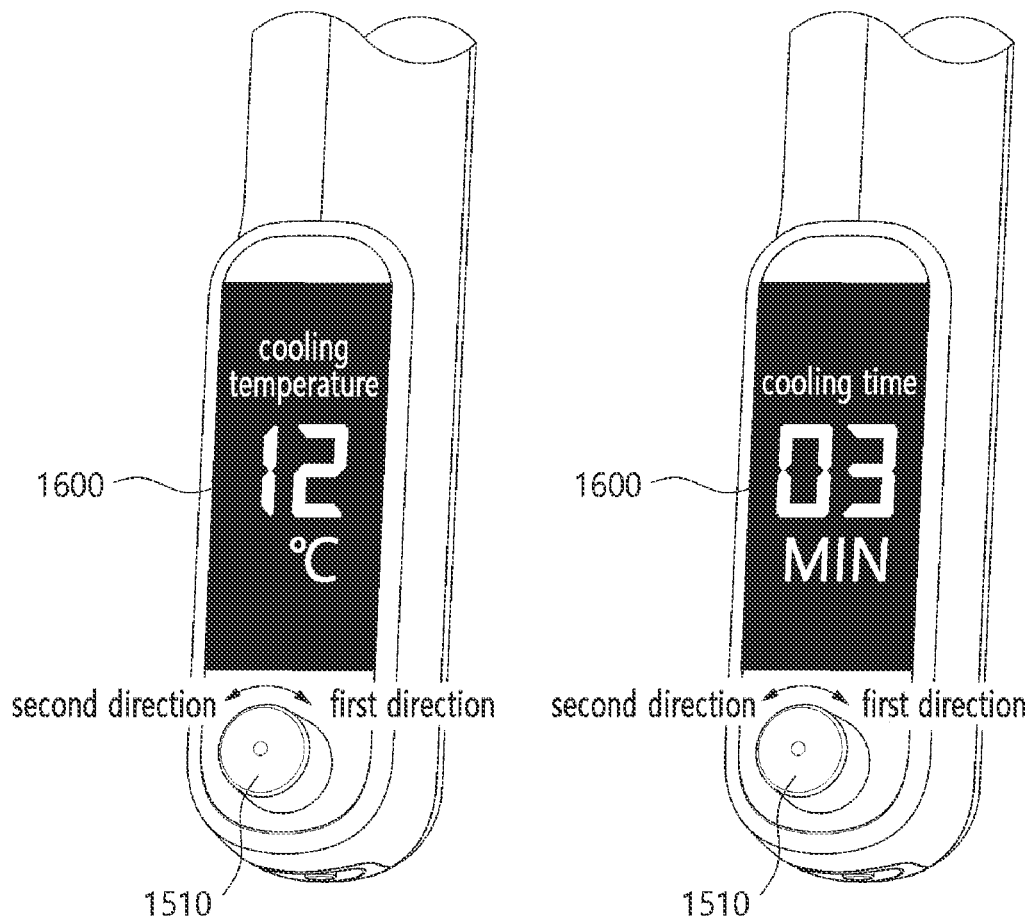
FIG. 25 is a view illustrating an aspect in which information related to a cooling condition is obtained through an input module (1510) according to the embodiment of the present specification.

FIG. 23 is a flowchart related to the operation of the control module 1700 obtaining an input for initiating a cooling operation according to the embodiment of the present specification. FIG. 24 is a view illustrating at least one input module 1500 according to the embodiment of the present specification. FIG. 25 is a view illustrating an aspect in which information related to a cooling condition is obtained through the first input module 1510 according to the embodiment of the present specification.

A cooling condition related to cooling temperature and a period of cooling time may vary depending on the type of treatment and a treatment area, etc. Accordingly, the cooling device 1000 according to the embodiment of the present specification may be embodied to preset a cooling condition related to cooling temperature and a cooling time, etc. according to the type of treatment aimed by a user.

Referring to FIG. 23, the method of obtaining an input to initiate a cooling operation may include the step S2100 of obtaining cooling temperature information and cooling time information and the step S2200 of obtaining the input of a user to initiate the cooling operation.

Referring to FIG. 24, as described above, the cooling device 1000 disclosed in the present specification may include at least one input module.

For example, the cooling device 1000 includes one input module 1500, and a user may change the form of an input by using the one input module 1500 to input cooling time information and cooling temperature information or to instruct the initiation of the cooling operation. For example, the cooling device 1000 may be embodied such that cooling time information and/or cooling temperature information are obtained to be different by varying time for which a user pushes one input module 1500.

For another example, the cooling device 1000 may include a plurality of input modules 1500.

For example, the cooling device 1000 may include the first input module 1510 located to be adjacent to an end part of the gripping portion. The first input module 1510 may be provided in various forms as described above. For example, the first input module 1510 may be configured in the form of a wheel switch, and the control module 1700 may be configured to obtain different information according to the turning or pushing of the wheel switch of the first input module 1510 by a user.

For example, the cooling device 1000 may include the second input module 1520 located at a part at which the fingers are located when a user grips the gripping portion. The second input module 1520 may be provided in various forms as described above. For example, the second input module 1520 may be provided in the form of a button, and based on the input of user pushing the second input module 1520, the control module 1700 may obtain the input of instructing the initiation of the cooling operation or the input of instructing the measurement of the temperature of the temperature measurement area TD1 to determine whether the sensor module 1400 operates normally as described above.

The cooling device 1000 may include a plurality of input modules 1500 and may provide a user with an intuitive form of input, thereby increasing convenience of a user.

Referring back to FIG. 23, at the step S2100 of obtaining cooling temperature information and cooling time information, the control module 1700 may obtain information related to cooling condition including the cooling temperature information and the cooling time information through the first input module 1510.

Referring to FIG. 25, the first input module 1510 may be provided in the form of a wheel switch as described above.

Here, a user may input information related to the cooling condition by turning or pushing the wheel switch.

For example, the first input module 1510 may be turned by a user to obtain cooling temperature information. The user may preset a high targeted temperature to control a target while turning the first input module 1510 in a first direction. On the other hand, a user may preset a low targeted temperature to control a target while turning the first input module 1510 in a second direction. In this case, the output module 1600 may be configured to display to a user the change of the cooling temperature information according to the turning of the wheel switch. Meanwhile, a user may complete the presetting of cooling temperature information related to a targeted temperature to control the target by pushing the first input module 1510.

For another example, the first input module 1510 may be turned by a user to obtain cooling time information. The user may preset a long cooling time while turning the first input module 1510 in the first direction. On the other hand, a user may preset a short cooling time while turning the first input module 1510 in the second direction. In this case, the output module 1600 may be configured to display to a user the change of the cooling time information according to the turning of a wheel switch. Meanwhile, a user may complete the presetting of cooling time information related to a cooling time by pushing the first input module 1510.

However, the above description is only an example, and information related to cooling condition may be obtained through various input devices using various methods other than the wheel switch. Furthermore, information related to the cooling condition may mean encompassing any appropriate information related to a cooling operation other than cooling temperature information and cooling time information.

Referring back to FIG. 23, at the step S2200 of obtaining a user's input initiating the cooling operation, the control module 1700 may obtain a user's input initiating the cooling operation of the cooling device 1000.

For example, the control module 1700 may obtain an input of a user instructing the initiation of a cooling operation from the user through the second input module 1520, which is different from the first input module 1510. Specifically, a user may instruct the initiation of the cooling operation by pushing the second input module 1520 having the shape of a button. However, this is only an example, and a user's input related to the initiation of the cooling operation may be obtained through various input devices using various methods other than a button.

As described above, when it is determined that the sensor module 1400 described with reference to FIG. 19 operates normally, the cooling temperature information and the cooling time information may be initiated to be input, and a user inputs the cooling temperature information and the cooling time information through the input module (e.g., the first input module 1510), and the cooling device 1000 may cool a targeted area based on the preset cooling temperature information and the preset cooling time information.

However, this is only an example, and when a user does not input cooling temperature information and cooling time information through the first input module 1510 but inputs the initiation of a cooling operation through the second input module 1520, the cooling device 1000 may be embodied to perform the cooling operation based on cooling temperature information and cooling time information which are pre-stored.

As described above, in response to a user's input instructing the initiation of a cooling operation, the control module 1700 may control the refrigerant flow control unit 1100 and/or the refrigerant temperature control unit 1200 and may initiate the cooling operation. Furthermore, the control module 1700 may be configured to control a current applied to the refrigerant temperature control unit 1200 based on information related to cooling condition including the cooling temperature information and cooling time information which are obtained and temperature information of a target.

For example, the control module 1700 controls whether to open or close the refrigerant flow control unit 1100, and controls thermal energy applied to a refrigerant by the refrigerant temperature control unit 1200 such that the degree of cooling transmitted to a targeted area can be controlled.

For example, the control module 1700 controls whether to open or close the refrigerant flow control unit 1100 such that the degree of cooling transmitted to a targeted area.

For example, the control module 1700 controls whether to open or close the refrigerant flow control unit 1100 and a time period to open or close the refrigerant flow control unit 1100, and controls thermal energy applied to a refrigerant by the refrigerant temperature control unit 1200 such that the degree of cooling transmitted to a targeted area can be controlled.

Hereinafter, a method in which the control module 1700 controls the refrigerant flow control unit 1100 and/or the refrigerant temperature control unit 1200 will be described in more detail with reference to FIG. 26.

Figure 26:
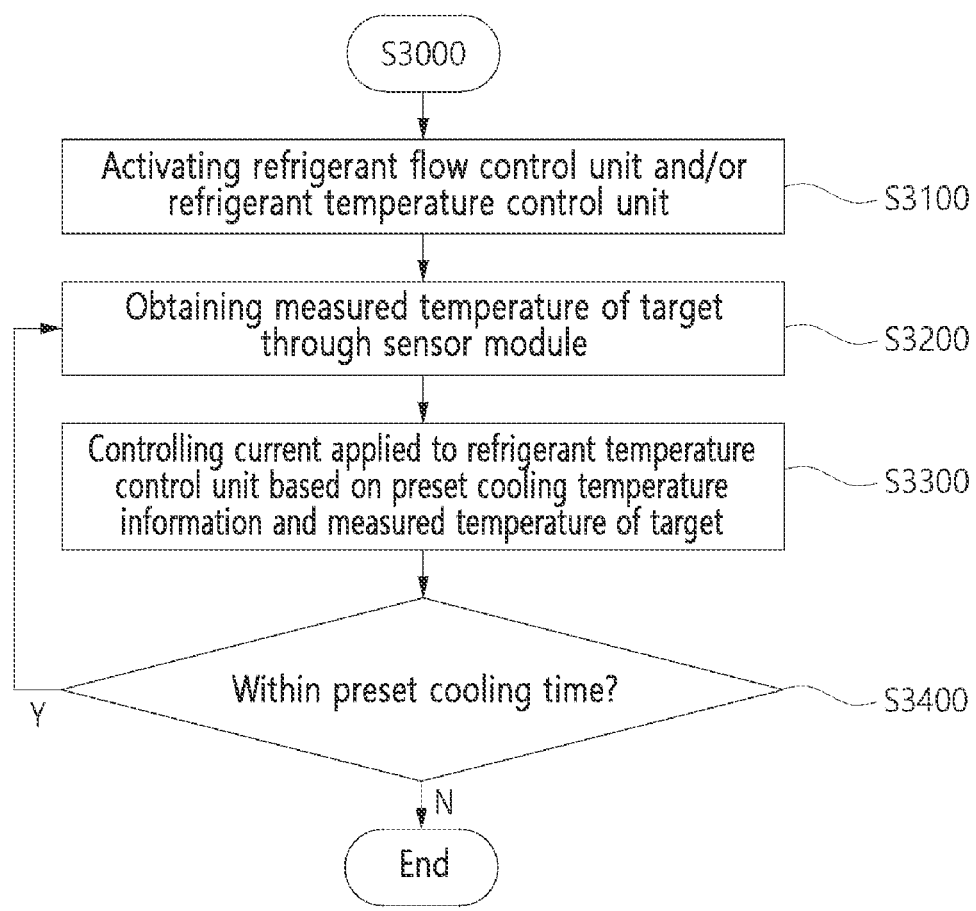
FIG. 26 is a flowchart illustrating a method in which the control module (1700) controls a refrigerant flow control unit (1100) and/or the refrigerant temperature control unit (1200) according to the embodiment of the present specification.

FIG. 26 is a flowchart illustrating a method in which the control module 1700 controls the refrigerant flow control unit 1100 and/or the refrigerant temperature control unit 1200 according to the embodiment of the present specification.

Referring to FIG. 26, the method of controlling the refrigerant flow control unit 1100 and/or the refrigerant temperature control unit 1200 by the control module 1700 may include the step S3100 of activating the refrigerant flow control unit 1100 and/or the refrigerant temperature control unit 1200, the step S3200 of obtaining the measured temperature of a target through the sensor module 1400, the step S3300 of controlling a current applied to the refrigerant temperature control unit 1200 based on the cooling temperature information and measured temperature of the target which are preset, and the step S3400 of determining whether a time for which a cooling operation is performed is within a preset cooling time.

In response to a user's input related to the initiation of cooling in relation to FIG. 23, the control module 1700 may be configured to activate the refrigerant flow control unit 1100 and/or the refrigerant temperature control unit 1200 at S3100.

For example, in response to the user's input initiating cooling, the control module 1700 may activate the valve of the refrigerant flow control unit 1100. Specifically, the control module 1700 may activate the valve so as to open the valve of the refrigerant flow control unit 1100. In addition, the control module 1700 may be configured to control opening/closing time of the valve of the refrigerant flow control unit 1100 based on the cooling time information preset in relation to FIG. 23.

For example, in response to a user's input initiating cooling, the control module 1700 may activate the refrigerant temperature control unit 1200. For example, the control module 1700 may activate the first temperature control member 1221 and/or the second temperature control member 1222 of the refrigerant temperature control unit 1200. Additionally, based on the cooling time information and the cooling temperature information preset in relation to FIG. 19, the control module 1700 may control a current value applied to the first temperature control member 1221 and/or the second temperature control member 1222 of the refrigerant temperature control unit 1200 so as to control the temperature of a refrigerant to be sprayed initially.

Meanwhile although not shown in FIG. 26, the control module 1700 may be configured to activate the sensor module 1400 in addition to the refrigerant flow control unit 1100 and the refrigerant temperature control unit 1200 at S3100. For example, as described above in FIG. 19, at least one sensor of the first temperature sensor 1410 and the second temperature sensor 1420 may be configured to be activated even before the step S3100. However, this is an example, and even if difference between the first temperature information T1 and the second temperature information T2 is within the preset threshold, the control module 1700 may be configured to deactivate both the first temperature sensor 1410 and the second temperature sensor 1420 and then to activate at least one sensor of the first temperature sensor 1410 and the second temperature sensor 1420 at S3100.

At the step S3200 of obtaining the measured temperature of a target through the sensor module 1400, the control module 1700 may obtain the temperature of a target measured by the sensor module 1400. For example, the temperature of a target may be measured through at least any one temperature sensor of the first temperature sensor 1410 and the second temperature sensor 1420 of the sensor module 1400. In this case, the sensor module 1400 may transmit the measured temperature of a target to the control module 1700.

At the step S3300 of controlling a current applied to the refrigerant temperature control unit 1200, the control module 1700 may control a current applied to the refrigerant temperature control unit 1200 based on the preset cooling temperature information obtained in relation of FIG. 23 and the measured temperature of a target obtained at S3200.

For example, when a preset cooling temperature is lower than a measured temperature of a target, the control module 1700 may decrease a value of a current applied to the first temperature control member 1221 and the second temperature control member 1222 of the refrigerant temperature control unit 1200. Through this, thermal energy applied to a refrigerant from the first and second temperature control members 1221 and 1222 may be decreased, and the temperature of the refrigerant may be controlled such that the temperature of the target approximates the preset cooling temperature.

For another example, when a preset cooling temperature is higher than a measured temperature of a target, the control module 1700 may increase a value of current applied to the first temperature control member 1221 and the second temperature control member 1222 of the refrigerant temperature control unit 1200. Through this, thermal energy applied to a refrigerant from the first and second temperature control members 1221 and 1222 may be increased, and the temperature of the refrigerant may be controlled such that the temperature of the target approximates the preset cooling temperature.

At the step S3400 of determining whether a time for which a cooling operation is performed is within a preset cooling time, the control module 1700 may be configured to determine whether the time for which the cooling operation is performed is within the preset cooling time based on the preset cooling time information obtained in relation to FIG. 23. To this end, the control module 1700 may be configured to additionally obtain time information at a time point at which a cooling operation starts (e.g., a time point at which the valve is opened) and present time information.

For example, when a time between a time point at which a cooling operation initiates and a present time point is shorter than the preset cooling time, the control module 1700 may determine that the time for which the cooling operation is performed is within the preset cooling time.

In this case, the valve of the refrigerant flow control unit 1100 may be controlled to be continuously activated such that a refrigerant is sprayed to a target.

In addition, when it is determined that the time for which the cooling operation is performed is within the preset cooling time, the control module 1700 may be configured to repeatedly perform the step S3200 of obtaining the measured temperature of a target through the sensor module 1400, the step S3300 of controlling a current applied to the refrigerant temperature control unit 1200 based on the preset cooling temperature information and the measured temperature of a target, and the step S3400 of determining whether the time for which the cooling operation is performed is within the preset cooling time.

On the other hand, when a time between a time point at which the cooling operation initiates and a present time point exceeds the preset cooling time, the control module 1700 may be embodied to determine that the time for which the cooling operation is performed is not within the preset cooling time. In this case, the control module 1700 may be configured to stop the cooling operation.

For example, when it is determined that a time for which a cooling operation is performed is not within a preset cooling time, the control module 1700 may be configured to deactivate the valve of the refrigerant flow control unit 1100. In addition, when it is determined that the time for which the cooling operation is performed is not within the preset cooling time, the control module 1700 may be embodied to deactivate the refrigerant temperature control unit 1200.

In other words, when it is determined that the time for which the cooling operation is performed is not within the preset cooling time, the control module 1700 may be configured to deactivate components of the cooling device 1000 (e.g., the refrigerant flow control unit 1100, the refrigerant temperature control unit 1200, and the sensor module 1400, etc.) to stop the cooling operation.

Figure 27:
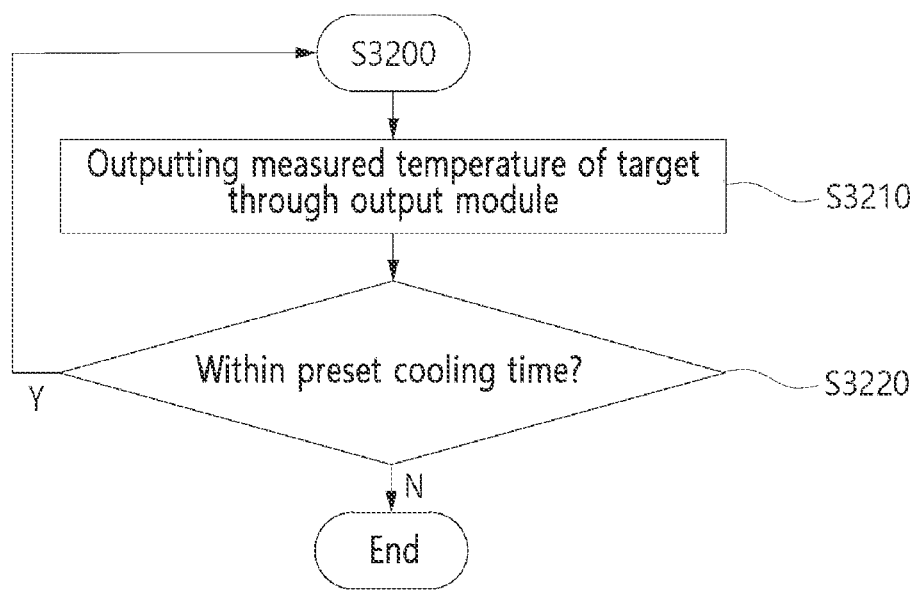
FIG. 27 is a flowchart illustrating a method in which the control module (1700) disclosed in the present specification outputs the measured temperature of a target through an output module (1600).
Figure 28:
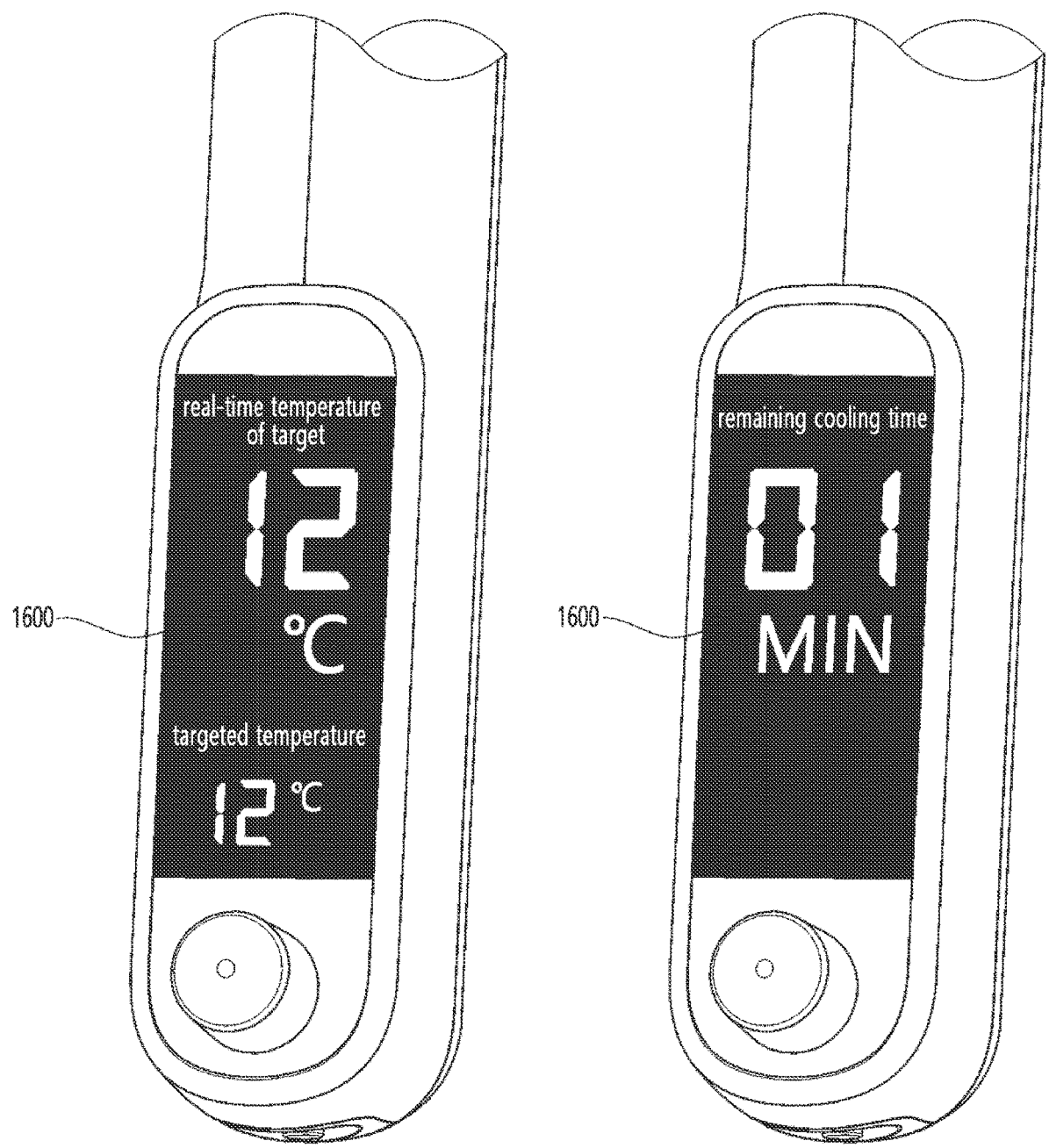
FIG. 28 is a view illustrating an aspect in which the measured temperature of a target is output through the output module (1600) disclosed in the present specification.

Referring to FIGS. 27 and 28, FIG. 27 is a flowchart illustrating a method in which the control module 1700 disclosed in the present specification outputs the measured temperature of a target through an output module 1600. FIG. 28 is a view illustrating an aspect in which the measured temperature of a target is output through the output module 1600 disclosed in the present specification.

Referring to FIG. 27, the control module 1700 may obtain the measured temperature of a target from the sensor module 1400 in real time, and may provide the measured temperature of a target in real time to a user through the output module 1600.

The method of outputting the measured temperature of a target by the control module 1700 may include the step S3200 of obtaining the measured temperature of a target through the sensor module 1400, the step S3210 of outputting the measured temperature of a target through the output module 1600, and the step S3220 of determining whether a time for which a cooling operation is performed is within a preset cooling time.

At the step S3200 of obtaining the measured temperature of a target through the sensor module 1400, as described above, the control module 1700 may obtain the temperature of a target measured by at least one temperature sensor of the first temperature sensor 1410 and the second temperature sensor 1420.

At the step S3210 of outputting the measured temperature of a target through the output module 1600, the control module 1700 may transmit the measured temperature of a target obtained at the step S3200 to the output module 1600.

Alternatively, the control module 1700 may transmit the cooling temperature information obtained in relation to FIG. 23 to the output module 1600.

Alternatively, the control module 1700 may transmit remaining cooling time information calculated based on cooling time information and cooling run time information obtained in relation to FIG. 23 to the output module 1600. Here, as described above in relation to FIG. 26, the cooling run time information may be calculated based on time information at a time point at which a cooling operation is initiated and present time information.

The output module 1600 may output the real-time temperature information of a target based on the measured temperature of a target which the output module receives. Alternatively, the output module 1600 may output the targeted temperature information of a target based on cooling temperature information which the output module receives. Alternatively, the output module 1600 may be configured to output remaining cooling time information to a user based on the remaining cooling time information which the output module receives.

For example, referring to FIG. 28, the output module 1600 may output the real-time temperature information of a target and the targeted temperature of a target to a user. Through this, a user may compare the real-time temperature of a target with the targeted temperature of a target to be controlled and thus may intuitively check whether the cooling operation is normally performed. Accordingly, the cooling device 1000 according to the embodiment of the present specification may safely implement a skin cooling procedure while preventing side effects caused by overcooling of a target.

For another example, referring to FIG. 28, the output module 1600 may output remaining cooling time information to a user. Through this, a user can immediately revise and supplement a cooling procedure plan by comparing the remaining cooling time with the procedure progress of a target. Accordingly, the cooling device 1000 according to the embodiment of the present specification may implement a cooling procedure in which side effects caused by overcooling of a target can be prevented and the effect of the procedure can be increased.

However, contents illustrated in FIG. 28 are merely examples for convenience of description, and any appropriate information may be processed and be provided to a user through the output module 1600.

Referring back to FIG. 27, the control module 1700 may, in a manner similar to the step S3400 of FIG. 26, be configured to determine whether a time for which a cooling operation is performed is within a preset cooling time based on preset cooling time information obtained in relation to FIG. 23.

For example, when a time between a time point at which a cooling operation initiates and a present time point is shorter than the preset cooling time, the control module 1700 may determine that the time for which the cooling operation is performed is within the preset cooling time.

In this case, the control module 1700 may be configured to repeatedly perform the step S3200 of obtaining the measured temperature of a target through the sensor module 1400, the step S3210 of outputting the measured temperature of a target through the output module 1600, and the step S3220 of determining whether the time for which a cooling operation is performed is within the preset cooling time. That is, the control module 1700 may be configured to continuously obtain the measured temperature of a target and provide information on the measured target temperature in real time to a user through the output module 1600.

On the other hand, when a time between a time point at which the cooling operation initiates and a present time point exceeds the preset cooling time, the control module 1700 may determine that the time for which the cooling operation is performed is not within the preset cooling time. In this case, the control module 1700 may be configured to stop the cooling operation. For example, the control module 1700 may be configured to deactivate the valve of the refrigerant flow control unit 1100 and the refrigerant temperature control unit 1200. In other words, the control module 1700 may be configured to deactivate the components of the cooling device 1000 (e.g., the refrigerant flow control unit 1100, the refrigerant temperature control unit 1200, and the sensor module 1400, etc.) so as to stop the co In the above, various control operations of the control module 1700 have been described. However, this is only an example, and any suitable method for controlling the temperature of a target to be a targeted temperature may be embodied in order to minimize side effects of a cooling procedure and to increase cooling efficiency while being safe.

MODE FOR INVENTION

As described above, in the best mode for carrying out the invention, related matters have been described.

The invention claimed is:
1. A system comprising:
a) a cooling device comprising an inflow hole and a first connecting part,
wherein the first connecting part comprises a bottom surface and a side surface,
wherein the bottom surface interfaces with the inflow hole, and wherein the side surface comprises a first screw thread and at least one groove;
b) a container comprising i) a body for storing a refrigerant and ii) a second connecting part on one end of the body, wherein the second connecting part comprises an outer surface comprising a second screw thread, and
wherein the first connecting part and the second connecting part are coupled via the first and second screw threads; and
c) a filter structure comprising i) a first sealing member having a first diameter, ii) a second sealing member having a second diameter, iii) a filter located between the first sealing member and the second sealing member, and iv) a grip unit located between the first sealing member and the second sealing member, wherein the grip unit comprises at least one grip member,
wherein when the container is connected to the cooling device,
i) the filter structure is placed between the container and the cooling device, and
ii) at least a portion of the grip member is placed within the groove,
wherein the inflow hole, the first sealing member, the second sealing member, and the container are aligned to form a path for the refrigerant.

2. The system of claim 1,
wherein when the filter structure is coupled to the cooling device, the first sealing member interfaces with the inflow hole, and the second sealing member interfaces with the container.

3. The system of claim 1,
wherein the first connecting part is coupled to the second connecting part such that the container and the cooling device are coupled via the first and second connecting parts.

4. The system of claim 1,
wherein the first or second sealing member prevents leakage of the refrigerant from the path.

5. The system of claim 1,
wherein the first sealing member comprises a first through-hole,
wherein the second sealing member comprises a second through-hole which is aligned with the first through-hole, and
whereby the refrigerant is fluidically coupled to the cooling device via the first and second through-holes.

6. The system of claim 1,
wherein the filter structure further comprises a protrusion configured to perforate the container to form a refrigerant discharge hole.

7. The system of claim 6,
wherein the protrusion comprises a third through-hole.

8. The system of claim 1,
wherein at least a portion of the refrigerant is released via a space between the groove and the grip member when the container is detached from the first connecting part.

9. The system of claim 1,
wherein the first or second sealing member comprises Teflon or Nylon 6.

10. The system of claim 1,
wherein the filter structure further comprises a filter support part, wherein the filter support part is located between the first sealing member and the second sealing member.

11. The system of claim 10,
wherein the filter is located between the first sealing member and the filter support part.

12. The system of claim 10,
wherein the grip member is an extended part of the filter support part.

13. The system of claim 1,
wherein the grip member comprises a first portion and a second portion extending from the first portion, and
wherein an angle formed by the first portion and the second portion is at least 90°.

14. A filter structure for filtering a refrigerant flowing from a container to a cooling device, comprising:
a first sealing member having a first diameter;
a second sealing member having a second diameter;
a filter located between the first sealing member and the second sealing member; and
a grip unit located between the first sealing member and the second sealing member, wherein the grip unit comprises a filter support part and at least one grip member connected to the filter support part.

15. The filter structure of claim 14, wherein the filter structure and the cooling device are coupled via the grip member.

16. The filter structure of claim 14,
wherein the first sealing member comprises a first through-hole,
wherein the second sealing member comprises a second through-hole which is aligned with the first through-hole, and
whereby the refrigerant is fluidically coupled to the cooling device via at least one of the first and second through-holes.

17. The filter structure of claim 14,
wherein the filter structure further comprises a protrusion configured to perforate the container to form a refrigerant discharge hole.

18. The filter structure of claim 17,
wherein the protrusion comprises a third through-hole.

19. The filter structure of claim 14,
wherein the filter support part is located between the first sealing member and the second sealing member.

20. The filter structure of claim 19,
wherein the filter is located between the first sealing member and the filter support part.

21. The filter structure of claim 19,
wherein the grip member is an extended part of the filter support part.

22. The filter structure of claim 14,
wherein the grip member comprises a first portion and a second portion extending from the first portion, and
wherein an angle formed by the first portion and the second portion is at least 90°.

23. The filter structure of claim 14,
wherein the second sealing member interfaces with the container when the filter structure is coupled to the container.

* * * * *